United States Patent [19]

Yoshioka et al.

[11] Patent Number: 4,698,339
[45] Date of Patent: Oct. 6, 1987

[54] CARBAPENEMS, THEIR PRODUCTION AND USE

[75] Inventors: Koichi Yoshioka, Kyoto; Norikazu Tamura, Suita; Hideaki Natsugari, Ashiya, all of Japan

[73] Assignee: Takeda Chemical Industries, Ltd., Osaka, Japan

[21] Appl. No.: 655,454

[22] Filed: Sep. 28, 1984

[30] Foreign Application Priority Data

Sep. 28, 1983 [WO] PCT Int'l Appl. ... PCT/JP83/00319
Sep. 21, 1984 [JP] Japan .................................. 59-199316

[51] Int. Cl.⁴ .................... C07D 487/04; A61K 31/40
[52] U.S. Cl. ..................................... 514/210; 540/350
[58] Field of Search ................. 260/245.2 T, 245.2 R, 260/239 A; 514/210; 540/350

[56] References Cited

U.S. PATENT DOCUMENTS

| | | | |
|---|---|---|---|
| 4,273,709 | 6/1981 | Christenson et al. | 260/245.2 T |
| 4,278,686 | 7/1981 | Corbett et al. | 260/245.2 T |
| 4,309,346 | 1/1982 | Christenson et al. | 260/245.2 T |

FOREIGN PATENT DOCUMENTS

| | | | |
|---|---|---|---|
| 0024832 | of 0000 | European Pat. Off. | |
| 2071099 | 9/1981 | United Kingdom | 260/245.2 T |

OTHER PUBLICATIONS

Medicinal Chemistry–Alfred Burser, Interscience Publishers, N.Y., N.Y., 1960.

*Primary Examiner*—Robert Gerstl
*Attorney, Agent, or Firm*—Wenderoth, Lind & Ponack

[57] ABSTRACT

A compound of the general formula:

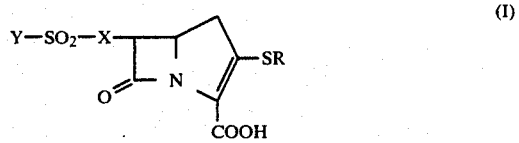

(I)

wherein X is a lower alkylene group which may optionally be substituted by a hydroxyl group, or a lower alkenylene group, Y is (1) a lower alkyl group, (2) a cycloalkyl group containing 3 to 8 carbon atoms, (3) a lower alkenyl group, (4) an aryl group, (5) an aralkyl group or (6) a 3- to 8-membered heterocyclic group, or the partial structural formula Y—SO₂—X—, with X and Y being combined with each other, represents a group of the formula:

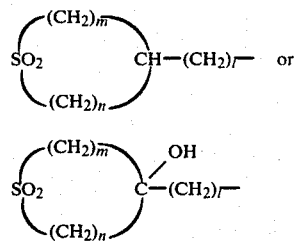

wherein l is an integer of 0 to 3, and m and n each is an integer of 0 to 6, provided that the sum of m and n is in the range of 2 to 6, and R is a hydrocarbon group which may optionally be substituted or a 3- to 8-membered heterocyclic group, or a pharmaceutically acceptable salt thereof a method of production thereof and use thereof. The compound (I) has antimicrobial and β-lactamase inhibitory activities.

8 Claims, No Drawings

CARBAPENEMS, THEIR PRODUCTION AND USE

This invention relates to novel 7-oxo-1-azabicyclo[3.2.0]hept-2-ene-2-carboxylic acid derivatives very stable against enzymes in vivo and having potent antimicrobial and β-lactamase inhibitory activities. In the present specification, the carbapenem compound of the formula:

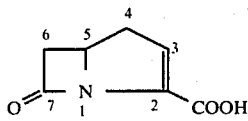

is referred to as 7-oxo-1-azabicyclo[3.2.0]hept-2-ene-2-carboxylic acid.

Recently, various 7-oxo-1-azabicyclo[3.2.0]hept-2-ene-2-carboxylic acid derivatives having antimicrobial activity have been produced.

For instance, U.S. Pat. No. 4,278,686 discloses 7-oxo-1-azabicyclo[3.2.0]hept-2-ene-2-carboxylic acids having a 1-(lower alkylthio)ethyl group at the 6-position. These compounds are known to have antimicrobial activity.

However, a disadvantageous feature of these compounds consists in that when taken up into living organisms, they are rapidly decomposed and thereby inactivated in vivo by enzymes (.e.g. dehydropeptidase, which is an enzyme occurring in the kidney), so that the antimicrobial activity originally intrinsic to the compounds cannot be fully displayed.

As a result of their continuous and intensive study in search of compounds which are stable in vivo against enzymes and have high antimicrobial and β-lactamase inhibitory activities, the present inventors found that compounds of the general formula:

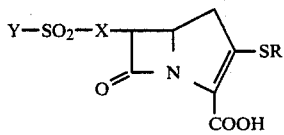 (I)

wherein X is a lower alkylene group which may optionally be substituted by a hydroxyl group, or a lower alkenylene group and Y is (1) a lower alkyl group, (2) a cycloalkyl group containing 3 to 8 carbon atoms, (3) a lower alkenyl group, (4) an aryl group, (5) an aralkyl group (6) a 3- to 8-membered heterocyclic group, or the partial structural formula: Y—SO₂—X—, with X and Y being combined with each other, represents a group of the formula

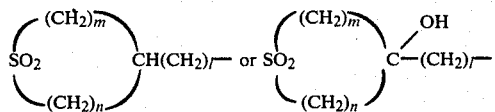

wherein l is an integer of 0 to 3, and m and n each is an integer of 0 to 6, provided that the sum of m and n is in the range of 2 to 6, and R is a hydrocarbon group which may optionally be substituted, or a 3- to 8-membered heterocyclic group or a pharmaceutically acceptable salt thereof, are fit for the above purpose. This finding and continued study have led to completion of the present invention.

Referring to the general formulas, X is a lower alkylene group containing 1 to 4 carbon atoms which may optionally be substituted by a hydroxyl group, such as methylene, methylmethylene, dimethylmethylene ethylene, propylene, butylene, hydroxymethylene, hydroxyethylene, hydroxymethylethylene, 1-hydroxy-2-methylethylene, hydroxyethylethylene or 1-hydroxy-2-ethylethylene, or a lower alkenylene group containing 2 to 4 carbon atoms, such as ethenylene, propenylene, 1-butenylene or 2-butenylene; Y is (1) a straight-chain or branched lower alkyl group containing 1 to 6 carbon atoms, such as methyl, ethyl, n-propyl, isopropyl, n-butyl, isobutyl, tert-butyl, n-pentyl, n-hexyl or isohexyl, (2) a cycloalkyl group containing 3 to 8 carbon atoms, such as cyclopropyl, cyclobutyl, cyclopentyl, cyclohexyl, cycloheptyl or cyclooctyl, (3) a lower alkenyl group containing 2 to 4 carbon atoms, such as vinyl, propenyl, 1-butenyl, 2-butenyl or 3-butenyl, (4) an aryl group preferably containing 6 to 14 carbon atoms, such as phenyl, naphthyl, biphenylyl or anthryl, (5) an aralkyl group preferably containing 7 to 10 carbon atoms, such as benzyl, phenethyl, phenylpropyl or phenylbutyl, or (6) a 3- to 8-membered heterocyclic group which contains 1 to 5 heteroatoms, such as nitrogen, oxygen or/and sulfur atoms, and may optionally be fused with a benzene ring and be in the oxide form, such as 1- or 2-aziridinyl, 2- or 3-pyrrolyl, 2- or 3-furyl, 2- or 3-thienyl, 2- or 3-pyrrolidinyl, 2- or 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, benzothiazolyl, indolinyl, benzopyranyl, 1,8- 1,5-, 1,6-, 1,7-, 2,7- or 2,6-naphthyridinyl or quinolyl, or the partial structural formula: Y—SO₂—X—, with X and Y being combined with each other, represents a group of the formula:

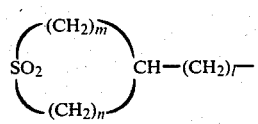

wherein l is an integer of 0 to 3, and m and n each is an integer of 0 to 6, provided that the sum of m and n is in the range of 2 to 6, such as

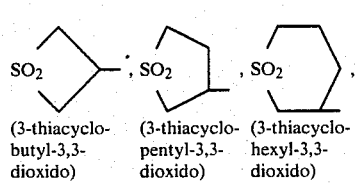

(3-thiacyclobutyl-3,3-dioxido) (3-thiacyclopentyl-3,3-dioxido) (3-thiacyclohexyl-3,3-dioxido)

-continued

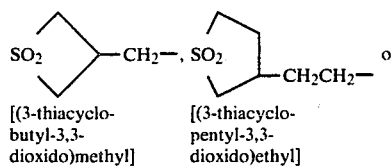

[(3-thiacyclo-butyl-3,3-dioxido)methyl]   [(3-thiacyclo-pentyl-3,3-dioxido)ethyl]

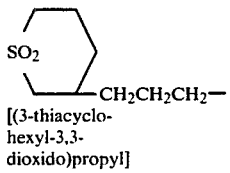

[(3-thiacyclo-hexyl-3,3-dioxido)propyl]

or a group of the formula:

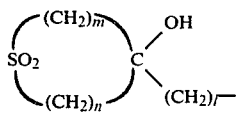

wherein each symbol is as defined above, such as

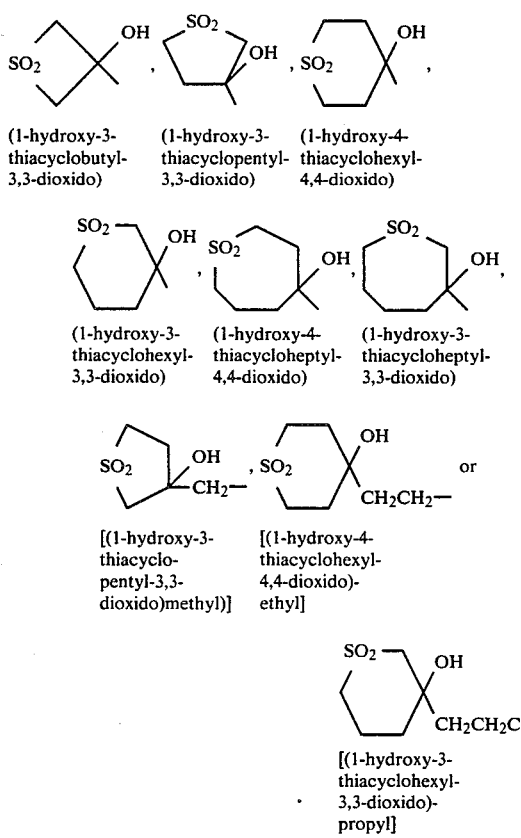

(1-hydroxy-3-thiacyclobutyl-3,3-dioxido)   (1-hydroxy-3-thiacyclopentyl-3,3-dioxido)   (1-hydroxy-4-thiacyclohexyl-4,4-dioxido)

(1-hydroxy-3-thiacyclohexyl-3,3-dioxido)   (1-hydroxy-4-thiacycloheptyl-4,4-dioxido)   (1-hydroxy-3-thiacycloheptyl-3,3-dioxido)

[(1-hydroxy-3-thiacyclo-pentyl-3,3-dioxido)methyl)]   [(1-hydroxy-4-thiacyclohexyl-4,4-dioxido)-ethyl]

[(1-hydroxy-3-thiacyclohexyl-3,3-dioxido)-propyl]

and R is a hydrocarbon group, such as a lower alkyl group containing 1 to 6 carbon atoms, a cycloalkyl group containing 3 to 8 carbon atoms, a lower alkenyl group containing 2 to 6 carbon atoms or an aryl group, which may optionally be substituted, or a 3- to 8-membered heterocyclic group which contains 1 to 5 heteroatoms such as nitrogen, oxygen or/and sulfur atoms, and may optionally be fused with a benzene ring and be in the oxide form.

Referring to the above definition, the lower alkyl group containing 1 to 6 carbon atoms is a straight-chain or branched lower alkyl group containing 1 to 6 carbon atoms, such as methyl, ethyl, n-propyl, isopropyl, n-butyl, isobutyl, sec-butyl, tert-butyl, n-pentyl, isopentyl, n-hexyl or isohexyl. The cycloalkyl group containing 3 to 8 carbon atoms is, for example, cyclopropyl, cyclobutyl, cyclopentyl, cyclohexyl, cycloheptyl or cyclooctyl. The alkenyl group containing 2 to 6 carbon atoms is a straight-chain or branched lower alkenyl group containing 1 to 6 carbon atoms, such as vinyl, allyl, iospropenyl, 2-methallyl, 2-butenyl or 3-butenyl. The aryl group is an aryl group preferably containing 6 to 14 carbon atoms, such as phenyl, α-naphthyl, β-naphthyl, biphenylyl or anthryl. The 3- to 8-membered heterocyclic group which contains 1 to 5 heteroatoms, such as nitrogen, oxygen or/and sulfur atoms, and may optionally be fused with a benzene ring and be in the oxide form, includes those mentioned in relation to the definition of Y.

The substituent of the hydrocarbon group which is substituted, represented by R may includes, among others, (1) a lower alkoxy group containing 1 to 6 carbon atoms, such as methoxy, ethoxy, n-propoxy, isopropoxy, n-butoxy, isobutoxy, sec-butoxy, tert-butoxy, n-pentyloxy, isopentyloxy, n-hexyloxy or isohexyloxy, (2) a lower alkoxycarbonyl group in which the alkoxy moiety contains 1 to 6 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, n-hexyloxycarbonyl or isohexyloxycarbonyl, (3) a 3- to 8-membered heterocyclic group (such as those mentioned above in relation to the definition of Y) which may optionally be substituted by (a) an imino-substituted lower alkyl group containing 1 to 6 carbon atoms, such as iminomethyl, 1-iminoethyl, 2-iminoethyl, 1-iminopropyl, 2-iminopropyl, 3-iminopropyl, 1-iminobutyl, 2-iminobutyl, 3-iminobutyl or 4-iminobutyl, (b) a lower alkyl group containing 1 to 6 carbon atoms, such as methyl, ethyl, n-propyl, isopropyl, n-butyl, isobutyl, tert-butyl, n-pentyl or n-hexyl, (c) an amino group which may optionally be protected, (d) a lower alkanoyl group containing 2 to 7 carbon atoms, such as acetyl, propionyl, butyryl, isobutyryl, n-pentanoyl, n-hexanoyl or n-heptanoyl, or (e) an oxo group, the number of the substituents being 1 to 3, (4) an acyloxy group, such as (a) a formyloxy group, (b) an alkanoyloxy group containing 2 to 7 carbon atoms, such as acetoxy, propionyloxy, n-butyryloxy, isobutyryloxy, n-pentanoyloxy or n-hexanoyloxy, (c) an arylcarbonyloxy group, such as benzoyloxy, 4-hydroxybenzoyloxy or 4-methoxybenzoyloxy, (d) an aralkylcarbonyloxy group, such as phenylacetoxy, 4-hydroxyphenylacetoxy or 4-methoxyphenylacetoxy, (e) a heterocyclecarbonyloxy group in which the heterocyclic moiety includes a 5- or 6-membered heterocyclic group which contains 1 to 3 heteroatoms such as sulfur, nitrogen or/and oxygen, such as 2-, 4- or 5-thiazolyl carbonyloxy, 2- or 3-thienyl carbonyloxy, 2- or 3-furylcarbonyloxy, or 2-amino-4- or 5-thiazolylcarbonyloxy, (f) a heterocycleacetoxy group in which the heterocyclic group includes a 5- or 6-membered heterocyclic group which contains 1 to 3 heteroatoms such as sulfur, nitrogen or/and oxygen, such as 2-, 4- or 5-thiazolylacetoxy, 2- or 3-thienylacetoxy, 2- or 3-furylacetoxy, or 2-amino-4- or 5-thiazolylacetoxy, (5) a lower alkylamino group containing 1 to 6 carbon atoms which may be substituted by (a) an imino group or (b) a lower alkylimino group containing 1 to 6 carbon atoms, such as methylamino, ethylamino, propylamino, n-butylamino, isobutylamino, tert-butylamino, n-heptylamino, n-hexylamino, dimethylamino, diethylamino, methylethylamino, di-n-propylamino, methyl-n-propylamino, ethyl-n-propylamino, di-n-butylamino, di-n-heptylamino, di-n-hexylamino; iminomethylamino, 1-iminoethylamino, 2-iminoethylamino, 1-iminopropylamino, 1-iminobutylamino; methyliminomethylamino, ethyliminomethylamino, n-propyliminomethylamino, 1-methyliminoethylamino, 1-ethyliminoethylamino or 1-n-propyliminoethylamino, the number of the substituents being 1 to 3, (6) a lower alkylthio group containing 1 to 6 carbon atoms, such as methylthio, ethylthio, n-propylthio, isopropylthio, n-butylthio, isobutylthio, tert-butylthio, n-pentylthio, isopentylthio, n-hexylthio or isohexylthio, (7) an arylthio group preferably containing 6 to 14 carbon atoms, such as phenylthio, biphenylylthio, naphthylthio or anthrylthio, (8) a carbamoyl group which may optionally be substituted by a lower alkyl group containing 1 to 6 carbon atoms, such as carbamoyl, methylcarbamoyl, ethylcarbamoyl, n-pentylcarbamoyl or isohexylcarbamoyl, (9) a carbamoylamino group which may optionally be substituted by (a) a phenyl group or (b) a lower alkyl group containing 1 to 6 carbon atoms, such as carbamoylamino, methylcarbamoylamino, ethylcarbamoylamino, diethylcarbamoylamino, propylcarbamoylamino, dibutylcarbamoylamino or n-hexylcarbamoylamino, the number of the substituents being 1 to 2, (10) an azido group, (11) a hydroxyl group which may optionally be protected (12) an imino group which may optionally be substituted by a lower alkyl group containing 1 to 6 carbon atoms, such as imino, methylimino, ethylimino, n-propylimino, isopropylimino, n-butylimino, isobutylimino, sec-butylimino, tert-butylimino, n-pentylimino, isopentylimino, n-hexylimino or isohexylimino, (13) a carboxyl group which may optionally be protected (14) a halogen atom, such as fluorine, chlorine, bromine or iodine, (15) an amino group which may optionally be protected, or (16) an acylamino group, such as an alkanoylamino group containing 2 to 7 carbon atoms (e.g. acetylamino, propionylamino, butyrylamino, pentanoylamino, heptanoylamino), a formylamino group, an aryl carbonylamino group (e.g. phenylcarbonylamino, naphtylcarbonylamino) or a heterocyclocarbonylamino group in which the heterocyclic group includes a 5- to 6-membered heterocyclic group which contains 1 to 3 heteroatoms such as sulfur, nitrogen or/and oxygen (e.g. 2-, 4- or 5-thiazolylcarbonylamino, 2- or 3-thienylcarbonylamino, 2- or 3-furylcarbonylamino, 2-amino-4- or 5-thiazolylcarbonylamino). The hydrocarbon group R may be substituted by 1 to 3 substituents (1)–(16).

Examples of the group represented by R include:

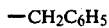

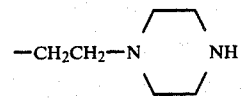

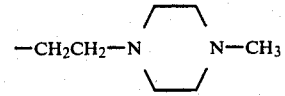

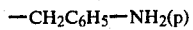

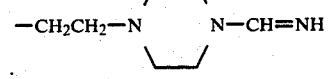

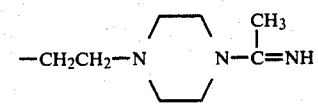

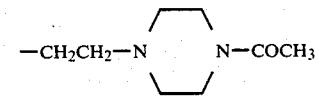

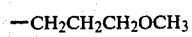

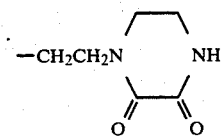

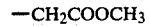

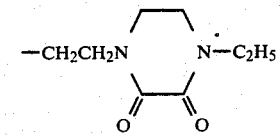

—CH₂COOC₂H₅
—CH₂CH₂COOCH₃
—CH₂CH₂COOC₂H₅
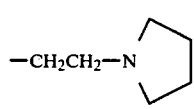
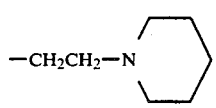
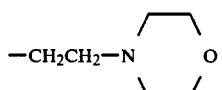
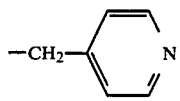
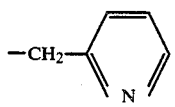
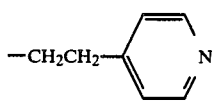
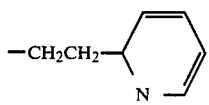
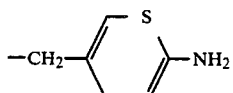
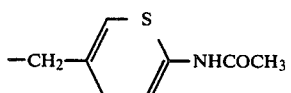
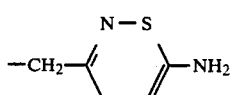
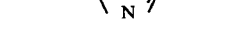
-continued
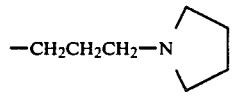
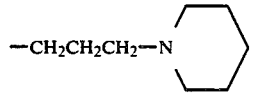
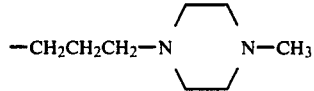
—CH₂CH₂CH₂N(CH₃)₂
—CH₂CH₂NH—CH=NH
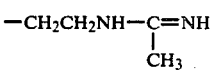
—CH₂CH₂NH—CH=N—CH₃
—CH₂CH₂NHCH=N—C₂H₅
—CH₂CH₂CH₂NH—CH=NH
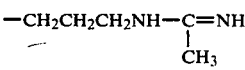
—CH₂CH₂SCH₃
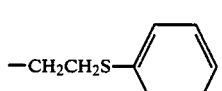
—CH₂CONH₂

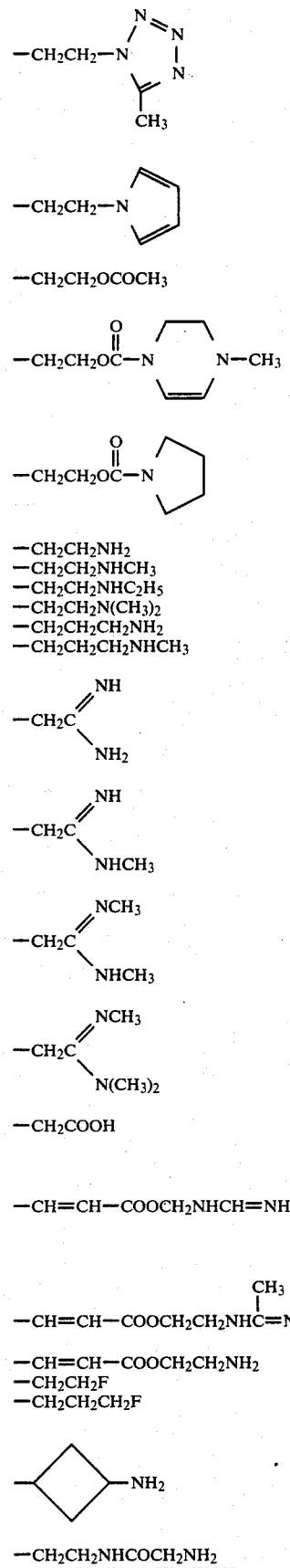

—CH₂CH₂NHCOC₂H₅
—CH₂CH₂NHCO—nC₃H₇
—CH₂CH₂NHCO—iso-C₃H₇
—CH₂CH₂NHCOC₆H₅
—CH=CH—NHCOCH₃
—C₆H₅OCH₃(p)
—C₆H₅OCH₃(m)

-continued
—C₆H₅—NH₂(o)
—C₆H₅—NH₂(p)
—C₆H₅—NH₂(m)
—C₆H₅—CH₃(o)
—C₆H₅—CH₃(p)
—C₆H₅—CH₃(m)
—C₆H₅—OCH₃(o)

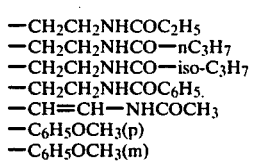
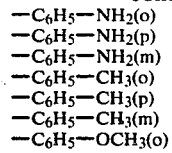

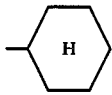
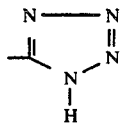

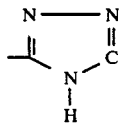

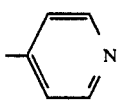
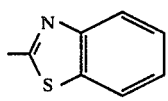

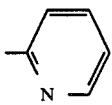
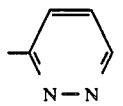

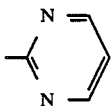
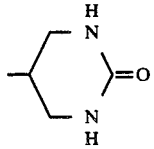

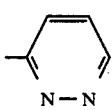
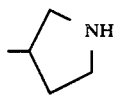

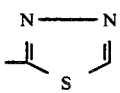

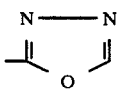

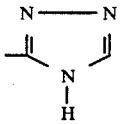

As the amino-protecting group, use can be made of any of those groups commonly used for this purpose in the field of β-lactam compound and peptide synthesis, including aromatic acyl group, such as phthaloyl, p-nitrobenzoyl or p-tert-butylbenzoyl; an aromatic sulfonyl group, such as p-tert-butylbenzenesulfonyl, p-toluenesulfonyl or benzenesulfonyl; an aliphatic acyl group, such as formyl, acetyl, propionyl, aminoacetyl, methylaminoacetyl, monochloroacetyl, dichloroacetyl, trichloroacetyl, trifluoroacetyl, maleoyl or succinyl; an aliphatic sulfonyl group, such as methanesulfonyl or ethanesulfonyl; an esterified carboxyl group, such as methoxycarbonyl, ethoxycarbonyl, t-butoxycarbonyl, isopropoxycarbonyl, 2-cyanoethoxycarbonyl, 2,2,2-trichloroethoxycarbonyl, 2-trimethylsilylethoxycarbonyl, benzyloxycarbonyl, 2-methylsulfonylethoxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl or phenyloxycarbonyl; and, further, an amino-protecting group other than acyl groups such as trityl, 2-nitrophenylthio, benzylidene, 4-nitrobenzylidene, a tri-lower($C_{1-6}$)alkylsilyl group (e.g. triethylsilyl or methyldiethylsilyl), benzyl or p-nitrobenzyl. The selection of said protective groups is not critical in practicing the present invention.

The protective groups for said carboxyl group include all groups generally usable as carboxyl-protecting groups in the field of β-lactam compound and organic chemistry, their ester moieties being, for example, methyl, ethyl, n-propyl, isopropyl, tert-butyl, tert-amyl, benzyl, p-nitrobenzyl, o-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, 2-methylsulfonylethyl, 2-trimethylsilylethyl, methylthiomethyl, trityl, 2,2,2-trichloroethyl, 2-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, iminomethylaminoethyl, 1-iminoethylaminoethyl, dimethylaminoethyl, pyridine-1-oxide-2-methyl, methylsulfinylmethyl, bis(p-methoxyphenyl)methyl or 2-cyano-1,1-dimethylethyl.

Furthermore, as the hydroxyl-protecting group, use can be made of any of those groups which can generally be used as hydroxyl-protecting groups in the field of β-lactam compound and organic chemistry, including an ester residue, such as acetyl or chloroacetyl; an esterified carboxyl residue such as 2,2,2-trichloroethoxycarbonyl or 2-trimethylsilylethoxycarbonyl; an ether residue, such as tertbutyl, benzyl, p-nitrobenzyl, trityl, methoxymethyl, methylthiomethyl or 2-methoxyethoxymethyl; a silyl ether residue, such as trimethylsilyl or tert-butyldimethylsilyl; as acetal residue, such as 2-tetrahydropyranyl or 4-methoxy-4-tetrahydropyranyl; or a sulfonic acid group. The selection of the above protective group is not critical in practicing the present invention, as in the cases of amino-protecting and carboxyl-protecting groups.

The compound (I) can be used in the free form or in the form of a pharmaceutically acceptable salt prepared by a per se known method. When the compound (I) contains a carboxyl group as a further substituent of R, it can be used, with respect to the carboxyl group, in the free form or in the form of a pharmaceutically acceptable salt prepared by a per se known method. Thus, for instance, it may be used in the form of a salt with a nontoxic cation, such as sodium or potassium, a basic amino acid, such as arginine, ornithine, lysine or histidine, or polyhydroxyalkylamine, such as N-methylglucamine, diethanolamine, triethanolamine or tris(hydroxymethyl)aminomethane. When R contains a basic group (e.g. an amino group), the compound (I) may also be used in the form of a pharmaceutically acceptable salt prepared by a per se known method. Thus, it may be used in the form of a salt with an organic acid, such as acetic acid, tartaric acid or methanesulfonic acid; an inorganic acid, such as hydrochloric acid, hydrobromic acid, sulfuric acid or phosphoric acid; or an acidic amino acid, such as arginine, aspartic acid or glutamic acid.

The compound (I) or a pharmaceutically acceptable salt thereof may occur as racemic mixtures, as the case may be. The racemic mixtures may be used for use as drugs as they are or may be separated into optically active isomers (d-form, l-form, etc.) by optical resolution for use as drugs.

The compound (I) or a pharmaceutically acceptable salt thereof has antibacterial activity against various gram-positive and gram-negative bacteria and is useful as drugs for humans and domestic animals, especially as antimicrobial agents for the treatment of infections caused by gram-positive bacteria (e.g. *Staphylococcus aureus*), gram-negative bacteria (e.g. *Escherichia coli, Klebsiella pneumoniae*), cephalosporin resistant bacteria (e.g. *Proteus vulgaris*), anaerobic bacteria (e.g. *Clostridium botulinum*), etc. The antimicrobial agents according to the invention may further be added to animal feed as antimicrobial agents for the preservation of said feed and may also be used as disinfectants for medical or dental equipment.

The compound (I) or a pharmaceutically acceptable salt thereof is used either alone or in combination with other active ingredients (.e.g. cephalosporin antibiotics, penicillin antibiotics) in any of various pharmaceutical preparation forms, such as tablets, capsules, powders, solutions, suspensions or elixirs. These preparations can be administered orally or parenterally (e.g. by intravenous or intramuscular injection).

Preparations for oral administration, such as tablets, capsules powders, or fine granules, may be prepared according to the conventional method by mixing with a per se known pharmaceutically acceptable excipient (e.g. starch, lactose, calcium carbonate, calcium phosphate), a binding agent (e.g. starch, gum arabic, carboxymethylcellulose, hydroxypropylcellulose, crystalline cellulose), a lubricant (e.g. magnesium stearate, talc), a disintegrating agent (e.g. carboxymethylcellulose calcium, talc), etc.

Liquid preparations for oral administration take the form of solutions, aqueous or oleaginous suspension, emulsions, syrups and elixirs, and may further occur as dry products to be dissolved in water or some other appropriate solvent just prior to use.

Such liquid preparations may contain a suspending agent (e.g. sorbitol syrup, methylcellulose, glucose/sugar syrup, gelatin) or/and a preservative (e.g. methyl p-hydroxybenzoate, propyl p-hydroxybenzoate). In preparing suppositories, common suppository bases, such as cocoa butter or other glycerides, may be used.

Preparations for use by injection may occur as solutions in oleaginous or aqueous solvents, suspensions, emulsions or powders and may contain one or more auxiliaries, such as a suspending agent, a stabilizing agent or a dispersing agent, if necessary. When the injectable preparations occur as powders, they are dissolved in an appropriate solvent, such as pyrogen-free distilled water, prior to administration.

Furthermore, these injectable preparations may contain other active ingredients (e.g. penicillin antiobiotics, cephalosporin antibiotics) so that they can exhibit a broader spectrum of antimicrobial activity.

The compound (I) or a pharmaceutically acceptable salt thereof can be used as agents for combating bacterial infections in the treatment of respiratory infection, urinary tract infection, suppurative diseases, biliary tract infection, intestinal infection, infection in obstertrics and gynecology and infection in surgery, among others. The daily dose is about 10 to about 200 mg/kg (body weight per human adult as the compound (I). Said dose is administered in two to four divided doses, namely at a single dose of about 5 to about 100 mg/kg (body weight), for example by intravenous injection.

In addition to the above modes of use, the compound (I) or a pharmaceutically acceptable salt thereof, may further be used in combination with β-lactam antibiotics since the compound (I) or pharmaceutically acceptable salt thereof has β-lactamase inhibitory activity. Examples of said β-lactam antibiotics are penicillin antibiotics, such as benzylpenicillin, phenoxymethylpenicillin, carbenicillin, ampicillin, amoxicillin or sulbenicillin, and cephalosporin antibiotics, such as cephaloridine, cephalothin, cefazolin, cephalexin, cefoxitin, cefacetrile, cefamandole, cefmenoxime, cefsulodin, cefotiam, cefotaxime, cephapirin, ceftizoxime, cephradine or cephaloglycine. Dosage forms such as injections, dry syrups, granules, tablets or capsules are prepared by per se conventional methods. They are preferably used as injections in the pharmaceutically acceptable salt or hydrate form. In such cases, the compound (I) or a pharmaceutically acceptable salt thereof can be used in a weight ratio of 1/10 to 10 parts (as the compound (I)) per part of β-lactam antibiotics, advantageously in a ratio of 1 to ⅛, e.g. 1/5 or 1/6. Thus, the compound (I) or a pharmaceutically acceptable salt thereof is administered in a daily dose of about 20 to 150 mg/kg (body weight) per human adult as the compound (I) in 1 to 6 divided doses, usually in 2 to 4 divided doses.

The compound (I) or a pharmaceutically acceptable salt thereof is produced by a per se known method.

Thus, the compound (I) or a pharmaceutically acceptable salt thereof can be produced by reacting a compound of the general formula:

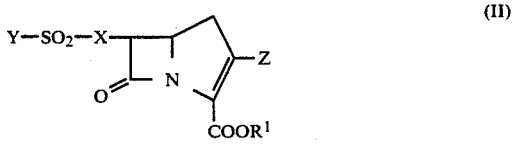

wherein Z is a leaving group; —COOR$^1$ is a carboxy group which may optionally be protected; and X and Y are as defined hereinbefore, or a salt thereof, with a compound of the general formula:

RSH    (III)

wherein R is as defined hereinbefore, followed by eliminating the protective group, if necessary.

Referring to the above formula (II), the leaving group Z is exemplified by a phenylsulfonyloxy group which may be substituted by a lower alkyl group containing 1 to 6 carbon atoms (e.g. methyl, ethyl, n-propyl, n-hexyl), nitro or a halogen atom, such as phenylsulfonyloxy, p-toluenesulfonyloxy, p-nitrophenylsulfonyloxy, p-bromophenylsulfonyloxy or p-iodophenylsulfonyloxy. The leaving group Z is exemplified by a lower alkylsulfonyloxy group containing 1 to 5 carbon atoms, such as methanesulfonyloxy or ethanesulfonyloxy. The leaving group Z is exemplified by a halogen atom such as chlorine or bromine. The leaving group Z is exemplified by a diarylphosphoryloxy group such as diphenylphosphoryloxy; or a di-(a lower alkyl group containing 1 to 6 carbon atoms)-substituted phosphoryloxy group such as diethylphosphoryloxy.

As the protective group for the carboxyl group of R$^1$, use is made of those mentioned hereinbefore.

In this reaction, the compound (II) and the compound (III) may be used each in the free form or in the form of a salt with an alkali metal such as lithium, sodium or potassium, an alkaline earth metal such as calcium or magnesium, or silver. In this reaction, the compound (II) or a salt thereof is used in an amount of about 1 to 10 moles, preferably about 1 to 5 moles, per mole of the compound (III) or a salt thereof.

The reaction is usually carried out in a solvent. Examples of the solvent include halogenated hydrocarbons such as dichloromethane or chloroform, nitriles such as acetonitrile, ethers such as dimethoxyethane or tetrahydrofuran, dimethylformamide, dimethyl sulfoxide, and hexamethylphosphoramide. A base may further be added to promote the reaction with advantage. Examples of the base include sodium hydrogen carbonate, potassium hydrogen carbonate, sodium carbonate, potassium carbonate, sodium hydride, potassium hydride, sodium amide, sodium methoxide, triethylamine, diisopropylethylamine and pyridine. The base is added generally in an amount of about 1 to 10 moles, preferably about 1 to 5 moles, per mole of the compound (II). The reaction is carried out within the temperature range of about −50° C. to 40° C., preferably about −30° C. to 20° C. The reaction time is about 1 to 72 hours, preferably about 1 to 24 hours.

When the thus-obtained compound (I) or a pharmaceutically acceptable salt thereof contains a protective group, the protective group can be eliminated by a per se known method, if necessary.

More concretely, when the carboxyl-protective group of the compound (I) or a pharmaceutically acceptable salt thereof is a haloalkyl, aralkyl or benzhydryl group or the like, the elimination of the protective group is accomplished by use of a reducing agent. The reducing agent usable in this reaction is the combination of zinc and acetic acid in cases where the carboxyl-protective group is a haloalkyl group, such as 2,2-dibromoethyl or 2,2,2-trichloroethyl, or the combination of hydrogen and a catalytic reduction catalyst, such as platinum oxide, platinum black, platinum sponge, palladium-on-carbon, palladium black, palladium-on-barium sulfate, palladium-on-barium carbonate, reduced nickel, Raney nickel or Urushibara nickel, or an alkali metal sulfite (e.g. sodium sulfite, potassium sulfite) in cases where the protective group is an aralkyl group, such as benzyl or p-nitrobenzyl, or a benzhydryl group. Furthermore, an o-nitrobenzyl group can be eliminated by light irraidation and a p-methoxybenzyl group can be eliminated by electrilytic reduction. The reaction is carried out in the presence of a solvent. Examples of solvents include alcohols, such as methanol or ethanol, ethers, such as tetrahydrofuran or dioxane, lower fatty acids containing 2 to 7 carbon atoms, such as acetic acid of propionic acid, and mixtures thereof with water. The reaction temperature is generally within the range of about 0° C. to 40° C. The reaction time is generally about 5 minutes to 12 hours.

When the amino-protecting group of the compound (I) or a pharmaceutically acceptable salt thereof is, for example, p-nitrobenzyloxycarbonyl, o-nitrobenzyloxycarbonyl, p-methoxybenzyloxycarbonyl or benzyloxycarbonyl, the protective group is eliminated in the same manner as the above-mentioned elimination of the carboxyl-protecting group.

When the hydroxyl-protecting group of the compound (I) or a pharmaceutically acceptable salt thereof is a lower alkanoyloxy group of 2 to 7 carbon atoms such as acetoxy, propionyloxy, or butyryloxy, the protective group can be eliminated by treatment with a base in an aqueous solvent. As the solvent, use is made of any of those solvents which are generally used in hydrolysis reaction. Preferred are water and mixtures of water and organic solvents, such as alcohols (e.g. methanol, ethanol) or ethers (e.g tetrahydrofuran, dioxane). The base usable in this reaction is not limited to some specific species, provided that it does not affect the β-lactam skeleton; thus, for instance an alkali metal carbonate, such as sodium carbonate or potassium carbonate is used. The reaction is conducted at about 0° C. to room temperature. The reaction time depends on the starting materials, reaction temperature and other factors, but generally is about 1 to 6 hours. Where a tri-lower ($C_{1-6}$) alkylsilyl group, such as tert-butyldimethylsilyl is used as the hydroxyl-protective group, the protective group is eliminated by treatment, for example, with tetrabutylammonium fluoride or a fluoride ion source, such as potassium fluoride. The use of an ether, such as tetrahydrofuran or dioxane as the solvent is appropriate in that case, and the reaction, when carried out in the neighbourhood of room temperature, is completed in about 10 to 18 hours.

Since the compound (I) has a carboxyl group, the compound (I) generally can form a salt with a base. Therefore, the compound (I) is recovered in the form of a salt and the obtained salt may be converted to the free form or different salts by per se known methods. Furthermore, the compound (I) obtained in the free form may be converted to a salt thereof by per se known methods. For the conversion of the compound (I) obtained in the salt form to the free form, an acid, for instance, is used. The kind of acid depends on the kind of protective group and other conditions, but inorganic acids, such as hydrochloric acid, sulfuric acid or phosphoric acid, and organic acids, such as formic acid, acetic acid or p-toluene-sulfonic acid, are frequently used. In addition, acid ion exchange resins etc. are used. As the solvent, use is made of hydrophilic organic solvents, such as acetone, tetrahydrofuran, methanol, ethanol or dioxane, and water, and a mixture thereof. In the method employing an acid, the reaction is generally carried out at room temperature, but may be conducted with cooling or warming. The reaction time is generally several tens of minutes to about 1 hour.

The compound (I) or a pharmaceutically acceptable salt thereof obtained in this manner can be isolated and purified by per se known procedures such as concentration, pH adjustment, solvent transformation, solvent extraction, crystallization, recrystallization, fractional distillation or/and chromatography.

When the substituent R of the compound (I) has free amino group, the amino group can further be converted to an amido group (e.g. acetamido, propionamido), a ureido group, an imino-substituted lower ($C_{1-6}$) alkylamino group, a lower ($C_{1-6}$) alkylimino-substituted lower ($C_{1-6}$) alkylamino group, a guanidino group, and so on.

The imino-substituted lower ($C_{1-6}$) alkylamino group and lower ($C_{1-6}$) alkylimino-substituted lower ($C_{1-6}$) alkylamino group are as those respectively mentioned hereinbefore.

When the substituent R of the compound (I) has a hydroxyl group, the hydroxyl group may further be converted to an acyloxy group (e.g. acetoxy, propionyloxy), a halogen atom, such as chlorine, bromine or iodine or an azido group.

The conversion of the amino group to an amido, ureido, imino-substituted lower ($C_{1-6}$) alkyl amino, lower ($C_{1-6}$) alkylimino-substituted lower ($C_{1-6}$) alkylamino or guanidino group can be effected by per se known methods. Thus, the conversion of the amino group to an amido group can be carried out by acylating with an acylating agent. The acylating agent is not critical but may be any of those generally used in acylating amino compounds, including lower ($C_{2-7}$) fatty acid anhydrides, such as acetic anhydride or propionic anhydride, and lower ($C_{2-7}$) fatty acid halide derivatives, such as acetyl chloride, propionyl chloride, n-butyryl bromide, isobutyryl bromide or methoxyalyl chloride. The acylating agent is used in an amount of 1 to 20 moles per mole of the compound (I).

This reaction is generally carried out in a solvent. The solvent is not critical, but preferably halogenated hydrocarbons such as chloroform or dichloromethane, or ethers, such as tetrahydrofuran or dioxane. This reaction is carried out preferably in the presence of a base. As the base, use is made of an organic base such as triethylamine or pyridine, or a fatty acid alkali metal salt, such as sodium acetate or potassium acetate. The reaction temperature is not critical, but preferably is about 0° C. to 40° C. The reaction time depends on the kind of the acylating agent and reaction temperature, but generally is about 30 minutes to 5 hours.

The conversion of the amino group to a ureido group is performed according to a per se known method, for example by reacting with a substituted isocyanate. Examples of the substituted isocyanate include methyl isocyanate, ethyl isocyanate, phenyl isocyanate and p-bromophenyl isocyanate. The substituted isocyanate is used in an amount of about 1 to 5 moles per mole of the compound (I). This reaction is generally carried out in a solvent. The examples of the solvent include dichloromethane, chloroform and tetrahydrofuran. The reaction temperature is about 0° C. to 40° C. and the reaction time is generally about 30 minutes to 5 hours.

The conversion of the amino group to an imino-substituted lower ($C_{1-6}$) alkylamino group or lower ($C_{1-6}$) alkylimino-substituted lower ($C_{1-6}$) alkylamino group is carried out by reacting with an imidoester compound.

Examples of imidoester compound include methyl formimidate, ethyl formimidate, benzyl formimidate, methyl acetimidate, ethyl acetimidate, methylphenyl acetimidate, ethyl N-methylformimidate, methyl N-ethylformimidate and methyl N-isopropylformimidate. The imidoester compound is used in an amount of about 1 to 10 moles per mole of the compound (I). This reaction is carried out in a solvent. Examples of the solvent include dioxane, tetrahydrofuran, dimethylformamide, chloroform, acetone acetonitrile and water. The reaction temperature is about 0° C. to 25° C. and the reaction time is generally about 1 to 6 hours.

The conversion of the amino group to a guanidino group is conducted by reacting with a urea derivative such as an O-alkyl- or O-arylpseudourea or an S-alkyl- or S-arylpseudothiourea. Said pseudourea includes, among others, O-methylpseudourea, S-methylpseudourea, O-2,4-dichlorophenylpseudourea and O,N,N'-trimethylpseudourea. Said pseudothiourea includes, for example, S-p-nitrophenyl-pseudothiourea. The urea derivative is used in an amount of about 1 to 10 moles per mole of the compound (I) This reaction is carried out in a solvent. Examples of the solvent include water, dimethylformamide and hexamethylphosphoramide. The reaction temperature is about 0° C. to 40° C. The reaction time is generally about 1 to 24 hours.

The conversion of the hydroxyl group to an acyloxy group, a halogen atom or an azido group can be achieved by per se known methods. Thus, the conversion of the hydroxyl group to an acyloxy group can be performed in the same manner as the conversion of the amino group to an amino group as mentioned hereinbefore. The conversion to a halogen atom can be achieved by halogenation according to a per se conventional method. The halogenating agent includes, among others thionyl chloride, thionyl bromide, oxalyl chloride, carbon tetrachloride-triphenylphosphine and carbon tetrabromide-triphenylphosphine. The halogenating agent is used in an amount of about 1 to 20 moles per mole of the compound (I). Suitable as the solvent are, for instance, ethers, such as tetrahydrofuran or dioxane, and aromatic hydrocarbons, such as benzene or toluene. The reaction is desirably conducted at a temperature of about 0° C. to room temperature and generally for about 15 minutes to 5 hours.

The conversion of the hydroxy group to an azido group is accomplished by reacting with hydrogen azide in the presence of a phosphine derivative and an azodicarboxylic acid diester or with diphenylphosphoric acid azide. As the phosphine derivative use is made of preferably triphenylphosphine or tri-n-butylphosphine, and as the azodicarboxylic acid diester, use is made of, for example, azodicarboxylic acid dimethyl ester or azodicarboxylic acid diethyl ester. Suitable as the solvent are halogenated hydrocarbons, such as dichloromethane or chloroform, and ethers, such as tetrahydrofuran or dioxane, among others. The reaction is suitably carried out at a temperature of about 0° C. to 60° C. for a period of about 5 minutes to 5 hours. The compound (I) or pharmaceutically acceptable salt thereof obtained in this manner can be isolated and purified by a per se known procedure, such as concentration, pH adjustment, solvent transformation, solvent extraction, crystallization, recrystallization, fractional distillation and/or chromatography.

The starting compound (II) can be produced by per se known methods or modifications thereof. Thus, for example, the compound (II) can be produced by the processes schematically given below (Chart 1) or modification thereof.

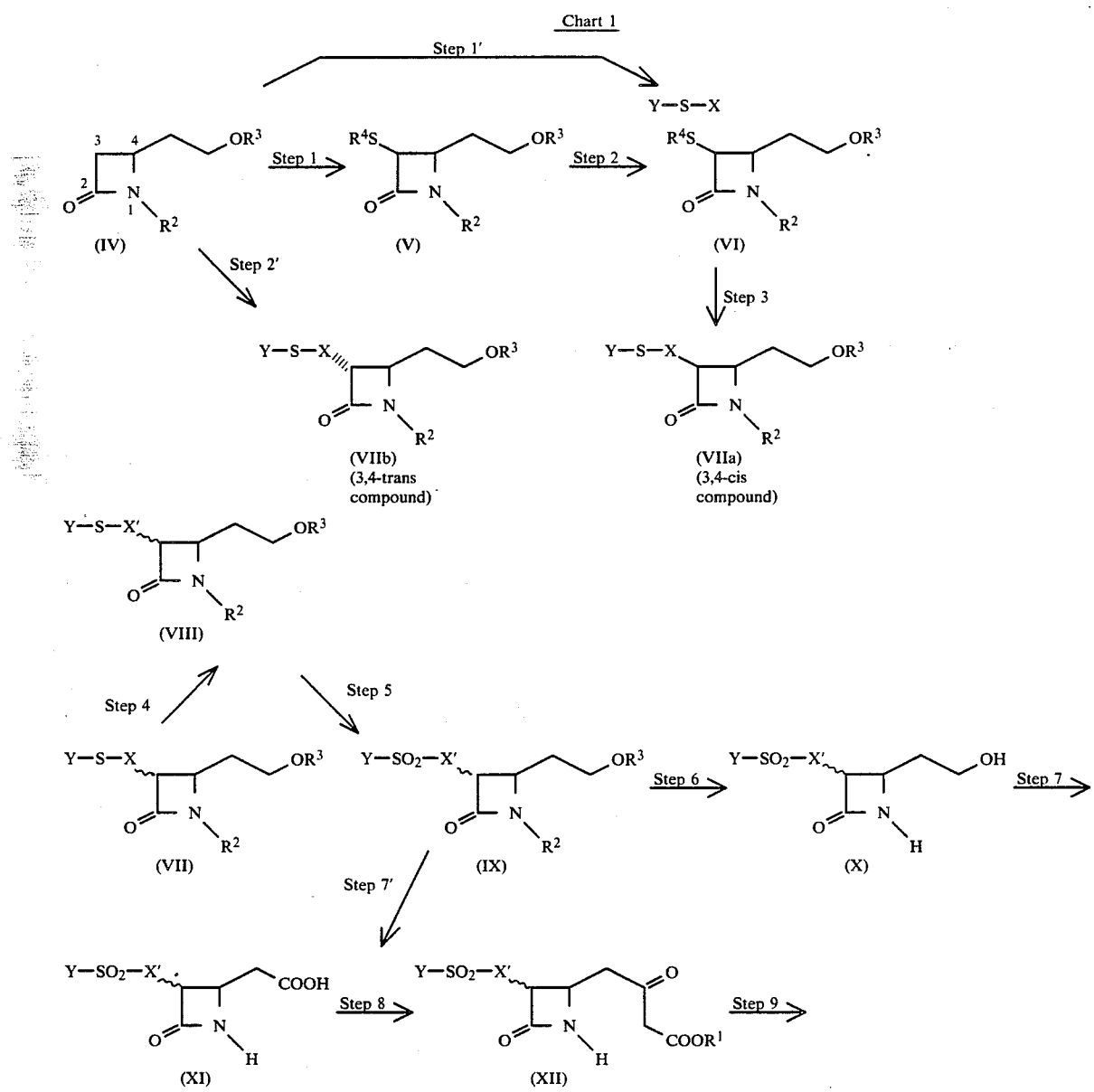

Chart 1

-continued
Chart 1

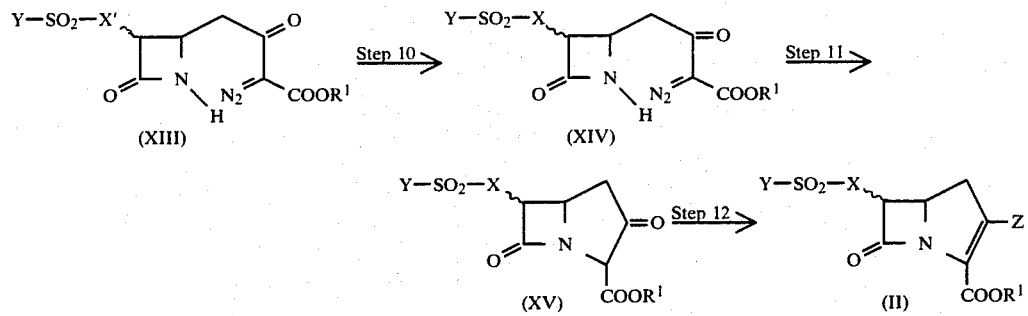

In the above formulas, $R^1$, X, Y and Z are as defined hereinbefore, X' is a lower alkylene group which may optionally be substituted by a protected hydroxyl group, or a lower alkenylene group, $R^2$ is a hydrogen atom or an amido-protecting group, $R^3$ is a hydrogen atom or a hydroxyl-protecting group, or $R^2$ and $R^3$ combine to represent a hydrocarbon group or a heterocyclic group, and $R^4$ is a hydrocarbon group or a heterocyclic group.

Referring to the above definitions, the lower alkylene group in the lower alkylene group which may optionally be substituted by a protected hydroxyl group represented by X' and the lower alkenylene group represented by X' are as respectively mentioned hereinbefore in relation to the definition of X.

The hydroxyl-protecting group in the lower alkylene group which may optionally be substituted by a protected hydroxyl group represented by X' and the hydroxyl-protecting group represented by $R^3$ are as mentioned hereinbefore. The amido-protecting group represented by $R^2$ includes a tri-(lower alkyl group of 1 to 6 carbon atoms)-substituted silyl group such as trimethylsilyl or t-butyldimethylsilyl, and a 5- or 6-membered cyclic ether group such as 2-tetrahydropyranyl. The hydrocarbon or heterocyclic group represented by combination of $R^2$ and $R^3$ and the hydrocarbon or heterocyclic group represented by $R^4$ are as respectively mentioned hereinbefore in relation to the definition of R.

Referring to Chart 1 the starting compound (IV) is produced according to per se known methods, for example, by subjecting 4-(2-hydroxyethyl)azetidin-2-one, a compound described in the literature [P. G. Christensen et al., Journal of Organic Chemistry, 45, 1130 (1980)], to amido and hydroxyl protecting reactions. The selection of the amido-protecting group $R^2$ and hydroxyl-protecting group $R^3$ is not critical provided that they do not adversely affect the subsequent reactions. Thus, examples of amido-protecting and hydroxy-protecting groups include, among others trimethylsilyl, t-butyldiphenylsilyl, t-butyldimethylsilyl and 2-tetrahydropyranyl. Furthermore, $R^2$ and $R^3$ may be combined so that the compound (IV) has the formula:

(XVI)

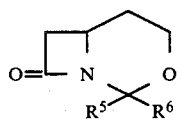

wherein $R^5$ and $R^6$ each is a hydrocarbon group, or, in other words, the amido and hydroxyl groups are simultaneously protected. The hydrocarbon group represented by $R^5$ or $R^6$ is as mentioned hereinbefore in relation to the definition of R and thus includes, among others a lower alkyl group containing 1 to 3 carbon atoms such as methyl, ethyl or isopropyl, or further, $R^5$ and $R^6$ is combined to represent an alkylene group containing 3 to 6 carbon atoms such as propylene, butylene, pentylene. The compound of formula (XVI) wherein $R^5$ and $R^6$ each is a methyl group has been described in the literature [Journal of Organic Chemistry, 45, 1130 (1980)]. This compound is produced by reacting 4-(2-hydroxyethyl)azetidin-2-one with 2,2-dimethoxypropane. This reaction is carried out in the presence of an acid catalyst. As the acid catalyst, use is made of boron trifluoride etherate or p-toluenesulfonic acid. The compound of the formula (XVI) other than the one wherein $R^5$ and $R^6$ each is a methyl group can easily be produced by using a ketone (e.g. diethyl ketone, methyl ethyl ketone, diisopropyl ketone, cyclopropanone, cyclobutanone, cyclopentanone or cyclohexanone) in place of 2,2-dimethoxypropane in the above reaction. For effecting the reactions mentioned hereinafter, the use of the compound (XVI) as the starting compound is preferred.

In step 1, the compound (IV) is sulfenylated at the 3-position with a sulfenylating agent to give the compound (V). The sulfenylating agent is, for example, a disulfide of the formula $(R^4S)_2$, a thiosulfonate of the formula $R^4S—SO^2R^4$ or an imide of the formula:

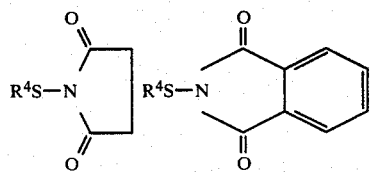

wherein $R^4$ is as defined hereinbefore. In this reaction, the sulfenylating agent can be used in an amount of about 1 mole per mole of the compound (IV).

This reaction is generally carried out in a solvent. Suitable as the solvent is, for example, tetrahydrofuran, dimethoxyethane, ether, dimethylformamide or dimethyl sulfoxide. This reaction is carried out in the presence of a base. As the base, use is made of a strong base such as lithium diisopropylamide, lithium isopropylcyclohexylamine, sodium amide or potassium hydride.

The base is suitably used in an amount of about 1 to 3 moles per mole of the compound (IV). The reaction temperature is within the range of about −80° C. to 0° C. The reaction time is about 30 minutes to 6 hours. The compound (V) may occur in the form of optical isomer due to the presence of asymmetric carbon atom at the 3-position. These isomers can be isolated individually by a per se conventional procedure such as column chromatography or recrystallization and each can be provided to the next reaction step. Said isomers may also be used in the next step in the form of a mixture, namely without conducting the above-mentioned isolation procedure.

In step 2, the compound (V) is alkylated at the 3-position with an alkylating agent to give the compound (VI). As the alkylating agent, use is made of a compound of the formula Y—S—X—A wherein A is a halogen atom or a p-toluenesulfonyl, methanesulfonyl, trifluoromethanesulfonyl or oxo group, and X and Y are as defined hereinbefore.

The halogen atom represented by A is, for example, chlorine, bromine or iodine.

In this step, the reaction is carried out at about −80° C. to 0° C. The alkylating agent is used in an amount of about 1 to 20 moles per mole of the compound (V). This reaction is carried out in a solvent in the presence of a base. As the base and solvent, use is made of the same as those used in step 1.

It is also practicable to perform the conversion reaction: the compound (IV)→the compound (V)→the compound (VI) in the same vessel without isolation of the compound (V), namely the compound (IV)→the compound (VI) as indicated as step 1' in Chart 1. The resulting compound (VI), may exist in the form of optical isomer due to the presence of an asymmetric carbon atom at the 3-position. These isomers can be isolated individually by a per se known procedure such as column chromatography or recrystallization. Each isomer can be used in the next reaction step. It is also posssible, however, to use them in the next reaction step in the form of a mixture without performing said isolation procedure.

In step 3, the compound (IV) is selectively reduced with a reducing agent to give a 3,4-cis-substituted azetidinone (VIIa).

Examples of the reducing agent include, among others organotin compounds, nickel compounds, mercury compounds and zinc compounds, preferably organotin compounds of the formula:

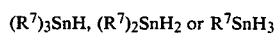

(R$^7$)$_3$SnH, (R$^7$)$_2$SnH$_2$ or R$^7$SnH$_3$ wherein R$^7$ is a hydrocarbon group. The hydrocarbon group represented by R$^7$ is as mentioned hereinbefore with respect to R and thus includes, among others a lower alkyl group containing 1 to 6 carbon atoms, such as methyl, ethyl, n-propyl, isopropyl, n-butyl, t-butyl or n-pentyl, a phenyl group which may optionally be substituted by a lower alkyl group containing 1 to 3 carbon atoms (e.g. methyl, ethyl, propyl). More concretely, as the reducing agent, use is made of triphenyltin hydride, tri-n-butyltin hydride, diphenyltin dihydride, di-n-butyltin dihydride, triethyltin hydride, trimethyltin hydride, n-butyltin trihydride, and the like. Among these, preferred are triphenyltin hydride and tri-n-butyltin hydride. The reducing agent is used generally in an amount of about 1 to 10 moles, preferably about 1.2 to 5 moles, per mole of the compound (VI). This reaction is carried out in the presence of 0.1 to 0.5 mole of a radical initiator. Examples of the radical initiator include azobis-isobutyronitrile and di-t-butyl peroxide. Light irradiation may be employed instead of using the radical initiator. The reaction is generally conducted in an inert solvent although it may be carried out using the reducing agent itself as the solvent. Suitable solvents are ketones, such as acetone or methyl ethyl ketone, ethers, such as dioxane or tetrahydrofuran, alcohols, such as methanol or ethanol, and aromatic hydrocarbons, such as benzene, toluene or xylene, among others. The reaction temperature generally is within the range of about 0° C. to 130° C., preferably about 10° C. to 100° C. The reaction may be conducted in an inert gas such as nitrogen or argon, if necessary. The reaction time is about 1 to 24 hours. This reaction mainly gives the compound (VIIa) having the cis configuration with respect to the 3- and 4-positions, accompanying the secondary formation of a minor amount of the compound (VIIb) having the 3,4-trans configuration. The isolation of the compound (VIIa) from the reaction mixture is performed by a per se known procedure. Thus, for example, the compound (VIIa) can be isolated by distilling off the solvent from the reaction mixture and subjecting the residue to recrystallization or column chromatography. The compound (VIIb) can be produced by alkylating the compound (IV) at the 3-position with an alkylating agent (step 2').

The conversion of the compound (IV) to the compound (VIIb) can be achieved in the same manner as the conversion of the compound (V) to the compound (VI).

In the subsequent steps 4 to 12, the 3,4-cis compound, the 3,4-trans compound and mixtures thereof can equally be used.

In case the compound (VII) has a hydroxyl group, step 4 is a process of producing the compound (VIII) by subjecting the compound (VII) to a protection reaction of the hydroxyl group. The protective group for the hydroxyl group in the compound (VIII) includes those mentioned hereinbefore, among which ether bond-forming protective groups such as 2-methoxyethoxymethyl, methoxymethyl or methylthiomethyl, are preferred. Among these, especially preferred is, for example, 2-methoxyethoxymethyl. The introduction reaction of the protective group is accomplished by a per se known method. For example, introduction of above-mentioned ether bond-forming protective group is realized by reaction of the compound (VII) with an alkyl halide. As the alkyl halide, use is made of 2-methoxyethoxymethyl chloride, methoxymethyl chloride or methylthiomethyl chloride. This reaction is carried out in the presence of a base. Examples of the base include triethylamine, diisopropylamine, pyridine, n-butyllithium and sodium hydride. The alkyl halide and the base each is used in a amount of about 1 to 20 moles, preferably about 1 to 5 moles per mole of the compound (VII). The reaction is generally performed in a solvent. Usable solvents are dichloromethane, chloroform, carbon tetrachloride, tetrahydrofuran, ether, dimethoxyethane, acetonitrile, dimethylformamide or dimethyl sulfoxide. The reaction temperature is within the range of about −20° C. to 100° C. The reaction time is about 30 minutes to 72 hours.

Step 5 is a process of producing the compound (IX) by oxidizing a group of the formula: Y—S—X'— at the 3-position of the compound (VIII) with an oxidizing agent to a group of the formula: Y—SO$_2$—X'—. The oxidation reaction is performed using a mild oxidizing agent which does not act on the β-lactam skeleton. Examples of the oxidizing agent include perbenzoic acid, ozone, phenyl dichloroiodide, hydrogen peroxide, sodium metaperiodate and sodium hypochlorite. Among these, especially preferred are perbenzoic acid and m-chloroperbenzoic acid. The oxidizing agent is used in an amount of about 2 moles or more per mole of the compound (VIII). The reaction is generally carried out in an inert solvent. Examples of the solvent include dichloromethane, chloroform and carbon tetrachloride. The reaction temperature is about −30° C. to about 25° C. The reaction time is about 10 minutes to 10 hours.

Step 6 is process of producing the compound (X) by elimination of the protective groups $R^2$ and $R^3$ of the compound (IX). The protective groups $R^2$ and $R^3$ are eliminated by per se known methods. For example, when the compound (IX) is derived from the compound (XVI), the elimination of the protective group is effected in the manner of hydrolysis employing an acid. This reaction is carried out in a solvent. Examples of the solvent include aqueous acetic acid. The reaction temperature is about 0° C. to 75° C. The reaction time is about 5 minutes to 16 hours.

Step 7 is a process of producing the compound (XI) by oxidizing the hydroxyethyl group at the 4-position of the compound (X) to a carboxymethyl group.

This oxidation reaction can be conducted using a variety of known oxidizing agents such as Jones reagent, potassium permanganate or silver oxide. The reaction is carried out in a solvent. Example of the solvent include aqueous tetrahydrofuran, aqueous dioxane and acetone. The reaction temperature is about −10° C. to 40° C. The reaction time is about 10 minutes to 24 hours. Most preferably, the oxidation reaction is carried out by using Jones reagent in acetone.

The compound (I) or a pharmaceutical acceptable salt thereof includes not only optical isomers but also a racemic mixture. The optically active compound (I) or a pharmaceutically acceptable salt thereof can be produced from an optically active compound (IV), and, when the compound (IV) is a racemic mixture, it is preferable to subject the intermediate compound (XI) (racemic mixture) obtained to optical resolution. The optical resolution can be realized by per se known methods, such as crystallization, fractional crystallization in the form of diastereomer salts formed by reaction with optically active amines (e.g. quinine, brucine, ephedrine, strychnine or morphine), or physical separation techniques, such as chromatography.

Step 8 is a process of producing the compound (XII).

In this step, the compound (XI) is reacted with an imidazolide reagent such as 1,1'-carbonyldiimidazole or 1,1'-carbonylbis(2-methylimidazole). The resulting imidazolide is further reacted, without isolation thereof, with the magnesium salt of a malonic acid derivative represented by the formula:

$(R^1OCOCH_2COO)_2Mg$ wherein $R^1$ is as defined hereinbefore.

The imidazolide reagent is used in an amount of about 1 to 2 moles per mole of the compound (XI). The magnesium salt of malonic acid derivative is used in an amount of about 1 to 3 moles per mole of the compound (XI). The reaction is generally carried out in a solvent. Examples of the solvent include tetrahydrofuran and dimethoxyethane. The reaction temperature is about 0° C. to 50° C. The reaction time is about 1 to 48 hours.

Step 9 is a process of producing the compound (XIII) by diazotizing the compound (XII). The diazotization is performed by reaction of the compound (XII) with an azide compound. Examples of the azide compound include p-carboxybenzenesulfonyl azide, p-toluenesulfonyl azide and methanesulfonyl azide. This reaction is carried out in the presence of a base. As the base, use is made of triethylamine, diethylamine and pyridine. The base is used generally in large excess per the compound (XII). The azide compound is used in an amount of about 1 to 2 moles per mole of the compound (XII). The reaction is generally carried out in a solvent. Examples of the solvent include acetonitrile, dichloromethane and tetrahydrofuran. The reaction temperature is about −10° C. to 40° C. The reaction time is about 1 to 48 hours.

Step 10 is a process of producing the compound (XIV) by eliminating the protective group from the protected hydroxyl group of the compound (XIII). However, the elimination of the protecting group need not always to be carried out in this step. If pharmaceutically acceptable, the protective group may remain in the compound (I). The protective group may also be eliminated in any of the subsequent steps, if necessary. The elimination of the protective group is performed by per se konwn methods. When the hydroxyl-protecting group is 2-methoxyethoxymethyl, the elimination of the protective group is carried out by reacting the compound (XIII) with a Lewis acid. As the Lewis acid, use is made of titanium tetrachloride or zinc bromide. This reaction is carried out in a solvent. Examples of the solvent include chloroform, dichloromethane and tetrahydrofuran. The Lewis acid is used in an amount of about 1 to 30 moles per mole of the compound (XIII). The reaction is conducted at a temperature of about −40° C. to 40° C. The reaction time is about 5 minutes to 10 hours.

Step 11 is a process of producing the compound (XV) by subjecting the compound (XIV) to ring closure reaction. The ring closure reaction is carried out in a solvent. Examples of the solvent include benzene, toluene and tetrahydrofuran. This reaction is generally carried out in the presence of a catalyst. As the catalyst, use is made of copper sulfate, copper powder, rhodium acetate or palladium acetate. The reaction temperature is about 50° C. to 110° C. The reaction times is about 1 to 5 hours. The reaction is generally carried out in an inert gas atmosphere such as nitrogen or argon. The ring closure reaction may also be effected by subjecting the compound (XIV) to light irradiation in a solvent. Examples of the solvent include benzene, tetrahydrofuran, carbon tetrachloride and diethyl ether. The reaction temperature is about −10° C. to 40° C. The reaction time is 30 minutes to 2 hours Step 12 is a process of producing the compound (II).

To produce the compound (II) wherein Z is a substituted sulfonyloxy group, the compound (XV) is reacted with a sulfonylating agent. As the sulfonylating agent, use is made of anhydrous p-toluenesulfonic acid, anhydrous p-nitrophenylsulfonic acid, 2,4-triisopropylphenylsulfonic anhydride, methanesulfonic anhydride, p-toluenesulfonyl chloride or p-bromophenylsulfonyl chloride. The sulfonylating agent is used in an amount of about 1 to 2 moles of the compound (XV). This reaction is carried out in a solvent. Examples of the solvent include dichloromethane, chloroform, acetonitrile, dimethoxyethane and tetrahydrofuran. This reaction is generally carried out in the presence of a base. As the base, use is made of triethylamine, diisopropylethylamine, pyridine or 4-dimethylaminopyridine. The reaction temperature is about −20° C. to 40° C. The reaction time is about 30 minutes to 5 hours. To produce the compound (II) wherein Z is a halogen atom, a halogenating agent such as oxalyl chloride, (C6H5)3PCl2, (C6H5)3PBr2, (C6H5O)3PBr2 or thionyl chloride is used instead of the sulfonylating agent. In this case, the compound (XV) can be converted to the compound (II) by conducting the reaction under the same conditions as above. To produce the compound (II) wherein Z is a disubstituted phosphoryloxy group, a phosphorylating agent such as diphenylphosphoryl chloride, dimethylphosphoryl chloride, diethylphosphoryl chloride is used instead of the sulfonylating agent in the above case. The reaction is carried out under the same conditions as above, whereby the compound (XV) can be converted to the compound (II).

The above-mentioned intermediate 3,4-cis compound (VIIa) can be produced by the processes schematically given below (Chart 2) or modifications thereof.

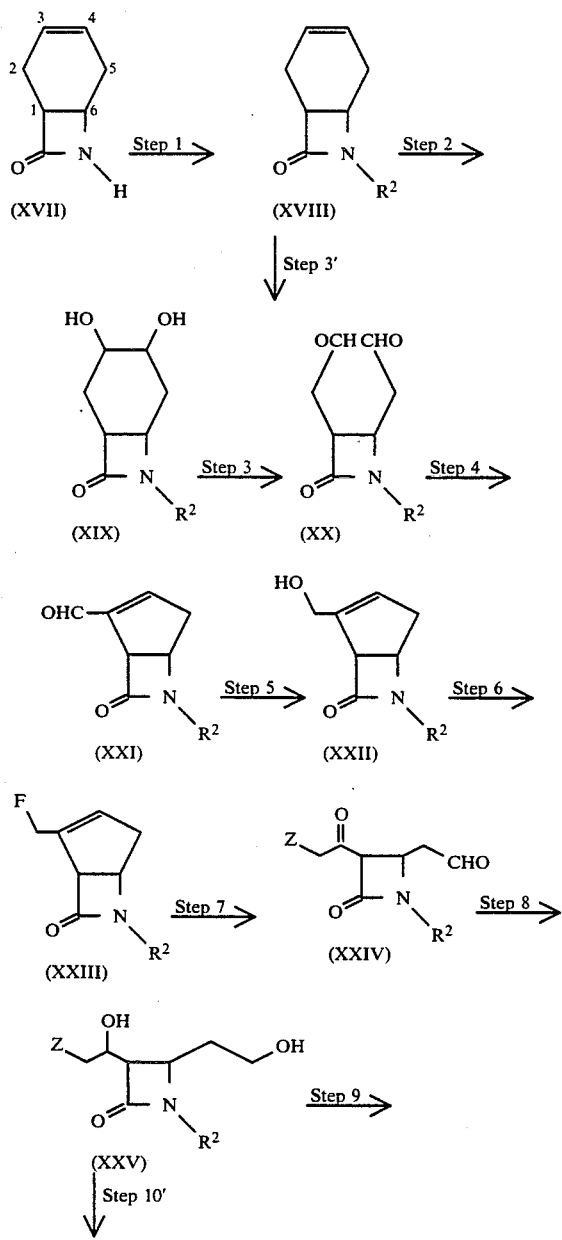

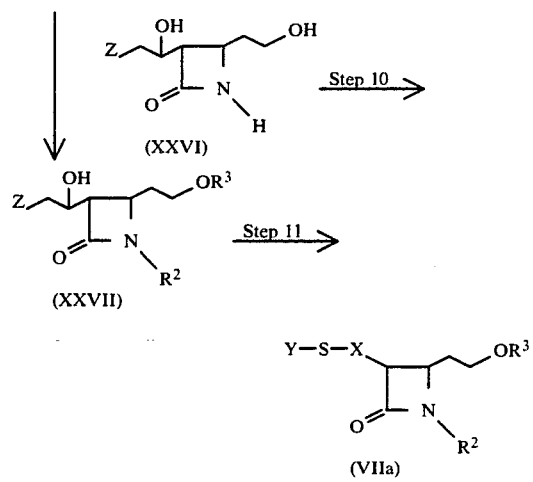

In the above formulas, X, Y, $R^2$, $R^3$ and Z as defined hereinbefore.

Referring to Chart 2, the starting compound (XVII) can be produced by the method of Paquett et al. [L. A. Paquett et al., J. Amer. Chem. Soc., 90, 3897 (1968)]. The compound (XVII) has a 1,6-cis configuration, and this relationship can be maintained throughout a series of subsequent reactions. The compound (XVII) thus can be converted to the 3,4-cis compound (VIIa).

Step 1 is a process in which the amido group of compound (XVII) is protected to give the compound (XVIII). As the amido protecting group, use is made of those mentioned hereinbefore. The protective group introduction is preferably effected by reacting the compound (XVII) with silylating agent. Examples of the silylating agent include t-butyldimethylchloride, t-butyldiphenylchloride, preferably t-butyldimethysilyl chloride. The silylating agent is used in an amount of about 1 to 5 moles per mole of the compound (XVII). This reaction is carried out in the presence of a base. The base is, for example, a tertiary amine such as triethylamine. The base is used in an amount of about 1 to 5 moles per mole of the compound (XVII). This reaction is generally carried out in a solvent. Examples of the solvent include ether, dioxane, tetrahydrofuran, dimethylformamide and dichlormethane. The reaction is generally carried out at a temperature of −30° C. to 100° C. The reaction time is about several minutes to about 24 hours.

Step 2 is a process in which the double bond of compound (XVIII) is hydroxylated to give the compound (XIX). For this hydroxylation, a mild oxidizing agent incapable of affecting the β-lactam ring and the amido group, such as osmic acid, osmic acid-N-methylmorpholine N-oxide, potassium permanganate or hydrogen peroxide-formic acid, preferably osmic acid-N-methylmorpholine N-oxide is used. The oxidizing agent is used in an amount of about 1 to 5 moles per mole of the compound (XVIII). The reaction is generally carried out in an inert gas atmosphere, such as argon or nitrogen. The reaction temperature is about −30° C. to 60° C. This reaction is generally carried out in a solvent. Examples of the solvent include t-butanol, acetone and dichloromethane. The reaction time is about several minutes to about 24 hours.

Step 3 is a process in which the diol compound (XIX) is oxidized with an oxidizing agent to the dialdehyde compound (XX). As the oxidizing agent, use is made of periodic acid, sodium periodate, lead tetraacetate or potassium permanganate, preferably periodic acid. The oxidizing agent is used in an amount of about 1 to 5 moles per mole of the compound (XIX), and the reaction is generally conducted in a solvent. Examples of the solvent include water, tetrahydrofuran, methanol and acetonitrile. The reaction temperature is about $-20°$ C. to $50°$ C. The reaction time is about 5 minutes to 24 hours. The compound (XX) thus formed may be isolated or the reaction mixture as it is may be used in the next reaction step.

Step 3' is a process in which the compound (XX) is directly produced by oxidation of the double bond of the compound (XVIII) with an oxidizing agent. As the oxidizing agent, use is made of for instance, ozone, potassium permanganate or chromyl trichloroacetate, preferably ozone. This oxidation reaction is generally conducted in a solvent. Examples of the solvent are methanol, ethanol, dichloromethane and ethyl acetate. The reaction is performed at a temperature of about $-80°$ C. to $10°$ C. The reaction time is several minutes to about 10 hours.

Step 4 is a process in which the compound (XXI) is produced from the compound (XX) by stereoselective ring closure reaction. The reaction is generally carried out in the presence of a catalyst. The catalyst usable in this reaction is preferably a combination of an organic acid and a secondary amine. The organic acid is, for example, acetic acid, trifluoroacetic acid, octanoic acid, p-toluenesulfonic acid or camphoric acid and the secondary amine is, for example, pyrrolidine, piperidine, morpholine or dibenzylamine. The acid and amine are combined in per se known manner. Furthermore, a compound containing both the functional groups (i.e. carboxyl and amino groups) in its molecule, such as proline, can also be used. A particularly preferred combination is, for example, the combination of dibenzylamine and trifluoroacetic acid. These catalysts are used in an amount of about 0.01 to 10 moles per mole of the compound (XX). This reaction is generally carried out in a solvent. Examples of the solvent include benzene, toluene, ether, methanol, tetrahydrofuran, dimethylformamide and hexamethylphosphoramide. The reaction temperature ranges from about $-10°$ C. to $120°$ C. and the reaction time is about 5 minutes to 24 hours. The compound (XXI) thus formed may be isolated or the reaction mixture as it is may be used in the next reaction step.

Step 5 is a process in which the compound (XXI) is reduced with a reducing agent to the compound (XXII). As the reducing agent, use is made of sodium borohydride, lithium borohydride, sodium cyanoborohydride or zinc borohydride, preferably sodium borohydride or lithium borohydride. The reducing agent is used in an amount of about 1 to 5 moles per mole of the compound (XXI). The reaction is generally carried out in a solvent. Examples of the solvent include methanol, ethanol, tetrahydrofuran or benzene. The reaction temperature is about $-50°$ C. to $50°$ C. The reaction time is about 10 minutes to 10 hours.

Step 6 is a process in which the compound (XXII) is converted to the compound (XXIII). The reaction is conducted in the same manner as step 12 in Chart 1. In particular, to produce the compound (XXIII) wherein Z is a chlorine or bromine atom, not only the halogenating agent mentioned hereinbefore, but also N-chlorosuccinimide-dimethyl sulfide and N-bromosuccinimide-dimethyl sulfide are used.

Step 7 is a process in which compound (XXIII) is oxidized with an oxidizing agent to the compound (XXIV). This reaction is carried out in the same manner as step 3' mentioned hereinbefore. The product (XXIV) as formed can also be used in the next reaction step without isolation thereof.

Step 8 is a process in which the compound (XXIV) is reduced with a reducing agent to the compound (XXV). The reaction can be carried out in the same manner as the reduction reaction in step 5 mentioned hereinbefore.

Step 9 is a process in which the protective group for the amido group of compound (XXV) is eliminated to give the compound (XXVI). The protective group can be eliminated by a per se known method. When the amido-protecting group is, for example, t-butyldimethylsilyl, the elimination reaction of protective group is effected by treatment, for example, with a fluoride compound such as tetra-n-butylammonium fluoride or potassium fluoride, or with an acid, such as hydrochloric acid, sulfuric acid, acetic acid or formic acid. As the solvent, use is made of tetrahydrofuran or dioxane. The reaction temperature ranges from about $0°$ C. to $60°$ C. and the reaction time is about 10 minutes to 24 hours.

Step 10 is a process in which the primary hydroxyl and amido groups of compound (XXVI) are protected to give the compound (XXVII). This protection reaction can be effected in the same manner as the production of compound (IV) mentioned hereinbefore, especially the production of compound (XVI).

Step 10' is a process in which the primary hydroxyl group of compound (XXV) is protected to give the compound (XXVII). As the protective group for hydroxyl group, use is made of those mentioned hereinbefore.

Step 11 is a process in which the compound (XXVII) is reacted with a mercaptan compound to give the compound (VIIa). This reaction is generally conducted in a solvent. Examples of the solvent include dimethylformamide, dichloromethane, acetamide or benzene. This reaction may be conducted in the presence of a base. As the base, use is made of sodium hydride or lithium hydride. The mercaptan compound is used in an amount of 1 to 2 moles per mole of the compound (XXVII).

Further, when dimethylformamide is employed as the solvent, an aqueous solution of sodium or potassium salt of the mercaptan compound can also be used. The mercaptan or the sodium or potassium salt of mercaptan is used in an amount of about 1 to 2 moles per mole of the compound (XXVII). The reaction temperature ranges from about $-10°$ C. to $60°$ C. The reaction time is about 10 minutes to 24 hours.

The starting compound (XVII) mentioned hereinbefore may be either in the racemic form or in the optically active form. When the compound (XVII) used is in the optically active form, the compound (VIIa) is obtained in the optically active form and therefore the objective compound (I) can be produced in the optically active form. The compound (XVII) in the optically active form is novel and can be produced, for example, by the process shown below (Chart 3) or a modification thereof.

Chart 3

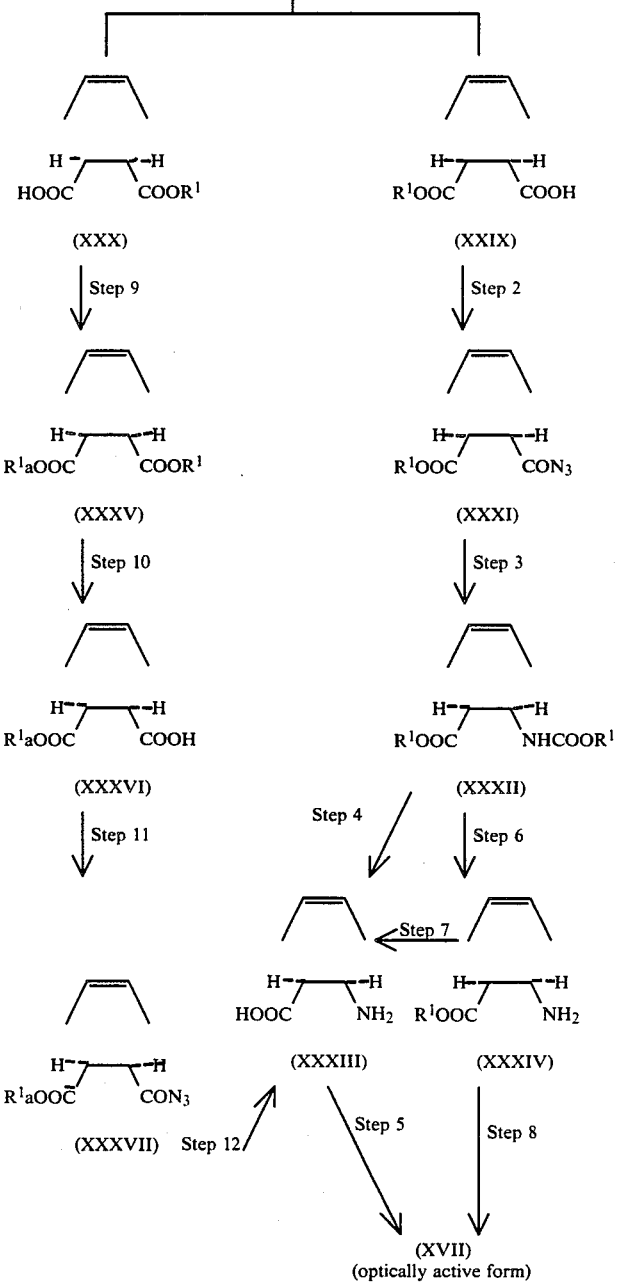

In the above formulas, $R^1$ and $R^{1a}$ each is a carboxyl-protecting group and has the same meaning as $R^1$ mentioned hereinbefore, provided that $R^1$ and $R^{1a}$ can not be the same simultaneously.

Referring to Chart 3, the starting material (XXVIII) can be produced by per se known method. For instance, the compound (XXVIII) wherein $R^1$ is methyl can be obtained by the method described in Chemical Abstracts, 49, 5328i (1955).

Step 1 is a process in which the compound (XXVIII) in the racemic form is subjected to optical resolution to give the enantiomers (XXIX) and (XXX). This optical resolution is conducted by a per se known method. For instance, the compound (XXVIII) in the racemic form is treated with an optical resolving agent to give diastereomer salts, followed by fractional crystallization, whereby one or both enantiomers can be recovered. As the optical resolving agent, use is made of cinchonidine, cinchonine, quinine, brucine, ephedrine, strychnine, morphine or L-arginine, preferably cinchonidine or cinchonine. The optical resolving agent is used in an amount of about ½ to 1 mole per mole of the compound (XXVIII). The solvent usable in fractional crystallization includes, among others methanol, ethanol, acetone, acetonitrile, dichloromethane, dioxane and tetrahydrofuran. The fractional crystallization is generally carried out at about −40° C. to 30° C. Either enantiomers can be converted to the desired compound (XVII) by the process shown in the Chart 3. Thus, for instance, the compound (XXIX) is converted to the compound (XXXI), which can then be converted to the compound (XXXII) by subjecting to the per se known Curtius reaction (Organic Reactions, 3, 337). On the other hand, the compound (XXX) is converted to the compound (XXXVI). Thereafter, the compound (XXXVI) can be converted to the compound (XXXIII) in the same manner as step 2→step 3→step 4 mentinoed above.

The preparation of the azides (XXXI) and (XXXVII) in step 2 and step 11 is carried out by reacting an active derivative prepared from the carboxylic acid (e.g. acid chloride, mixed acid anhydride) with sodium azide or diphenylphosphoryl azide. Such sodium azide or diphenylphosphoryl azide is used in an amount of about 1 to 3 moles per mole the compound (XXIX) or (XXXVI). The reaction is generally conducted in a solvent. Examples of the solvent include benzene, dioxane, dichloromethane and tetrahydrofuran. It is also preferable to react said compound with sodium azide, for example in a mixture of water and dichloromethane, in the presence of a phase transfer catalyst such as tetrabutylammonium hydrogen sulfate. The reaction temperature ranges from about −20° C. to 100° C. The reaction time is about 10 minutes to 10 hours.

Step 3 is a process in which the azido group of compound (XXXI) is subjected to Curtius rearrangement reaction to give the compound (XXXII). The rearrangement reaction is generally effected under heating in a solvent, preferably followed by addition of alcohols and a base such as triethylamine or triethylenediamine. The solvent is, for example, benzene, toluene or dichloroethane. The reaction temperature ranges from about 40° C. to 130° C. As alcohols, use is made of 2-methylsulfonylethanol, preferably.

Step 4 is a process in which the compound (XXXIII) is produced by eliminating the protective groups for the carboxyl group and the amino group of compound (XXXII). The elimination reaction of the protective group is performed by per se known method, e.g. the methods mentioned hereinbefore, preferably the one using an acid or alkali. The compound (XXXII) may also be converted to the compound (XXXIII) via the compound (XXXIV), for instance, by selective elimination reaction of the protective group.

Step 5 is a process in which the compound (XVII) is produced by ring closure reaction of the compound (XXXIII). The ring closure reaction is effected by heating the compound (XXXIII) in a solvent (e.g. acetonitrile), together with a combination of triphenylphosphine and 2,2′-dipyridyl disulfide or a combination of tri-n-butylphosphine and 2,2′-dipyridyl disulfide (each used in an amount of 1 to 2 equivalents per the compound (XXXIII). The reaction temperature ranges from about 60° C. to 150° C., and the reaction time is about 1 to 24 hours.

Step 8 is a process in which the compound (XVII) is produced by subjecting the compound (XXXIV) to ring closure reaction. The ring closure reaction is effected by reacting the compound (XXXIV) with a Grignard reagent. As the Grignard reagent, use is made of ethylmagnesium chloride, t-butylmagnesium chloride or phenylmagnesium chloride. The Grignard reagent is used in an amount of 1 to 5 moles per mole of the compound (XXXIV). The reaction is carried out in a solvent. Examples of the solvent include ether, dioxane or tetrahydrofuran. The reaction temperature is about −30° C. to 50° C. The reaction time is about 1 to 24 hours. Alternatively, the compound (XXXIV) can also be subjected to the reaction with the above Grignard reagent after protection with a silyl group such as trimethylsilyl.

Steps 9 and 10 indicate a method of enantio conversion. In cases where $R^1$ of the compound (XXX) is a methyl group, an alkali-stable group, such as a t-butyl group, is introduced, as $R^{1a}$, into the compound (XXXV) and then the compound (XXXV) is treated with an alkali to remove the group of $R^1$, whereby conversion to the compound (XXXVI) can be accomplished. The introduction of a t-butyl group is conducted by reacting the compound (XXX) with isobutene. This reaction is carried out in a solvent. Examples of the solvent include dichloromethane. This reaction is conducted in the presence of inorganic acid such as sulfuric acid. The reaction temperature is selected within the range of about −10° C. to 40° C. The reaction time is about 1 to 7 days.

Step 12 indicate that the compound (XXXVII) can be converted to the compound (XXXIII) in the same manner as the above-mentioned route (XXXI)→(XXXII)→(XXXIII).

The 3,4-trans compound (VIIb) in Chart 1 can also be produced by the following method or a modification thereof:

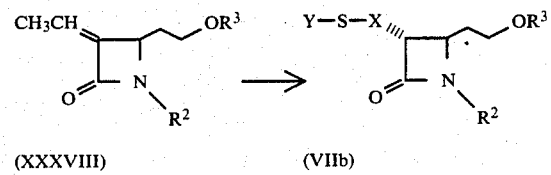

(XXXVIII)    (VIIb)

In the above formulas, $R^2$, $R^3$, X and Y are as defined hereinbefore.

The compound (XXXVIII) is known in the literature [B. G. Christensen et al., Journal of Organic Chemistry, 45, 1130 (1980)].

The compound (VIIb) is produced by addition reaction of a mercaptan compound to the double bond of compound (XXXVIII). This addition reaction is carried out in the same manner as the above-mentioned conversion of compound (XXVII) to compound (VIIa) in Chart 2.

The thus-obtained reaction product or a salt thereof can be isolated and purified by per se known methods, such as solvent extraction, pH adjustment, solvent transformation, crystallization, recrystallization and/or chromatography.

The invention is illustrated by following non-limiting examples.

In the Reference Examples and Examples, the symbols used respectively have the following meanings: s, singlet; d, doublet; dd, double doublet; ddd, double double doublet; t, triplet; q, quartet; ABq, AB pattern quartet; m, multiplet; J, coupling constant; b, broad.

The packings used in column chromatography in the Reference Examples and Examples are as follows: Florisil®, 100–200 mesh (Floridin Co., USA), Diaion HP 20® (Mitsubishi Chemical Industries Ltd., Japan), Amberlite XAD-2® (Rohm and Haas Co., USA) and silica gel (Kieselgel, 30–200 mesh®) (E. Merck, W. Germany).

Reference Example 1

7-(1-Hydroxy-3-thiacyclopentyl)-7-phenylthio-8-oxo-2,2-dimethyl-3-oxa-1-azabicyclo[4.2.0]octane In a nitrogen atmosphere at $-78°$ C., 15 ml of 15% n-butyl lithium/hexane is added to a solution of 3.4 ml of diisopropylamine in 30 ml of dry tetrahydrofuran. To the solution is added a solution of 1.55 g of 8-oxo-2,2-dimethyl-3-oxa-1-azabicyclo[4.2.0]octane in 10 ml of dry tetrahydrofuran over a period of 10 minutes and the mixture is stirred for 15 minutes. To the mixture is added a solution of 2.18 g of diphenyl disulfide in 10 ml of dry tetrahydrofuran over a period of 10 minutes and the mixture is stirred for 15 minutes, followed by addition of 2.04 g of 3-thiacyclopentanone over a period of 5 minutes and stirring for 30 minutes. The reaction mixture is poured into acetic acid (2 ml)-water (60 ml) with ice-cooling and the organic layer is separated, followed by extraction of the aqueous layer with ethyl acetate. The organic layers are combined, washed with 0.5N aqueous sodium hydroxide and water in that order and dried over $Na_2SO_4$, and the solvent is distilled off. The residue is subjected to silica gel column chromatography (hexane-ethyl acetate=3:1, 1:1) to give 3.03 g of the title compound as an oil.

$IR\nu_{max}^{Neat}$ cm$^{-1}$: 3450, 1740.

NMR(90 MHz, CDCl$_3$)δ: 1.40, 1.56(each 3H, s×2), 1.5–1.9(2H, m), 2.2–2.4(2H, m), 2.8–3.2(4H, m), 3.8–4.2(3H, m), 7.1–7.9(5H, m).

Reference Example 2

7-(1-Hydroxy-3-thiacyclopentyl)-8-oxo-2,2-dimethyl-3-oxa-1-azabicyclo[4.2.0]octane A solution of 3.03 g of 7-(1-hydroxy-3-thiacyclopentyl)-7-phenylthio-8-oxo-2,2-dimethyl-3-oxa-1-azabicyclo[4.2.0]octane as obtained in Reference Example 1, 300 mg of azobisisobutyronitrile and 8.5 ml of tri-n-butyltin hydride in 80 ml of acetone is refluxed in a nitrogen atmosphere. After 5 hours, an additional 5.0 ml of tri-n-butyltin hydride is added and the mixture is refluxed for 14 hours, followed by further addition of 4.0 ml of tri-n-butyltin hydride and refluxing for 5 hours. The solvent is then distilled off and the residue is treated with isopropyl ether to give 1.36 g of the title compound (6,7-cis isomer) as colorless crystals. The mother liquor is subjected to silica gel column chromatography (hexane-ethyl acetate=1:1) to give 348 mg of 6,7-cis form and 182 mg of 6,7-trans form of the title compound, each as colorless crystals.

6,7-cis form: m.p. 113°–115° C.

$IR\nu_{max}^{KBr}$ cm$^{-1}$: 3430, 1740.

NMR(90 MHz, CDCl$_3$)δ: 1.40, 1.74(each 3H, s×2), 1.6–2.2(2H, m), 2.5–3.2(6H, m), 3.36(1H, d, J=6 Hz), 3.7–4.1(3H, m).

Elemental analysis Calcd. for $C_{12}H_{19}NO_3S$ (%): C, 56.01; H, 7.44; N, 5.44 Found (%): C, 56.28; H, 7.35; N, 5.40.

6,7-trans form:

$IR\nu_{max}^{KBr}$ cm$^{-1}$: 3450, 1720.

NMR(90 MHz, CDCl$_3$)δ: 1.40, 1.69(each 3H, s×2), 1.6–2.0(2H, m), 2.3–3.2(7H, m), 3.5–4.0(3H, m).

Reference Example 3

6,7-cis-7-[1-(2-Methoxyethoxymethoxy)-3-thiacyclopentyl]-8-oxo-2,2-dimethyl-3-oxa-1-azabicyclo[4.2.0]octane To a solution of 370 mg of 6,7-cis-7-(1-hydroxy-3-thiacyclopentyl)-8-oxo-2,2-dimethyl-3-oxa-1-azabicyclo[4.2.0]octane as obtained in Reference Example 2 in 7 ml of dichloromethane are added 0.75 ml of diisopropylethylamine and 0.49 ml of 2-methoxyethoxymethyl chloride, and the mixture is allowed to stand at room temperature for 140 hours, then washed with water, 2% aqueous acetic acid and water in that order and dried over $Na_2SO_4$. The solvent is then distilled off to give the title compound as an oil.

$IR\nu_{max}^{Neat}$ cm$^{-1}$: 1745.

NMR(90 MHz, CDCl$_3$)δ: 1.38, 1.71(each 3H), 1.7(2H, m), 2.0–3.2(6H, m), 3.17(1H, d, J=5 Hz), 3.38(3H, s), 3.3–3.9(7H, m), 4.9(2H, bs).

Reference Example 4

6,7-cis-7-[1-(2-Methoxyethoxymethoxy)-3-thiacyclopentyl-3,3-dioxide]-8-oxo-2,2-dimethyl-3-oxa-1-azabicyclo-[4.2.0]octane 6,7-cis-7-[1-(2-Methoxyethoxymethoxy)-3-thiacyclopentyl]-8-oxo-2,2-dimethyl-3-oxa-1-azabicyclo[4.2.0]octane as obtained in Reference Example 3 is dissolved in 20 ml of dichloromethane and, with ice-cooling, 800 mg of m-chloroperbenzoic acid is added and the mixture is stirred for an hour. The reaction mixture is washed with saturated aqueous sodium hydrogen carbonate and water in that order and dried over $Na_2SO_4$ and the solvent is distilled off. The residue is subjected to silica gel column chromatography (ethyl acetate-chloroform=1:1 then ethyl acetate) to give 469 mg of the title compound as an oil.

$IR\nu_{max}^{Neat}$ cm$^{-1}$: 1750, 1320, 1120.

NMR(90 MHz, CDCl$_3$)δ: 1.38, 1.69(each 3H, s×2), 1.9(2H, m), 2.55(2H, m), 3.36(3H, s), 3.0–4.0(12H, m), 4.86(2H, s).

REFERENCE EXAMPLE 5

3,4-cis-4-Carboxymethyl-3-[1-(2-methoxyethoxymethoxy)-3-thiacyclopentyl-3,3-dioxido]azetidin-2-one With ice-cooling, 0.8 ml of Jones reagent is added to a solution of 540 mg of 6,7-cis-7-[1-(2-methoxyethoxymethoxy)-3-thiacyclopentyl-3,3-dioxido]-8-oxo-2,2-dimethyl-3-oxa-1-azabicyclo[4.2.0]octane as obtained in Reference Example 4 in 7 ml of acetone, and the mixture is stirred for 5 hours. To the reaction mixture is gradually added 0.5 ml of isopropanol, and the mixture is stirred for 10 minutes and diluted with 10 ml of dichloromethane. The insoluble matter is then filtered off with the aid of Celite and the filtrate is concentrated. To the residue is added 20 ml of chloroform and the mixture is dried over $MgSO_4$. The solvent is then distilled off to give 421 mg of the title compound as an oil.

$IR\nu_{max}^{Neat}$ cm$^{-1}$: 3500–2800, 1760–1730.

NMR(90 MHz, CDCl$_3$)δ: 2.4–4.0(13H, m), 3.36(3H, s), 4.15(1H, m), 4.8(2H, s), 7.2(1H, bs), 8.1(1H, bs).

REFERENCE EXAMPLE 6

3,4-cis-3-[1-(2-Methoxyethoxymethoxy)-3-thiacyclopentyl-3,3-dioxido]-4-[3-(4-nitrobenzyloxycarbonyl)-2-oxopropyl]azetidin-2-one To a solution of 421 mg of 3,4-cis-4-carboxymethyl-3-[1-(2-methoxyethoxymethoxy)-3-thiacyclopentyl-3,3-dioxido]azetidin-2-one as obtained in Reference Example 5 in 15 ml of dry tetrahydrofuran is added 236 mg of 1,1'-carbonyldiimidazole at room temperature, and the mixture is stirred for 6 hours. To this solution is added 759 mg of magnesium salt of mono-4-nitrobenzyl malonate and the mixture is stirred at room temperature for 17 hours. To the reaction mixture is added ethyl acetate and the mixture is washed with diluted hydrochloric acid, water, saturated aqueous sodium hydrogen carbonate and water in that order and dried over Na$_2$SO$_4$, followed by removal of the solvent by distillation. The residue is subjected to silica gel column chromatography (ethyl acetate-chloroform=1:1 then ethyl acetate) to give 448 mg of the title compound as a light-yellow oil.

IR$\nu_{max}^{Neat}$ cm$^{-1}$: 3320, 1750–1720, 1350, 1120.

NMR(90 MHz, CDCl$_3$)δ: 2.6(2H, m), 3.30(3H, s), 3.59(2H, s), 3.2–3.9(11H, m), 4.2(1H, m), 4.76(2H, s), 5.26(2H, s), 6.86(1H, bs), 7.55(2H, d, J=9 Hz), 8.22(2H, d, J=9 Hz).

REFERENCE EXAMPLE 7

3,4-cis-4-[3-Diazo-3-(4-nitrobenzyloxycarbonyl)-2-oxopropyl]-3-[1-(2-methoxyethoxymethoxy)-3-thiacyclopentyl-3,3-dioxido]azetidin-2-one To a solution of 470 mg of 3,4-cis-3-[1-(2-methoxyethoxymethoxy)-3-thiacyclopentyl-3,3-dioxido]-4-[3-(4-nitrobenzyloxycarbonyl)-2-oxopropyl]azetidin-2-one as obtained in Reference Example 6 in 14 ml of dry acetonitrile is added a solution of 203 mg of p-toluenesulfonylazide in 2 ml of dry acetonitrile at 0° C., followed by addition of 0.45 ml of triethylamine. The mixture is stirred at room temperature for an hour and then ethyl acetate is added. The mixture is washed with saturated aqueous sodium chloride and dried. The solvent is then distilled off and the residue is subjected to silica gel column chromatography (ethyl acetate) to give 442 mg of the title compound as a light-yellow frothy substance.

IR$\nu_{max}^{Neat}$ cm$^{-1}$: 3330, 2140, 1760, 1720, 1640, 1350, 1120.

NMR(90 MHz, CDCl$_3$)δ: 2.6(2H, m), 3.31(3H, s), 3.0–3.9(11H, m), 4.2(1H, m), 4.83(2H, bs), 5.36(2H, s), 6.40(1H, bs), 7.54(2H, d, J=9 Hz), 8.24(2H, d, J=9 Hz).

REFERENCE EXAMPLE 8

3,4-cis-4-[3-(Diazo-3-(4-nitrobenzyloxycarbonyl)-2-oxopropyl]-3-(1-hydroxy-3-thiacyclopentyl-3,3-dioxido)-azetidin-2-one In a nitrogen atmosphere at 0° C., 1.30 ml of titanium tetrachloride is added to a solution of 97 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 in 18 ml of dry dichloromethane and the mixture is stirred for an hour. To the reaction mixture is added 30 ml of ethyl acetate, and the mixture is further stirred for an hour and poured into 50 ml of 20% aqueous potassium carbonate. The insoluble matter is filtered off with the aid of Celite and the organic layer is separated. The aqueous layer is extracted with ethyl acetate. The organic layers are combined, washed with 20% potassium carbonate, water (three times), aqueous sodium hydrogen carbonate and water (three times) in that order, dried over Na$_2$SO$_4$ and concentrated to about 10 ml. And then, 10 ml of benzene is added and the solvent is distilled off to give 66 mg of the title compound in the benzene-solvated form, as a white frothy substance.

IR$\nu_{max}^{KBr}$ cm$^{-1}$: 3400, 2140, 1750, 1720, 1650.

NMR(90 MHz, acetone-d$_6$+CDCl$_3$)δ: 2.5(2H, m), 3.3–3.8(6H, m), 3.59(1H, d, J=6 Hz), 4.4(1H, m), 5.51(2H, s), 6.79(1H, bs), 7.46(s, peak due to the solvent benzene), 7.71(2H, d, J=9 Hz), 8.38(2H, d, J=9 Hz).

REFERENCE EXAMPLE 9

7-(1-Hydroxy-4-thiacyclohexyl)-7-phenylthio-8-oxo-2,2-dimethyl-3-oxa-1-azabicyclo[4.2.0]octane Using 620 mg of 8-oxo-2,2-dimethyl-3-oxa-1-azabicyclo[4.2.0]octane, 960 mg of diphenyl disulfide and 511 mg of 4-thiacyclohexanone and following the procedure of Reference Example 1, 1.192 g of the title compound is obtained as colorless crystals.

m.p. 191°–192° C.

IR$\nu_{max}^{KBr}$ cm$^{-1}$: 3500, 1730.

NMR(90 MHz, CDCl$_3$)δ: 1.38, 1.48(each 3H, s×2), 1.6(2H, m), 1.7–3.3(8H, m), 3.7–4.2(3H, m), 7.1–7.9(5H, m).

Elememtal analysis Calcd. for C$_{19}$H$_{25}$NO$_3$S$_2$(%): C, 60.13; H, 6.64; N, 3.69; S, 16.89 Found (%): C, 60.39; H, 6.49; N, 3.68; S, 17.17.

REFERENCE EXAMPLE 10

7-(1-Hydroxy-4-thiacyclohexyl)-8-oxo-2,2-dimethyl-3-oxa-1-azabicyclo[4.2.0]octane Using 1.192 g of 7-(1-hydroxy-4-thiacyclohexyl)-7-phenylthio-8-oxo-2,2-dimethyl-3-oxa-1-azabicyclo[4.2.0]octane as obtained in Reference Example 9, the procedure of Reference Example 2 is followed to give 6,7-cis form (542 mg) and 6,7-trans form (222 mg) of the title compound each as colorless crystals.

6,7-cis form.

m.p. 133°–134° C.

IR$\nu_{max}^{KBr}$ cm$^{-1}$: 3400, 1740.

NMR(90 MHz, CDCl$_3$)δ: 1.38, 1.73(each 3H, s×2), 1.6–3.3(10H, m), 3.20(1H, d, J=6 Hz), 3.6–3.9(3H, m).

Elemental analysis Calcd. for C$_{13}$H$_{21}$NO$_3$S (%): C, 57.54; H, 7.80; N, 5.16; S, 11.81 Found (%): C, 57.30; H, 7.85; N, 5.42; S, 12.05.

6,7-trans form.

IR$\nu_{max}^{KBr}$ cm$^{-1}$: 3500, 1720.

NMR(90 MHz, CDCl$_3$)δ: 1.40, 1.71(each 3H, s×2), 1.6–3.3(10H, m), 2.81(1H, d, J=2 Hz), 3.55(1H, m), 3.7–3.9(2H, m).

REFERENCE EXAMPLE 11

6,7-cis-7-[1-(2-Methoxyethoxymethoxy)-4-thiacyclohexyl]-8-oxo-2,2-dimethyl-3-oxa-1-azabicyclo[4.2.0]octane Using 6,7-cis-7-(1-hydroxy-4-thiacyclohexyl)-8-oxo-2,2-dimethyl-3-oxa-1-azabicyclo[4.2.0]octane as obtained in Reference Example 10 and following the procedure of Reference Example 3, the title compound is obtained.

IR$\nu_{max}^{Neat}$ cm$^{-1}$: 1745.

NMR(90 MHz, CDCl$_3$)δ: 1.38, 1.71(each 3H, s×2), 1.5–3.1(10H, m), 3.38(3H, s), 3.0–4.0(8H, m), 4.93(2H, s).

REFERENCE EXAMPLE 12

6,7-cis-7-[1-(2-Methoxyethoxymethoxy)-4-thiacyclohexyl-4,4-dioxido]-8-oxo-2,2-dimethyl-3-oxa-1-azabicyclo-[4.2.0]octane Using 6,7-cis-7-[1-(2-methoxyethoxymethoxy)-4-thiacyclohexyl]-8-oxo-2,2-dimethyl-3-oxa-1-azabicyclo-[4.2.0]octane and following the procedure of Reference Example 4, 780 mg of the title compound is obtained as an oil.

IRν$_{max}^{Neat}$ cm$^{-1}$: 1740, 1315, 1130.

NMR(90 MHz, CDCl$_3$)δ: 1.38, 1.70(each 3H, s×2), 1.6–3.0(8H, m), 3.1–4.0(10H, m), 3.36(3H, s), 5.01(2H, s).

REFERENCE EXAMPLE 13

3,4-cis-4-Carboxymethyl-3-[1-(2-methoxyethoxymethoxy)-4-thiacyclohexyl-4,4-dioxido]azetidin-2-one Using 472 mg of 6,7-cis-7-[1-(2-methoxyethoxymethoxy)-4-thiacyclohexyl-4,4-dioxido]-8-oxo-2,2-dimethyl-3-oxa-1-azabicyclo[4.2.0]octane and following the procedure of Reference Example 5, 362 mg of the title compound is obtained as an oil.

REFERENCE EXAMPLE 14

3,4-cis-3-[1-(2-Methoxyethoxymethoxy)-4-thiacyclohexyl-4,4-dioxido]-4-[3-(4-nitrobenzyloxycarbonyl)-2-oxopropyl]azetidin-2-one Using 362 mg of 3,4-cis-4-carboxymethyl-3-[1-(2-methoxyethoxymethoxy)-4-thiacyclohexyl-4,4-dioxido]-azetidin-2-one and following the procedure of Reference Example 6, 324 mg of the title compound is obtained as a light-yellow oil.

IRν$_{max}^{Neat}$ cm$^{-1}$: 3320, 1750–1720, 1350, 1120.

NMR(90 MHz, CDCl$_3$)δ: 2.0–3.0(6H, m), 3.34(3H, s), 3.63(2H, s), 3.1–3.9(9H, m), 4.2(1H, m), 4.92(2H, s), 5.30(2H, s), 6.5(1H, b), 7.54(2H, d, J=9 Hz), 8.23(2H, d, J=9 Hz).

REFERENCE EXAMPLE 15

3,4-cis-4-[3-Diazo-3-(4-nitrobenzyloxycarbonyl)-2-oxopropyl]-3-[1-(2-methoxyethoxymethoxy)-4-thiacyclohexyl-4,4-dioxido]azetidin-2-one Using 704 mg of 3,4-cis-3-[1-(2-methoxyethoxymethoxy)-4-thiacyclohexyl-4,4-dioxido]-4-[3-(4-nitrobenzyloxycarbonyl)-2-oxopropyl]azetidin-2-one and following the procedure of Reference Example 7, 724 mg of the title compound is obtained as a light-yellow frothy substance.

IRν$_{max}^{Neat}$ cm$^{-1}$: 3320, 2140, 1760, 1720, 1650, 1350, 1120.

NMR(90 MHz, CDCl$_3$)δ: 2.1–3.0(6H, m), 3.36(3H, s), 3.3–3.9(9H, m), 4.2(1H, m), 4.93(2H, s), 5.38(2H, s), 6.4(1H, bs), 7.54(2H, d, J=9 Hz), 8.26(2H, d, J=9 Hz).

REFERENCE EXAMPLE 16

6,7-trans-7-(1-Hydroxy-2-methylthioethyl)-8-oxo-2,2-dimethyl-3-oxa-1-azabicyclo[4.2.0]octane In a nitrogen atmosphere at −78° C., 3.0 ml of 15% n-butyl lithium/hexane is added to a solution of 0.68 ml of diisopropylamine in 10 ml of dry tetrahydrofuran. To the mixture is added a solution of 310 mg of 8-oxo-2,2-dimethyl-3-oxa-1-azabicyclo[4.2.0octane in 1 ml of dry tetrahydrofuran over a period of 5 minutes, and the mixture is stirred for 10 minutes. To this mixture is added 360 mg of methylthioacetaldehyde over a period of 5 minutes and the resulting mixture is stirred for 30 minutes, followed by addition of aqueous saturated ammonium chloride. The temperature of the mixture is returned to room temperature. The organic layer is separated and the aqueous layer is extracted with ethyl acetate. The organic layers are combined, washed with 0.5N aqueous sodium hydroxide and water in that order and dried over Na$_2$SO$_4$, followed by removal of the solvent by distillation. The residue is subjected to silica gel column chromatography (hexane-ethyl acetate=1:1 to 1:2) to give a mixture (263 mg) of two stereoisomeric forms A and B of the title compound, which depend on the configuration of the hydroxyl group on the 7-position substituent, and one stereoisomeric form A (211 mg), each as an oil. Hereinafter, such two stereoisomers resulting from the two possible configurations of the hydroxyl group (or protected hydroxyl group) on said substituent are referred to as isomer A and isomer B.

Mixture of isomers A and B:

IRν$_{max}^{Neat}$ cm$^{-1}$: 3440, 1730.

NMR(90 MHz, CDCl$_3$)δ: 1.45, 1.78(each 3H, s×2), 1.5–2.1(2H, m), 2.18(3H, s), 2.6–3.2(3H, m), 3.6(1H, m), 3.7–4.0(2H, m), 4.1(1H, m).

Isomer A:

IRν$_{max}^{Neat}$ cm$^{-1}$: 3440, 1730.

NMR(90 MHz, CDCl$_3$)δ: 1.40, 1.73(each 3H, s×2), 1.5–2.1(2H, m), 2.12(3H, s), 2.6–3.2(3H, m), 3.6(1H, m), 3.7–4.0(2H, m), 4.0(1H, m).

REFERENCE EXAMPLE 17

6,7-trans-7-[1-(2-Methoxyethoxymethoxy)-2-methylthioethyl]-8-oxo-2,2-dimethyl-3-oxa-1-azabicyclo[4.2.0]octane (isomer A)

Using 211 mg of 6,7-trans-7-(1-hydroxy-2-methylthioethyl)-8-oxo-2,2-dimethyl-3-oxa-1-azabicyclo[4.2.0]octane (isomer A) and following the procedure of Reference Example 3, the title compound is obtained as an oil.

IRν$_{max}^{Neat}$ cm$^{-1}$: 1750.

NMR(90 MHz, CDCl$_3$)δ: 1.40, 1.73(each 3H, s×2), 1.6–2.1(2H, m), 2.15(3H, s), 2.79(2H, d, J=6 Hz), 3.38(3H, s), 3.1–4.3(9H, m), 4.79(2H, s).

REFERENCE EXAMPLE 18

6,7-trans-7-[1-(2-Methoxyethoxymethoxy)-2-methylsulfonylethyl]-8-oxo-2,2-dimethyl-3-oxa-1-azabicyclo[4.2.0]octane (isomer A)

Using 6,7-trans-7-[1-(2-methoxyethoxymethoxy)-2-methylthioethyl]-8-oxo-2,2-dimethyl-3-oxa-1-azabicyclo[4.2.0]octane as obtained in Reference Example 17 and following the procedure of Reference Example 4, 259 mg of the title compound is obtained as an oil.

IRν$_{max}^{Neat}$ cm$^{-1}$: 1745.

NMR(90 MHz, CDCl$_3$)δ: 1.40, 1.71(each 3H, s×2), 1.6–2.1(2H, m), 3.03(3H, s), 3.36(3H, s), 3.1–4.0(10H, m), 4.45(1H, m), 4.86(2H, m).

REFERENCE EXAMPLE 19

3,4-trans-4-Carboxymethyl-3-[1-(2-methoxyethoxymethoxy)-2-methylsulfonylethyl]azetidin-2-one (isomer A)

Using 259 mg of 6,7-trans-7-[1-(2-methoxyethoxymethoxy)-2-methylsulfonylethyl]-8-oxo-2,2-dimethyl-3-oxa-1-azabicyclo[4.2.0]octane and following the procedure of Reference Example 5, 190 mg of the title compound is obtained as an oil.

IR$\nu_{max}^{Neat}$ cm$^{-1}$: 3500–2800, 1760–1700.

NMR(90 MHz, CDCl$_3$)δ: 3.00(3H, s), 3.36(3H, s), 2.6–4.2(10H, m), 4.5(1H, m), 4.88(2H, s), 7.0(1H, bs), 7.5(1H, bs).

REFERENCE EXAMPLE 20

3,4-trans-3-[1-(2-Methoxyethoxymethoxy)-2-methylsulfonylethyl]-4-[3-(4-nitrobenzyloxycarbonyl)-2-oxopropyl]-azetidin-2-one (isomer A)

Using 190 mg of 3,4-trans-4-carboxymethyl-3-[1-(2-methoxyethoxymethoxy)-2-methylsulfonylethyl]azetidin-2-one and following the procedure of Reference Example 6, 158 mg of the title compound is obtained as a light-yellow oil.

IR$\nu_{max}^{Neat}$ cm$^{-1}$: 3320, 1760–1715, 1350, 1130.

NMR(90 MHz, CDCl$_3$)δ: 2.96(3H, s), 3.0(2H, m), 3.35(3H, s), 3.56(2H, s), 3.1–3.8(7H, m), 4.0(1H, m), 4.45(1H, m), 4.87(2H, s), 5.26(2H, s), 6.25(1H, bs), 7.48(2H, d, J=9 Hz), 8.21(2H, d, J=9 Hz).

REFERENCE EXAMPLE 21

3,4-trans-4-[3-Diazo-3-(4-nitrobenzyloxycarbonyl)-2-oxopropyl]-3-[1-(2-methoxyethoxymethoxy)-2-methylsulfonylethyl]azetidin-2-one (isomer A)

Using 158 mg of 3,4-trans-3-[1-(2-methoxyethoxymethoxy)-2-methylsulfonylethyl]-4-[3-(4-nitrobenzyloxycarbonyl)-2-oxopropyl]azetidin-2-one and following the procedure of Reference Example 7, 148 mg of the title compound is obtained as a light-yellow oil.

IR$\nu_{max}^{Neat}$ cm$^{-1}$: 3350, 2140, 1760, 1720, 1640, 1350, 1120.

NMR(90 MHz, CDCl$_3$)δ: 2.97(3H, s), 2.9–3.3(3H, m), 3.33(3H, s), 3.3–3.8(6H, m), 4.0(1H, m), 4.5(1H, m), 4.86(2H, s), 5.34(2H, s), 6.3(1H, bs), 7.52(2H, d), 8.23(2H, d, J=9 Hz).

REFERENCE EXAMPLE 22

6,7-trans-7-[1-(2-Methoxyethoxymethoxy)-2-methylthioethyl]-8-oxo-2,2-dimethyl-3-oxa-1-azabicyclo[4.2.0]octane (mixture of isomers A and B)

Using 263 mg of 6,7-trans-7-(1-hydroxy-2-methylthioethyl)-8-oxo-2,2-dimethyl-3-oxa-1-azabicyclo[4.2.0]octane (mixture of isomers A and B) as obtained in Reference Example 16 and following the procedure of Reference Example 3, the title compound is obtained as an oil.

The IR and NMR spectra of the above compound are identical with those of the compound obtained in Reference Example 17.

REFERENCE EXAMPLE 23

6,7-trans-7-[1-(2-methoxyethoxymethoxy)-2-methylsulfonylethyl]-8-oxo-2,2-dimethyl-3-oxa-1-azabicyclo[4.2.0]octane (mixture of isomers A and B)

Using 6,7-trans-7-[1-(2-methoxyethoxymethoxy)-2-methylthioethyl]-8-oxo-2,2-dimethyl-3-oxa-1-azabicyclo-[4.2.0]octane as obtained in Reference Example 22 and following the procedure of Reference Example 4, 303 mg of the title compound is obtained as an oil.

IR$\nu_{max}^{Neat}$ cm$^{-1}$: 1745.

NMR(90 MHz, CDCl$_3$)δ: 1.40, 1.71(each 3H, s×2), 1.6–2.1(2H, m), 2.97(3H, s), 3.36(3H, s), 3.1–4.0(10H, m), 4.45(1H, m), 4.86(2H, s).

Reference Example 24

3,4-trans-4-Carboxymethyl-3-[1-(2-methoxyethoxymethoxy)-2-methylsulfonylethyl]azetidin-2-one (mixture of isomers A and B)

Using 303 mg of 6,7-trans-7-[1-(2-methoxyethoxymethoxy)-2-methylsulfonylethyl]-8-oxo-2,2-dimethyl-3-oxa-1-azabicyclo[4.2.0]octane and following the procedure of Reference Example 5, 233 mg of the title compound is obtained as an oil.

Reference Example 25

3,4-trans-3-[1-(2-Methoxyethoxymethoxy)-2-methylsulfonylethyl]-4-[3-(4-nitrobenzyloxycarbonyl)-2-oxopropyl]-azetidin-2-one (mixture of isomers A and B)

Using 233 mg of 3,4-trans-4-carboxymethyl-3-[1-(2-methoxyethoxymethoxy)-2-methylsulfonylethyl]azetidin-2-one and following the procedure of Reference Example 6, 181 mg of the title compound is obtained as a light-yellow oil.

IR$\nu_{max}^{Neat}$ cm$^{-1}$: 3330, 1760–1710, 1350, 1120.

NMR(90 MHz, CDCl$_3$)δ: 2.97(3H, s), 2.8–3.3(3H, m), 3.33(3H, s), 3.56(2H, s), 3.3–3.9(6H, m), 4.0(1H, m), 4.40(1H, m), 4.86(2H, s), 5.25(2H, s), 63(1H, bs), 7.51(2H, d, J=9 Hz), 8.21(2H, d, J=9 Hz).

Reference Example 26

3,4-trans-4-[3-Diazo-3-(4-nitrobenzyloxycarbonyl)-2-oxopropyl]-3-[1-(2-methoxyethoxymethoxy)-2-methylsulfonylethyl]azetidin-2-one (mixture of isomers A and B)

Using 181 mg of 3,4-trans-3-[1-(2-methoxyethoxymethoxy)-2-methylsulfonylethyl]-4-[3-(4-nitrobenzyloxycarbonyl)-2-oxopropyl]azetidin-2-one and following the procedure of Reference Example 7, 166 mg of the title compound is obtained as a light-yellow oil.

IR$\nu_{max}^{Neat}$ cm$^{-1}$: 3330, 2140, 1760, 1720, 1650, 1340, 1130.

NMR(90 MHz, CDCl$_3$)δ: 2.97(3H, s), 2.8–3.3(3H, m), 3.35(3H, s), 3.3–3.9(6H, m), 4.05(1H, m), 4.46(1H, m), 4.87(2H, s), 5.35(2H, s), 6.2(1H, bs), 7.51(2H, d, J=9 Hz), 8.24(2H, d, J=9 Hz).

Reference Example 27

6,7-trans-7-(2-Methylthioacetyl)-8-oxo-2,2-dimethyl-3-oxa-1-azabicyclo[4.2.0]octane Under a nitrogen atmosphere at −78° C., 0.24 ml of dimethyl sulfoxide is dissolved in 5 ml of dichloromethane, and a solution of 0.36 ml of dry trifluoroacetic acid in 1 ml of dichloromethane is added to the solution, followed by stirring for 10 minutes. And then, a solution of 420 mg of 6,7-trans-7-(1-hydroxy-2-methylthioethyl)-8-oxo-2,2-dimethyl-3-oxa-1-azabicyclo[4.2.0]octane (mixture of isomers A and B) as obtained in Reference Example 16 in 2 ml of dichloromethane is added over a period of 10 minutes. The mixture is stirred for 30 minutes and 0.68 ml of triethylamine is added over a period of 10 minutes, followed by stirring at room temperature for 1.5 hours. The reaction mixture is poured into water, extracted with dichloromethane, washed with water and dried over Na$_2$SO$_4$. The solvent is then distilled off and the residue is subjected to silica gel column chromatography (hexane-ethyl acetate=3:1) to give the title compound (331 mg) as an oil.

IR$\nu_{max}^{Neat}$ cm$^{-1}$: 1750, 1700.

NMR(90 MHz, CDCl₃)δ: 1.40, 1.69(each 3H, s×2), 2.07(3H, s), 1.5–2.0(2H, m), 3.33(2H, ABq, J=19.8, 13.8 Hz), 3.7–4.2(3H, m) 4.25(1H, d, J=2.5 Hz).

Reference Example 28

6,7-trans-7-(1-Hydroxy-2-methylthioethyl)-8-oxo-2,2-dimethyl-3-oxa-1-azabicyclo[4.2.0]octane (isomer B)

Under a nitrogen atmosphere at room temperature, 343 mg of potassium iodide and 4.9 ml of 1M potassium tri-sec-butyl borohydride-tetrahydrofuran solution are added to a solution of 429 mg of 6,7-trans-7-(2-methylthioacetyl)-8-oxo-2,2-dimethyl-3-oxa-1-azabicyclo[4.2.0]octane in 23 ml of dry diethyl ether, and the mixture is stirred for 30 minutes. To the mixture is added 2.0 ml of 1M potassium tri-sec-butyl borohydride-tetrahydrofuran solution, and the resulting mixture is stirred for an hour, followed by further addition of 2.0 ml of the above tetrahydrofuran solution. The mixture is stirred for 2 hours and 0.49 ml of acetic acid and 10 ml of ethyl acetate are added. The insoluble matter is filtered off and the solvent is distilled off, followed by addition of 20 ml of ethyl acetate. The organic layer is washed with aqueous sodium hydrogen carbonate and water in that order and dried over Na₂SO₄. The solvent is then distilled off and the residue is subjected to silica gel column chromatography (ethyl acetate-hexane=1:2 to 2:1) to give the title compound (330 mg) as colorless prisms.

m.p. 106°–107° C.

IR$\nu_{max}^{KBr}$ cm⁻¹: 3500, 1740.

NMR(90 MHz, CDCl₃)δ: 1.40, 1.71(each 3H, s×2), 2.12(3H, s), 1.5–2.1(2H, m), 2.3–3.2(3H, m), 3.5–4.2(4H, m).

Elemental analysis Calcd. for C₁₁H₁₉NO₃S (%): C, 53.85; H, 7.81; N, 5.71; S, 13.07 Found (%): C, 54.03; H, 7.92; N, 5.70; S, 12.77.

Reference Example 29

6,7-trans-7-[1-(2-Methoxyethoxymethoxy)-2-methylthioethyl]-8-oxo-2,2-dimethyl-3-oxa-1-azabicyclo[4.2.0]octane (isomer B)

Using 444 mg of 6,7-trans-7-(1-hydroxy-2-methylthioethyl)-8-oxo-2,2-dimethyl-3-oxa-1-azabicyclo[4.2.0]octane (isomer B) as obtained in Reference Example 28 and following the procedure of Reference Example 3, the title compound is obtained as an oil.

IR$\nu_{max}^{Neat}$ cm⁻¹: 1750.

NMR(90 MHz, CDCl₃)δ: 1.40, 1.71(each 3H, s×2), 1.6–2.1(2H, m), 2.76(2H, d, J=6 Hz), 3.38 (3H, s), 3.1–4.3(9H, m), 4.8(2H, s).

Reference Example 30

6,7-trans-7-[1-(2-Methoxyethoxymethoxy)-2-methylsulfonylethyl]-8-oxo-2,2-dimethyl-3-oxa-1-azabicyclo[4.2.0]octane (isomer B)

Using 6,7-trans-7-[1-(2-methoxyethoxymethoxy)-2-methylthioethyl]-8-oxo-2,2-dimethyl-3-oxa-1-azabicyclo[4.2.0]octane as obtained in Reference Example 29 and following the procedure of Reference Example 4, 507 mg of the title compound is obtained as an oil.

IR$\nu_{max}^{Neat}$ cm⁻¹: 1750, 1350, 1140.

NMR(90 MHz, CDCl₃)δ: 1.40, 1.70(each 3H, s×2), 1.6–2.1(2H, m), 2.96(3H, s), 3.08(1H, dd, J=1.5, 7.5 Hz), 3.36(3H, s), 3.3–4.0(9H, m), 4.44(1H, ddd, J=7.5, 7.5, 4.5 Hz), 4.83(2H, s).

Reference Example 31

3,4-trans-4-Carboxymethyl-3-[1-(2-methoxyethoxymethoxy)-2-methylsulfonylethyl]azetidin-2-one (isomer B)

Using 207 mg of 6,7-trans-7-[1-(2-methoxyethoxymethoxy)-2-methylsulfonylethyl]-8-oxo-2,2-dimethyl-3-oxa-1-azabicyclo[4.2.0]octane as obtained in Reference Example 30 and following the procedure of Reference Example 5, 192 mg of the title compound is obtained as an oil.

IR$\nu_{max}^{Neat}$ cm⁻¹: 3500–2800, 1760–1700.

NMR(90 MHz, CDCl₃)δ: 3.00(3H, s), 3.36(3H, s), 2.6–3.9(9H, m), 4.05(1H, m), 4.52(1H, m), 5.82(2H, bs), 7.0(1H, bs), 7.5(1H, bs).

Reference Example 32

3,4-trans-3-[1-(2-Methoxyethoxymethoxy)-2-methylsulfonylethyl]-4-[3-(4-nitrobenzyloxycarbonyl)-2-oxopropyl]azetidin-2-one (isomer B)

Using 192 mg of 3,4-trans-4-carboxymethyl-3-[1-(2-methoxyethoxymethoxy)-2-methylsulfonylethyl]azetidin-2-one as obtained in Reference Example 31 and following the procedure of Reference Example 6, 142 mg of the title compound is obtained as an oil.

IR$\nu_{max}^{Neat}$ cm⁻¹: 3440, 1760–1720, 1350, 1140.

NMR(90 MHz, CDCl₃)δ: 2.94(3H, s), 2.7–3.3(3H, m), 3.33(3H, s), 3.56(2H, s),3.3–3.8(6H, m), 4.1(1H, m), 4.5(1H, m), 4.80(2H, s), 5.26(2H, s), 6.25(1H, s), 7.51(2H, d, J=9 Hz), 8.21(2H, d, J=9 Hz).

Reference Example 33

3,4-trans-4-[3-Diazo-3-(4-nitrobenzyloxycarbonyl)-2-oxopropyl]-3-[1-(2-methoxyethoxymethoxy)-2-methylsulfonylethyl]azetidin-2-one (isomer B)

Using 311 mg of 3,4-trans-3-[1-(2-methoxyethoxymethoxy)-2-methylsulfonylethyl]-4-[3-(4-nitrobenzyloxycarbonyl)-2-oxopropyl]azetidin-2-one as obtained in Reference Example 32 and following the procedure of Reference Example 7, 284 mg of the title compound is obtained as an oil.

IR$\nu_{max}^{Neat}$ cm⁻¹: 3440, 2140, 1760, 1720, 1640, 1350, 1130.

NMR(90 MHz, CDCl₃)δ: 3.96(3H, s), 2.8–3.4(3H, m), 3.33(3H, s), 3.3–3.8(6H, m), 4.1(1H, m), 4.5(1H, m), 4.81(2H, s), 5.36(2H, s), 6.39(1H, s), 7.53(2H, d, J=9 Hz), 8.23(2H, d, J=9 Hz).

Reference Example 34

7-(1-Hydroxy-2-methylthioethyl)-7-phenylthio-8-oxo-2,2-dimethyl-3-oxa-1-azabicyclo[4.2.0]octane Using 1.00 g of 8-oxo-2,2-dimethyl-3-oxa-1-azabicyclo[4.2.0]octane and following the procedure of Reference Example 1, 1.88 g of the title compound is obtained as colorless crystals. (Although the major product obtained is a mixture of isomers A and B, individual isomers may be isolated in very small amounts.)

m.p. 83°–85° C. (mixture of isomers A and B).

IR$\nu_{max}^{KBr}$ cm⁻¹: 3500, 1730 (mixture of isomers A and B).

NMR(90 MHz, CDCl₃)δ: Isomer A: 0.79, 1.58(each 3H, s×2), 1.6–2.0(2H, m), 2.15(3H, s), 2.89(2H, d, J=7.5 Hz), 3.3–4.0(3H, m), 4.31(1H, dd, J=7.5, 4.8 Hz), 7.2–7.6(5H, m) Isomer B: 1.47, 1.76(each 3H, s×2), 1.91(3H, s), 1.6–2.0(2H, m), 2.96(2H, m), 3.7–4.0(3H, m), 4.13(1H, dd, J=10.5, 5.1 Hz), 7.2–7.7(5H, m).

Elemental analysis Calcd. for $C_{17}H_{23}NO_3S_2$ (mixture of isomers A and B) (%): C, 57.76; H, 6.56; N, 3.96; S, 18.14 Found (%): C, 57.69; H, 6.68; N, 4.14; S, 18.38.

Reference Example 35

6,7-cis-7-(1-Hydroxy-2-methylthioethyl)-8-oxo-2,2-dimethyl-3-oxa-1-azabicyclo[4.2.0]octane Using 1.32 g of 7-(1-hydroxy-2-methylthioethyl)-7-phenylthio-8-oxo-2,2-dimethyl-3-oxa-1-azabicyclo-[4.2.0]octane as obtained in Reference Example 34 and following the procedure of Reference Example 2, 560 mg of the title compound is obtained as colorless crystals. There are further obtained 165 mg of mixture of 6,7-cis and trans isomers, and 89 mg of 6,7-trans isomer.

m.p. 91°–92.5° C.
$IR\nu_{max}^{KBr}$ cm$^{-1}$: 3420, 1720.
NMR(90 MHz, CDCl$_3$)δ: 1.38, 1.72(each 3H, s×2), 2.15(3H, s), 1.5–2.2(2H, m), 2.68(2H, d, J=6 Hz), 3.33(1H, dd, J=6.8, 5.3 Hz), 3.6–4.0(3H, m), 4.12(1H, m).

Elemental analysis Calcd. for $C_{11}H_{19}NO_3S$ (%): C, 53.85; H, 7.81; N, 5.71; S, 13.07 Found (%): C, 53.85; H, 7.81; N, 5.82; S, 13.06.

The IR and NMR spectra of the 5,6-trans isomer thus obtained are identical with those of the compound obtained in Reference Example 16.

Reference Example 36

6,7-cis-7-[1-(2-Methoxyethoxymethoxy)-2-methylthioethyl]-8-oxo-2,2-dimethyl-3-oxa-1-azabicyclo[4.2.0]octane Using 274 mg of 6,7-cis-7-(1-hydroxy-2-methylthioethyl)-8-oxo-2,2-dimethyl-3-oxa-1-azabicyclo[4.2.0]octane as obtained in Reference Example 35 and following the procedure of Reference Example 3, the title compound is obtained as an oil.

$IR\nu_{max}^{Neat}$ cm$^{-1}$: 1750.
NMR(90 MHz, CDCl$_3$)δ: 1.37, 1.70(each 3H, s×2), 2.14(3H, s), 1.5–2.1(2H, m), 2.75(2H, dd, J=5.3, 5.3 Hz), 3.38(3H, s), 3.4–4.0(8H, m), 4.2(1H, m), 4.87(2H, m).

Reference Example 37

6,7-cis-7-[1-(2-Methoxyethoxymethoxy)-2-methylsulfonylethyl]-8-oxo-2,2-dimethyl-3-oxa-1-azabicyclo[4.2.0]octane Using 6,7-cis-7-[1-(2-methoxyethoxymethoxy)-2-methylthioethyl]-8-oxo-2,2-dimethyl-3-oxa-1-azabicyclo[4.2.0]octane as obtained in Reference Example 36 and following the procedure of Reference Example 4, 310 mg of the title compound is obtained as an oil.

$IR\nu_{max}^{Neat}$ cm$^{-1}$: 1745, 1350, 1130.
NMR(90 MHz, CDCl$_3$)δ: 1.36, 1.69(each 3H, s), 1.5–2.2(2H, m), 3.01(3H, s), 3.36(3H, s), 3.1–4.0(10H, m), 4.5(1H, m), 4.90(2H, ABq, J=6, 12 Hz).

Reference Example 38

3,4-cis-4-Carboxymethyl-3-[1-(2-methoxyethoxymethoxy)-2-methylsulfonylethyl]azetidin-2-one Using 266 mg of 6,7-cis-7-[1-(2-methoxyethoxymethoxy)-2-methysulfonylethyl]-8-oxo-2,2-dimethyl-3-oxa-1-azabicyclo[4.2.0]octane as obtained in Reference Example 37 and following the procedure of Reference Example 5, 205 mg of the title compound is obtained as an oil.

$IR\nu_{max}^{Neat}$ cm$^{-1}$: 3500–2800, 1760–1700.
NMR(90 MHz, CDCl$_3$)δ: 2.85(2H, m), 3.00(3H, s), 3.36(3H, s), 3.3–4.0(7H, m), 4.1(1H, m), 4.4(1H, m), 4.86(2H, s), 6.2(1H, bs), 6.9(1H, bs).

Reference Example 39

3,4-cis-3-[1-(2-Methoxyethoxymethoxy)-2-methylsulfonylethyl]-4-[3-(4-nitrobenzyloxycarbonyl)-2-oxopropyl]-azetidin-2-one Using 230 mg of 3,4-cis-4-carboxymethyl-3-[1-(2-methoxyethoxymethoxy)-2-methylsulfonylethyl]azetidin-2-one as obtained in Reference Example 38 and following the procedure of Reference Example 6, 187 mg of the title compound is obtained as an oil.

$IR\nu_{max}^{Neat}$ cm$^{-1}$: 3320, 1760, 1720, 1350 1130.
NMR(90 MNz, CDCl$_3$)δ: 2.96(3H, s), 3.11(2H, d, J=7 Hz), 3.33(3H, s), 3.57(2H, s), 3.1–4.0(7H, m), 4.1(1H, m), 4.4(1H, m), 4.83(2H, s), 5.25(2H, s), 6.33(1H, bs), 7.50(2H, d, J=9 Hz), 6.20(2H, d, J=9 Hz).

Reference Example 40

3,4-cis-4-[3-(Diazo-3-(4-nitrobenzyloxycarbonyl)-2-oxopropyl]-3-[1-(2-methoxyethoxymethoxy)-2-methylsulfonylethyl]azetidin-2-one Using 87 mg of 3,4-cis-3-[1-(2-methoxyethoxymethoxy)-2-methylsulfonylethyl]-4-[3-(4-nitrobenzyloxycarbonyl)-2-oxopropyl]azetidin-2-one as obtained in Reference Example 39 and following the procedure of Reference Example 7, 172 mg of the title compound is obtained as an oil.

$IR\nu_{max}^{Neat}$ cm$^{-1}$: 3220, 2140, 1750, 1715, 1650, 1350.
NMR(90 MHz, CDCl$_3$)δ: 2.96(3H, s), 3.35(3H, s), 3.2–4.0(9H, m), 4.15(1H, m), 4.35(1H, m), 4.87(2H, ABq, J=10.5, 7.5 Hz), 5.33(2H, s), 6.21(1H, bs), 7.51(2H, d, J=9 Hz), 8.23(2H, d, J=9 Hz).

Reference Example 41

1,6-cis-7-t-Butyldimethylsilyl-8-oxo-7-azabicyclo[4.2.0]-oct-3-ene

In 10 ml of dimethylformamide are dissolved 2.46 g of 1,6-cis-8-oxo-7-azabicyclo[4.2.0]oct-3-ene, 3.00 g of t-butyldimethylsilyl chloride and 3.0 ml of triethylamine. The solution is stirred at 0° C. for one hour and at room temperature for one hour, and then poured into water and extracted twice with ethyl acetate. The organic layer is washed with water and saturated aqueous sodium chloride in that order and dried over Na$_2$SO$_4$. The solvent is then distilled off to give 4.70 g of the title compound as an oil.

$IR\nu_{max}^{Neat}$ cm$^{-1}$: 1740, 1720.
NMR(90 MHz, CDCl$_3$)δ: 0.92(9H, s), 1.9–2.7(4H, m), 3.36(1H, m), 3.89(1H, m), 5.6–6.1(2H, m).

Reference Example 42

1,6-cis-7-t-butyldimethylsilyl-3,4-dihydroxy-8-oxo-7-azabicyclo[4.2.0]octane

With ice-cooling and stirring under an argon gas stream, a solution of 106 mg of osmic acid in 4 ml of t-butanol is added dropwise to 24 ml of aqueous solution of 3.40 g of N-methylmorpholine N-oxide. And then, a solution of 4.70 g of 1,6-cis-7-t-butyldimethylsilyl-8-oxo-7-azabicyclo[4.2.0]oct-3-ene as obtained in Reference Example 41 in 10 ml of acetone is added to the above solution, and the mixture is stirred for 10 minutes. The precipitate is filtered off with the aid of Celite and the filtrate is extracted with chloroform. The organic layer is dried over MgSO$_4$ and the solvent is distilled off. The residue is subjected to column chromatography using silica gel (ethyl acetate) to give 3.40 g of the title compound.
m.p.: 83°–85° C.
IR$\nu_{max}^{KBr}$ cm$^{-1}$: 3420, 1730, 1700.
NMR(90 MHz, CDCl$_3$)δ: 0.96(9H, s), 1.8–2.4(4H, m), 3.18(2H, bs), 3.43(1H, m), 3.6–4.3(3H, m).

Reference Example 43

1,5-cis-6-t-Butyldimethylsilyl-2-hydroxymethyl-7-oxo-6-azabicyclo[3.2.0]hept-2-ene At 0° C., 2.16 g of periodic acid is added to a solution of 2.08 g of 1,6-cis-7-t-butyldimethylsilyl-3,4-dihydroxy-8-oxo-6-azabicyclo[4.2.0]octane as obtained in Reference Example 42 in 60 ml of tetrahydrofuran, and the mixture is stirred vigorously. The mixture is further stirred at room temperature for 45 minutes, poured into water and extracted with chloroform. The organic layer is washed with saturated aqueous sodium chloride and dried over MgSO$_4$. The solvent is then distilled off to give a dialdehyde derivative. (IR$\nu_{max}^{neat}$ cm$^{-1}$: 2730, 1730). This product is dissolved in 140 ml of benzene, and to the solution is added 465 mg of dibenzylamine trifluoroacetate followed by heating at 60° C. for 50 minutes. The temperature is lowered to room temperature, and 30 ml of methanol and then 540 mg of sodium borohydride are added. The mixture is stirred for 90 minutes. The solvent is distilled off, and ethyl acetate and diluted hydrochloric acid are added. The precipitate is filtered off with the aid of Celite and the filtrate is extracted with ethyl acetate. The organic layer is washed with water and saturated aqueous sodium chloride, and dried over MgSO$_4$. The solvent is then distilled off. The residue is subjected to column chromatography using silica gel [ethyl acetate-chloroform=1:1] to give 1.104 g of the title compound.
IR$\nu_{max}^{KBr}$ cm$^{-1}$: 3400, 1720.
NMR(90 MHz, CDCl$_3$)δ: 0.94(9H, s), 2.50(2H, m), 2.83(1H, bs), 4.1(2H, m), 4.26(2H, m), 5.59(1H, bs).

Reference Example 44

1,5-cis-6-t-Butyldimethylsilyl-2-chloromethyl-7-oxo-6-azabicyclo[3.2.0]hept-2-ene Method (a) In a mixture of 7 ml of tetrahydrofuran and 7 ml of ether is dissolved 365 mg of 1,5-cis-6-t-butyldimethylsilyl-2-hydroxymethyl-7-oxo-6-azabicyclo-[3.2.0]hept-2-ene as obtained in Reference Example 43, and the solution is cooled to −25° C., followed by addition of 0.12 ml of pyridine and 0.11 ml of thionyl chloride. The mixture is stirred at room temperature for 30 minutes, poured into water and extracted with ethyl acetate. The organic layer is washed with water and saturated aqueous sodium chloride in that order and dried over MgSO$_4$. The solvent is then distilled off and the residue is subjected to column chromatography using silica gel (chloroform) to give 172 mg of the title compound as an oil.
IR$\nu_{max}^{Neat}$ cm$^{-1}$: 1740.
NMR(90 MHz, CDCl$_3$)δ: 0.94(9H, s), 2.53(2H, m), 3.9–4.4 (4H, m), 5.74(1H, m).

Method (b) To a solution of 65 mg of N-chlorosuccinimide in 4 ml of methylene chloride is added 0.039 ml of dimethyl sulfide at 0° C., and the mixture is cooled to −20° C. And then, to the mixture is added a solution of 112 mg of 1,5-cis-6-t-butyldimethylsilyl-2-hydroxymethyl-7-oxo-6-azabicyclo[3.2.0]hept-2-ene in 2 ml of dichloromethane. The mixture is stirred at 0° C. for an hour and added to ethyl acetate, followed by addition of water and extraction with ethyl acetate. The organic layer is washed with water and saturated aqueous sodium chloride in that order and dried over Na$_2$SO$_4$. The solvent is then distilled off and the residue is subjected to column chromatography using silica gel to give 75 mg of the title compound.

Reference Example 45

1,5-cis-2-Bromomethyl-6-t-butyldimethylsilyl-7-oxo-6-azabicyclo[3.2.0]hept-2-ene At 0° C., 0.27 ml of dimethyl sulfide is added to a solution of 555 mg of N-bromosuccinimide in 10 ml of methylene chloride, and the mixture is cooled to −20° C. And then, a solution of 526 mg of 1,5-cis-6-t-butyldimethylsilyl-2-hydroxymethyl-7-oxo-6-azabicyclo[3.2.0]-hept-2-ene as obtained in Reference Example 43 in 5 ml of dichloromethane is added. The temperature is returned to 0° C. over a period of an hour and the mixture is stirred at the same temperature for 3 hours, followed by the workup procedure of Reference Example 44 (b), to give 444 mg of the title compound as an oil.
IR$\nu_{max}^{Neat}$ cm$^{-1}$: 1740.
NMR(90 MHz, CDCl$_3$)δ: 0.93(9H, s), 2.53(2H, m), 3.9–4.4(4H, m), 5.76(1H, m).

Reference Example 46

6,7-cis-7-(2-Chloro-1-hydroxyethyl)-8-oxo-2,2-dimethyl-3-oxa-1-azabicyclo[4.2.0]octane At −78° C., ozone is bubbled into a solution of 239 mg of 1,5-cis-6-t-butyldimethylsilyl-2-chloromethyl-7-oxo-6-azabicyclo[3.2.0]hept-B 2-ene in 10 ml of methanol until the color of the mixture turns blue. Nitrogen gas is then bubbled into the mixture, and 33 mg of sodium borohydride is added at −40° C. The temperature is returned to room temperature. The mixture is stirred for an hour and the solvent is distilled off, followed by addition of ethyl acetate and diluted hydrochloric acid and extraction with ethyl acetate. The organic layer is washed with water and saturated aqueous sodium chloride and dried over MgSO$_4$. The solvent is then distilled off to give 288 mg of the corresponding diol derivative.
IR$\nu_{max}^{Neat}$ cm$^{-1}$: 3370, 1730.
NMR(90 MHz, CDCl$_3$)δ: 0.94(9H, s), 1.8–2.2(2H, m), 3.3–4.4(7H, m).

The above diol derivative is dissolved in 3 ml of tetrahydrofuran, and 297 mg of tetra-n-butylammonium fluoride is added, followed by stirring at room temperature for 45 minutes. The solvent is then distilled off and the residue is subjected to column chromatography using silica gel [ethyl acetate-methanol=20:1] to give 173 mg of the corresponding desilylated compound.
IR$\nu_{max}^{Neat}$ cm$^{-1}$: 3300, 1740.
NMR(90 MHz, acetone-d$_6$)δ: 1.8–2.3(2H, m), 2.87(2H, bs), 3.33(1H, m), 3.5–4.3(6H, m), 7.3(1H, bs).

In 2 ml of dichloromethane is dissolved 105 mg of the above desilylated compound, and 0.09 ml of dimethoxypropane and then one drop of boron trifluoride etherate are added. The mixture is stirred at room temperature for 30 minutes, poured into a buffer solution of pH 6.86 and extracted with dichloromethane. The extract is washed with saturated aqueous sodium chloride and dried over Na$_2$SO$_4$. The solvent is then distilled off and the residue is subjected to column chromatography using silica gel [ethyl acetate-hexane=1:1] to give 86 mg of the title compound.

m.p.: 121°–123° C.
IR$\nu_{max}^{KBr}$ cm$^{-1}$: 3400, 1740.
NMR(90 MHz, CDCl$_3$)δ: 1.40(3H, s), 1.71(3H, s), 1.6–2.1(2H, m), 2.5(1H, bs), 3.31(1H, dd, J=11 Hz, 6 Hz), 3.5–4.3(6H, m).

Reference Example 47

6,7-cis-7-(2-Bromo-1-hydroxyethyl)-8-oxo-2,2-dimethyl-3-oxa-1-azabicyclo[4.2.0]octane Using 444 mg of 1,5-cis-2-bromomethyl-6-t-butyldimethylsilyl-7-oxo-6-azabicyclo[3.2.0]hept-2-ene as obtained in Reference Example 45 and following the procedure of Reference Example 46, 478 mg of the corresponding 1,2-diol derivative is obtained.
IR$\nu_{max}^{Neat}$ cm$^{-1}$: 3340, 1740.
NMR(90 MHz, CDCl$_3$)δ: 0.97(9H, s), 2.0(2H, m), 3.3–4.4(7H, m).

In 20 ml of methanol is dissolved 1050 mg of the 1,2-diol derivative, and 346 mg of potassium fluoride is added, followed by stirring at room temperature for one hour. The solvent is then distilled off and the residue is subjected to column chromatography using silica gel [ethyl acetate-methanol=20:1] to give 656 mg of the corresponding desilylated compound.
IR$\nu_{max}^{Neat}$ cm$^{-1}$: 3300, 1740.
NMR(90 MHz, acetone-d$_6$)δ: 1.7–2.1(2H, m), 3.1–4.2(7H, m), 7.2(1H, bs).

Using 656 mg of the above desilylated compound and following the procedure of Reference Example 46, 482 mg of the title compound is obtained.
m.p.: 133°–135° C.
IR$\nu_{max}^{KBR}$ cm$^{-1}$: 3400, 1740.
NMR(90 MHz, CDCl$_3$)δ: 1.40(3H, s), 1.69(3H, s), 1.7–2.0(2H, m), 2.5(1H, bs), 3.29(1H, dd, J=11 Hz, 6 Hz), 3.5–4.3(6H, m).
Elemental analysis Calcd. for C$_{10}$H$_{16}$BrNO$_3$ (%): C, 43.18; H, 5.80; N, 5.04 Found (%): C, 43.34; H, 5.59; N, 5.11.

Reference Example 48

6,7-cis-7-(1-Hydroxy-2-phenylthioethyl)-8-oxo-2,2-dimethyl-3-oxa-1-azabicyclo[4.2.0]octane To a solution of 128 mg of sodium hydride in 20 ml of dimethylformamide is added 0.33 ml of thiophenol and the mixture is stirred for 5 minutes. To the mixture is added 445 mg of 6,7-cis-7-(2-bromo-1-hydroxyethyl)-8-oxo-2,2-dimethyl-3-oxa-1-azabicyclo[4.2.0]octane as obtained in Reference Example 47, and the resulting mixture is stirred at room temperature for 2 hours, poured into water and extracted with ethyl acetate. The organic layer is washed with water and saturated aqueous sodium chloride and dried over Na$_2$SO$_4$. The solvent is then distilled off and the residue is subjected to column chromatography using silica gel [ethyl acetate-hexane=1:1] to give 492 mg of the title compound as an oil.
IR$\nu_{max}^{Neat}$ cm$^{-1}$: 3420, 1740.
NMR(90 MHz, CDCl$_3$)δ: 1.36(3H, s), 1.69(3H, s), 1.7–2.0(2H, m), 2.7(1H, bs), 2.83(2H, dd, J=14 Hz, 9 Hz), 3.23(1H, dd, J=11 Hz, 6 Hz), 3.5–4.2(4H, m), 7.1–7.5(5H, m).

Reference Example 49

6.7-cis-7-(2-Ethylthio-1-hydroxyethyl)-8-oxo-2,2-dimethyl-3-oxa-1-azabicyclo[4.2.0]octane Using 250 mg of 6,7-cis-7-(2-bromo-1-hydroxyethyl)-8-oxo-2,2-dimethyl-3-oxa-1-azabicyclo[4.2.0]octane as obtained in Reference Example 47 and 0.20 ml of ethylmercaptane and following the procedure of Reference Example 48, 233 mg of the title compound is obtained.
m.p.: 60°–62° C.
IR$\nu_{max}^{KBr}$ cm$^{-1}$: 3420, 1740.
NMR(90 MHz, CDCl$_3$)δ: 1.20(3H, t, J=7.5 Hz), 1.36(3H, s), 1.59(3H, s), 1.7–2.0(2H, m), 2.57(1H, dd, J=14 Hz, 7.5 Hz), 2.59(2H, q, J=7.5Hz), 2.90(1H, s), 3.04(1H, dd, J=14 Hz, 3 Hz), 3.28(1H, dd, J=10 Hz, 5 Hz), 3.6–4.3(4H, m).
Elemental analysis Calcd. for C$_{12}$H$_{21}$NO$_3$S (%): C, 55.57; H, 8.16; N, 5.40 Found (%): C, 55.74; H, 8.29; N, 5.36.

Reference Example 50

1-Methyl hydrogen (1R,2S)-1,2-cyclohex-4-ene-dicarboxylate

In 400 ml of methanol are dissolved 82.3 g of racemic 1-methyl hydrogen 1,2-cis-1,2-cyclohex-4-ene-dicarboxylate and 136.3 g of cinchonidine, followed by concentration. The residue is dissolved in 700 ml of acetone and the solution is allowed to stand at 5° C. for 4 days. The resulting crystalline precipitate is collected by filtration, washed with acetone, dissolved in a hot mixture of 75 ml of methanol and 150 ml of acetone, and the solution is allowed to stand at 5° C. for one day. The resulting crystalline precipitate is collected by filtration and washed with acetone to give 62 g of the cinchonidine salt of the title compound. m.p. 156°–157° C., $[\alpha]_D^{24}$: −88.4° (c=0.57, methanol).

The above crystals are suspended in 300 ml of ethyl acetate and the suspension is washed twice with 1N hydrochloric acid and once with aqueous sodium chloride and dried over MgSO$_4$. The solvent is then distilled off to give 23 g of the title compound as an oil.
NMR(90 MHz, CDCl$_3$)δ: 2.1–2.9(4H, m), 2.9–3.2(2H, m), 3.70(3H, s), 5.67(2H, s), 11.68(1H, s).
$[\alpha]_D^{24}$: −13.6° (c=2.4, EtOH)

The mother liquor of the cinchonidine salt is treated with acid as mentioned above. The crystalline precipitate from hexane-ether (4:1) is filtered off (this procedure is repeated twice), the filtrate is concentrated to give 18.8 g of 1-methyl hydrogen (1S, 2R)-1,2-cyclohex-4-ene-dicarboxylate as an oil.
$[\alpha]_D^{26}$: +13.4° (c=2.3, EtOH).

Reference Example 51 t-butyl (1S,2R)-2-methylsulfonylethoxycarbonylamino-1-cyclohex-4-ene-carboxylate In 280 ml of dichloromethane is dissolved 25.7 g of 1-methyl hydrogen (1R,2S)-1,2-cyclohex-4-ene-dicarboxylate as obtained in Reference Example 50 and, with ice-cooling and stirring, 1.5 ml of sulfuric acid is added. Isobutene is passed through the mixture for about 30 minutes. After the mixture is allowed to stand in a tightly closed container for 3 days, isobutene is passed through again. The mixture is allowed to stand for one day and then concentrated under reduced pressure. To the residue is added 300 ml of ether and the mixture is washed twice with sodium hydrogen carbonate and twice with saturated aqueous sodium chloride and dried over MgSO$_4$. The solvent is then distilled off to give 30.6 g of the corresponding diester as an oil.

This product is dissolved in 250 ml of methanol, and a solution of 8.34 g of sodium hydroxide in 100 ml of water is added. The mixture is allowed to stand at room temperature for 20 hours. The methanol is distilled off under reduced pressure and the residue is diluted with water, followed by extraction of impurities with ether. And then, with ice-cooling, 21.5 ml of concentrated hydrochloric acid is added to the aqueous layer and the mixture is extracted twice with ether. The organic layer is washed with saturated aqueous sodium chloride and dried over MgSO$_4$. The solvent is then distilled off to give 26.9 g of the corresponding t-butyl ester carboxylic acid.

The above product is dissolved in 400 ml of dichloromethane, and 12.6 g of triethylamine is added to the solution with sodium chloride-ice cooling. And then, 13.5 g of ethyl chloroformate is added and the mixture is stirred for 40 minutes. To the mixture are added 80 ml of an aqueous solution of 16.1 g of sodium azide and 8.4 g of tetrabutylammonium hydrogen sulfate and the mixture is stirred with ice-cooling for one hour. After addition of ice-water, the dichloromethane layer is separated and the aqueous layer is extracted with dichloromethane. The organic layers are combined and washed with saturated aqueous sodium chloride and dried over MgSO$_4$. The solvent is distilled off and the residue is dissolved in 180 ml of toluene, followed by stirring at 100° C. for 15 minutes. After cooling, a solution of 44 g of 2-methylsulfonylethanol in 180 ml of tetrahydrofuran and 3 g of triethylamine are added. The mixture is stirred at room temperature for 18 hours and concentrated under reduced pressure. The residue is subjected to column chromatography using silica gel [hexane-ethyl acetate=1:1] to give 39.3 g of the title compound.

IR$\nu_{max}^{KBr}$ cm$^{-1}$: 3350, 1725, 1520, 1305, 1150, 1130.

NMR(90 MHz, CDCl$_3$)δ: 1.44 (9H, s), 2.6–2.9(1H, m), 2.97(3H, s), 3.32(2H, t, J=5 Hz), 4.0–4.4(1H, m), 4.48(2H, t, J=5 Hz), 5.5–5.8(2H, m).

Reference Example 52

(1S,2R)-2-Amino-1-cyclohex-4-enecarboxylic acid

In a mixture of 210 ml of dioxane and 75 ml of methanol is dissolved 8.69 g of t-butyl (1S,2R)-2-methylsulfonylethoxycarbonylamino-1-cyclohex-4-ene-carboxylate as obtained in Reference Example 51, and 15 ml of 5N sodium hydroxide is added. The mixture is stirred at room temperature for 15 minutes. After addition of 4.6 ml of acetic acid, the mixture is concentrated under reduced pressure, followed by addition of aqueous sodium hydrogen carbonate to the residue and extraction with chloroform. The organic layer is washed with saturted aqueous sodium chloride and dried over MgSO$_4$. The solvent is then distilled off. To the residue is added 15 ml of trifluoroacetic acid and the mixture is allowed to stand at room tempêrature for 24 hours. With ice-cooling, 75 ml of Dowex 50 W (H+) resin (Dow Chemical Co., USA) and 50 ml of water are added, and the mixture is stirred at room temperature for 30 minutes. The resin is filtered off and washed with water and elution is carried out with 300 ml of 5% ammonia water. The eluate is concentrated to dryness. To the residue is added acetone and the resulting crystalline precipitate is collected by filtration to give 2.56 g of the title compound.

m.p. 225° C. (decomp.).

IR$\nu_{max}^{KBr}$ cm$^{-1}$: 3300, 1700, 1620, 1550, 1440, 1415, 1350, 690.

NMR(90 MHz, CDCl$_3$+CF$_3$COOH)δ: 2.3–3.0(4H, m), 3.0–3.4(1H, m), 3.8–4.3(1H, m), 5.5–6.1(2H, m), 7.15(3H, bs).

Elemental analysis Calcd. for C$_7$H$_{11}$NO$_2$.$\frac{1}{2}$H$_2$O (%): C, 55.98; H, 8.06; N, 9.33 Found (%): C, 55.55; H, 7.93; N, 9.31.

$[\alpha]_D^{25}$: +36.6° (c=0.56, H$_2$O).

Reference Example 53

(1S,6R)-7-t-Butyldimethylsilyl-8-oxo-7-azabicyclo[4.2.0]-oct-3-ene

A suspension of 424 mg of (1S,2R)-2-amino-1-cyclohex-4-enecarboxylic acid as obtained in Reference Example 52, 997 mg of triphenylphosphine, 838 mg of 2,2'-dipyridyl disulfide and 652 mg of manganese dioxide in 60 ml of acetonitrile is refluxed with vigorous stirring for 3.5 hours. After cooling, the insoluble matter is filtered off and the filtrate is concentrated under reduced pressure. The residue is subjected to column chromatography using silica gel (ethyl acetate). The eluate is concentrated and treated in the same manner as Reference Example 41 to give 485 mg of the title compound as a colorless oil.

The IR and NMR spectra of this compound are in good accordance with those of the compound obtained in Reference Example 41.

$[\alpha]_D^{25}$: −45.2° (c=1.525, ethanol).

Reference Example 54

(6R,7R)-7-(2-Bromo-1-hydroxyethyl)-8-oxo-2,2-dimethyl-3-oxa-1-azabicyclo[4.2.0]octane Using (1S,6R)-7-t-butyldimethylsilyl-8-oxo-7-azabicyclo[4.2.0]oct-3-ene-as obtained in Reference Example 53 and following the procedure of Reference Examples 42 and 43, (1S,5R)-6-t-butyldimethylsilyl-2-hydroxymethyl-7-oxo-6-azabicyclo[3.2.0]hept-2-ene is obtained.

$[\alpha]_D^{25}$: +83.6° (c=1.35, chloroform).

The above product is treated in the same manner as Reference Example 45 to give (1S,5R)-2-bromomethyl-6-t-butyldimethylsilyl-7-oxo-6-azabicyclo[3.2.0]hept-2-ene.

$[\alpha]_D^{25}$: −32.1° (c=1.05, chloroform).

The above product is treated in the same manner as Reference Example 47 to give the title compound.

m.p.: 141°–142° C.

$[\alpha]_D^{25}$: +13.0° (c=0.54, chloroform).

Reference Example 55

6,7-trans-7-(1-Methylsulfonylethyl)-8-oxo-2,2-dimethyl-3-oxa-1-azabicyclo[4.2.0]octane To a solution of 0.25 g of 7-ethylidene-8-oxo-2,2-dimethyl-3-oxa-1-azabicyclo[4.2.0]octane (Z-isomer:Ed-isomer=2:3) in 2 ml of dimethylformamide is added 1 ml of 15% methylmercaptan sodium salt solution. The mixture is stirred at room temperature for one hour, diluted with ethyl acetate, washed with water and dried over Na$_2$SO$_4$. The solvent is then distilled off to give 6,7-trans-7-(1-methylthioethyl)-8-oxo-2,2-dimethyl-3-oxa-1-azabicyclo[4.2.0]octane as a light-yellow oil. This product is treated in the same manner as Reference Example 4 to give 0.27 g [a mixture of isomers (ca, 2:1)] of the title compound as a colorless oil.

IR$\nu_{max}^{Nujor}$ cm$^{-1}$: 1740.

NMR(90 MHz, CDCl$_3$)δ: 1.40(3H, s), 1.58(3H, d, J=6 Hz), 1.73(3H, s), 2.0(2H, m), 2.87(2H, s), 2.93(1H, s), 3.0–4.0(5H, m)

Reference Example 56

6.7-cis-7-[1-(2-Methoxyethoxymethoxy)-2-phenylthioethyl]-2,2-dimethyl-3-oxa-1-azabicyclo[4.2.0]octan Using 667 mg of 6,7-cis-7-(1-hydroxy-2-phenylthioethyl-8-oxo-2,2-dimethyl-3-oxa-1-azabicyclo[4.2.0]octane as obtained in Reference Example 48 and following the procedure of Reference Example 3, 858 mg of the title compound is obtained.

IR$\nu_{max}^{Neat}$ cm$^{-1}$: 1750.

NMR(90 MHz, CDCl$_3$)δ: 1.36 (3H, s), 1.69(3H, s), 1.7–2.1(2H, m), 3.36(3H, s), 3.3–3.9(10H, m), 4.20(1H, m), 4.81(2H, m), 7.1–7.6(5H, m).

Reference Example 57

6,7-cis-7-[1-(4-Nitrobenzyloxycarbonyloxy)-2-ethylthioethyl]-8-oxo-2,2-dimethyl-3-oxa-1-azabicyclo[4.2.0]octane To a solution of 233 mg of 6,7-cis-7-(2-ethylthio-1-hydroxyethyl)-8-oxo-2,2-dimethyl-3-oxa-1-azabicyclo[4.2.0]-octane as obtained in Reference Example 49 and 16 ml of dichloromethane are added 329 mg of dimethylaminopyridine and 291 mg of 4-nitrobenzyl chloroformate with ice-cooling, and the mixture is stirred at room temperature for 18 hours. The solvent is then distilled off and the residue is extracted with ethyl acetate. The organic layer is washed with diluted hydrochloric acid, water, aqueous sodium hydrogen carbonate, water and saturated aqueous sodium chloride in that order and dried over Na$_2$SO$_4$, followed by removal of the solvent by distillation. The residue is subjected to silica gel column chromatography (ethyl acetate -hexane=1:1) to give 292 mg of the title compound as an oil.

IR$\nu_{max}^{Neat}$ cm$^{-1}$: 1760, 1740.

NMR(90 MHz, CDCl$_3$)δ: 1.21(3H, t, J=7.5 Hz), 1.40(3H, s), 1.72(3H, s), 1.8–2.0(2H, m), 2.56(2H, q, J=7.5 Hz), 2.74(1H, dd, J=7.5, 15 Hz), 3.23(1H, dd, J=3.5, 15 Hz), 3.5–4.2(4H, m), 5.25(1H, m), 5.26(2H, s), 7.53(2H, d, J=9 Hz), 8.21(2H, d, J=9 Hz).

Reference Example 58

6,7-cis-7-[1-(2-Methoxyethoxymethoxy)-1-methylthiomethyl-2-methylthioethyl]-8-oxo-2,2-dimethyl-3-oxa-1-azabicyclo-[4.2.0]octane Using 450 mg of 1,3-dimethylthioacetone and following the procedure of Reference Examples 1 and 2, 205 mg of 6,7-cis-7-(1-hydroxy-1-methylthiomethyl-2-methylthioethyl)-8-oxo-2,2-dimethyl-3-oxa-1-azabicyclo[4.2.0]octane is obtained as colorless crystals.

m.p. 82°–83° C.

IR$\nu_{max}^{KBr}$ cm$^{-1}$: 3400, 1710.

NMR(90 MHz, CDCl$_3$)δ: 1.38(3H, s), 1.76(3H, s), 1.90(2H, m), 2.18(3H, s), 2.22(3H, s), 2.83(2H, s), 2.76(2H, s), 3.17(2H, s), 3.55(1H, d, J=6 Hz), 3.68–4.95(3H, m).

Using 200 mg of this compound and following the procedure of Reference Example 3, 221 mg of the title compound is obtained as an oil. This compound is used as a material for a following reaction without purification.

Reference Example 59

(1) The following compounds are obtained according to the same manner as Reference Example 4.

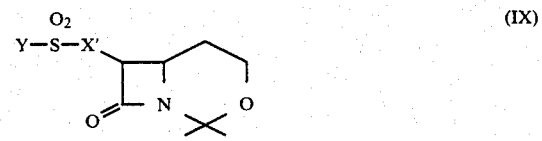

(IX)

a group of the formula:

O$_2$
Y—S—X'—

| Y—S(O$_2$)—X'— | NMR(90 MHz, CDCl$_3$) δ value |
|---|---|
| CH$_3$S(O$_2$)—CH$_2$\C/(OCH$_2$OCH$_2$CH$_2$OCH$_3$)\CH$_2$—S(O$_2$)CH$_3$ | 1.38(3H,s), 1.70(3H,s), 1.90(2H,m), 2.98(3H,s), 3.00(3H,s), 3.37(3H,s), 3.40–4.40(12H,m), 5.12(2H,q) |
| PhS(O$_2$)—CH$_2$—CH(OCH$_2$OCH$_2$CH$_2$OCH$_3$)— | 1.36(3H,s), 1.66(3H,s), 1.8–2.1(2H,m), 3.33(3H,s), 3.3–4.0(10H,m), 4.6(1H,m), 4.75(2H,m), 7.4–8.1(5H,m) |
| C$_2$H$_5$S(O$_2$)—CH$_2$CH(O—COCH$_2$—C$_6$H$_4$—NO$_2$)— | 1.40(3H,t,J=7.5Hz), 1.40(3H,s), 1.70(3H,s), 1.8–2.0(2H,m), 3.08(2H,q, J=7.5Hz), 3.35(1H,dd, J=5, 9Hz), 3.5–4.1(5H,m), 5.28(2H,ABq,J=14,15Hz), 5.66(1H,m), 7.53(2H,d,J=9Hz), 8.21(2H,d,J=9Hz) |

(2) The following compounds are obtained according to the same manner as Reference Examples 5 and 6.

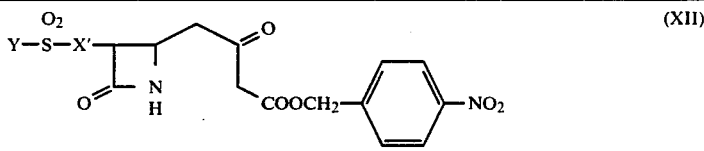

a group of the formula:

| $Y-S-X'-$ with $O_2$ | NMR(90 MHz, CDCl$_3$) δ value | IR $\nu_{max}^{Neat}$ cm$^{-1}$ |
|---|---|---|
| CH$_3$S—CH$_2$ \ C(OCH$_2$OCH$_2$CH$_2$OCH$_3$) / CH$_2$S—CH$_2$ (both with O$_2$) | 2.98(3H,s), 3.00(3H,s), 3.30(3H,s), 3.65(2H,s), 3.42-4.40(12H,m), 5.19(2H,q), 5.27(2H,s), 6.68(1H,bs), 7.51(2H,d,J=11Hz), 8.21(2H,d,J=11Hz) | 1750 |
| PhS(O$_2$)—CH$_2$—CH(OCH$_2$OCH$_2$CH$_2$OCH$_3$) | 3.30(3H,s), 3.59(2H,s), 3.2-4.0(9H,m), 4.1(1H,m), 4.6(1H,m), 4.78(2H,ABq, J=7.5,6Hz), 5.26(2H,s), 6.20(1H,bs), 7.4-8.1 (7H,m), 8.23(2H,d,J=9Hz) | 3350 1755 1720 |
| C$_2$H$_5$S(O$_2$)—CH$_2$CH(O—COCH$_2$-C$_6$H$_4$-NO$_2$) | 1.30(3H,t,J=7.5Hz), 3.15(2H,q,J=7.5Hz), 3.16(2H,d,J=6.8Hz), 3.66(2H,s), 3.2-4.0(3H,m), 4.20(1H,m), 5.30(2H,s), 5.33(2H,s), 5.65(1H,m), 7.40(1H,bs), 7.66(2H,d,J=9Hz), 8.21(2H,d,J=9Hz) | 3410 1760 1720 |
| CH$_3$S(O$_2$)—CH(CH$_3$)— (isomer A) | 1.60(3H,d,J=6Hz), 2.6-3.6(4H,m), 2.90(3H,s), 3.55(2H,s), 4.02(1H,m), 5.27(2H,s), 6.2(1H,bs), 7.52(2H,d, J=9Hz), 8.22(2H,d,J=9Hz) | 3340 1770 1700 |
| CH$_3$S(O$_2$)—CH(CH$_3$)— (isomer B) | 1.47(3H,d,J=6Hz), 2.5-3.6(4H,m), 2.93(3H,s), 3.56(2H,s), 4.06(1H,m), 5.25(2H,s), 6.4(1H,bs), 7.50(2H,d,J=9Hz), 8.21(2H,d,J=9Hz) | 3370 1170-1700 |

(3) The following compounds are obtained according to the same manner as Reference Example 7.

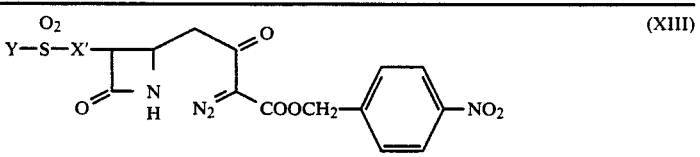

a group of the formula:

| $Y-S-X'-$ with $O_2$ | NMR(90 MHz, CDCl$_3$) δ value | IR $\nu_{max}^{Neat}$ cm$^{-1}$ |
|---|---|---|
| CH$_3$S—CH$_2$ \ C(OCH$_2$OCH$_2$CH$_2$OCH$_3$) / CH$_3$S—CH$_2$ (both with O$_2$) | 3.01(6H,s), 3.26(3H,s), 3.36-4.40(12H,m), 5.02(2H,q,J=8.15Hz), 5.30(2H,s), 6.43(1H,bs), 7.48(2H,d,J=11Hz), 8.20(2H,d,J=11Hz) | 2140 1760 1720 |

-continued

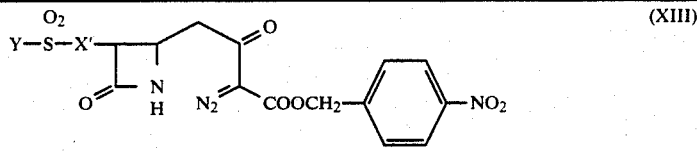 (XIII)

a group of the formula:
Y—S—X'—

| Y—S—X'— | NMR(90 MHz, CDCl$_3$) δ value | IR $\nu_{max}^{Neat}$ cm$^{-1}$ |
|---|---|---|
| 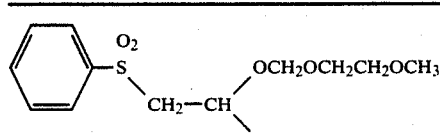 | 3.30(3H,s), 3.2–4.0 (9H,m), 4.2(1H,m), 4.6(1H,m), 4.74(2H,s), 5.36(2H,s), 6.26(1H, bs), 7.4–8.1(7H,m), 8.25(2H,d,J=9Hz) | 3340 2140 1760 1720 1650 |
| 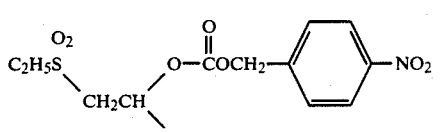 | — | 3245 2150 1760 1715 |
| 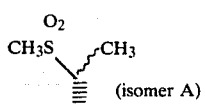 (isomer A) | 1.58(3H,d,J=6Hz), 2.90(3H,s), 2.9–3.7 (4H,m), 4.03(1H,m), 5.36(2H,s), 6.42(1H,bs), 7.51(2H,d,J=9Hz), 8.21(2H,d,J=9Hz) | 3340 2150 1780–1700 1640 |
| 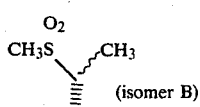 (isomer B) | 1.47(3H,d,J=6Hz), 2.93(3H,s), 2.8–3.7 (4H,m), 4.10(1H,m), 5.33(2H,s), 6.30(1H,bs), 7.53(2H,d,J=9Hz), 8.23(2H,d,J=9Hz) | 3330 2150 1780–1700 1650 |

Example 1

Sodium 5,6-cis-3-(2-acetamidoethylthio)-6-(1-hydroxy-3-thiacyclopentyl-3,3-dioxido)-7-oxo-1-azabicyclo-[3.2.0]hept-2-ene-2-carboxylate (a) Production of 4-nitrobenzyl 5,6-cis-6-(1-hydroxy-3-thiacyclopentyl-3,3-dioxido)-1-azabicyclo[3.2.0]heptane-3,7-dione-2-carboxylate In order to remove oxygen, nitrogen gas is bubbled into a mixture of 60 mg of 3,4-cis-4-[3-diazo-3-(4-nitrobenzyloxycarbonyl)-2-oxopropyl]-3-(1-hydroxy-3-thiacyclopentyl-3,3-dioxido)azetidin-2-one (benzene solvate) as obtained in Reference Example 8, 5 mg of rhodium(II) acetate, 4 ml of dry tetrahydrofuran and 6 ml of dry benzene for 10 minutes. Thereafter, with stirring under a nitrogen atomsphere, the mixture is heated at 80° C. for 7 minutes. The solvent is then distilled off to give the title compound as a frothy substance in quantitative yield.

IR$\nu_{max}^{KBr}$ cm$^{-1}$: 3470, 1770, 1740, 1350, 1120.

NMR(90 MHz, acetone-d$_6$)δ: 2.4~3.3(8H, m), 3.69(1H, d, J=6 Hz), 3.9(1H, m), 4.23(1H, s), 4.86(2H, bs), 7.18(2H, d), 7.74(2H, d, J=9 Hz).

(b) Production of 4-nitrobenzyl 5,6-cis-3-(2-acetamidoethylthio)-6-(1-hydroxy-3-thiacyclopentyl-3,3-dioxido)-7-oxo-1-azabicyclo[3.2.0]hept-2-ene-2-carboxylate To a solution of 4-nitrobenzyl 5,6-cis-6-(1-hydroxy-3-thiacyclopentyl-3,3-dioxido)-1-azabicyclo[3.2.0]heptane-3,7-dione-2-carboxylate, prepared from 60 mg of 3,4-cis-4-[3-diazo-3-(4-nitrobenzyloxycarbonyl)-2-oxopropyl]-3-(1-hydroxy-3-thiacyclopentyl-3,3-dioxido)azetidin-2-one (benzene solvate) as obtained in Reference Example 8 in accordance with the above procedure (a), in 6 ml of dry acetonitrile is added 0.016 ml of diisopropylethylamine under a nitrogen atmosphere at 0° C., and then 0.019 ml of diphenylphoryl chloride is added, followed by stirring for 2 hours. To the mixture are added 0.016 ml of diisopropylethylamine and 11 mg of N-acetylcysteamine at 0° C. and the resulting mixture is stirred for an hour. The reaction mixture is allowed to stand at −20° C. for 14 hours and the solvent is distilled off. The residue is diluted with ethyl acetate, washed with water and dried over Na$_2$SO$_4$ and the solvent is distilled off. The residue is subjected to column chromatography (acetone-chloroform=1:1) using Florisil to give the title compound (23 mg) as an oil.

IR$\nu_{max}^{Neat}$ cm$^{-1}$: 3380, 1770, 1700, 1650, 1330, 1120.
UV$\lambda_{max}^{EtOH}$ nm: 269, 320.

NMR(90 MHz, acetone-d$_6$)δ: 1.90(3H, s), 2.7(2H, m), 2.8~3.8(10H, m), 4.08(1H, d), 4.4(1H, m), 5.38(2H, ABq, J=22, 14 Hz), 7.4(1H, m), 7.78(2H, d, J=9 Hz), 8.25(2H, d, J=9 Hz).

(c) Production of sodium 5,6-cis-3-(2-acetamidoethylthio)-6-(1-hydroxy-3-thiacyclopentyl-3,3-dioxido)-7-oxo-1-azabicyclo[3.2.0]hept-2-ene-2-carboxylate To a mixture of 57 mg of 4-nitrobenzyl 5,6-cis-3-(2-acetamidoethylthio)-6-(1-hydroxy-3-thiacyclopentyl- 3,3-dioxido)-7-oxo-1-azabicyclo-[3.2.0]hept-2-ene-2-carboxylate obtained by the above procedure (b), 5 ml of tetrahydrofuran, 2.6 ml of phosphate buffer (pH 7.0) and 2.6 ml of water is added 50 mg of 10% palladium-on-carbon, and hydrogen gas is bubbled into the resulting mixture at room temperature and atmospheric pressure over a period of 1.5 hours. The catalyst is filtered off and washed with a small amount of water. The filtrate and washings are combined and the remaining tetrahydrofuran in the solution is distilled off under reduced pressure. The aqueous layer is washed with ethyl acetate and concentrated under reduced pressure and the concentrate is subjected to column chromatography ($H_2O$) using Amberlite XAD-2. The fractions showing UV absorption at 298 nm are combined and lyophilized to give 21 mg of a powder. This product is further purified by column chromatography ($H_2O$) using Diaion HP-20 to give the title compound (12 mg) as a colorless powder.

$IR\nu_{max}^{KBr}$ cm$^{-1}$: 3430, 1750, 1640.

$UV\lambda_{max}^{H2O}$ nm($E_{1\ cm}^{1\%}$): 298(134).

NMR(90 MHz, $D_2O$)δ: 2.01(3H, s), 2.5(2H, m), 2.8~3.9(10H, m), 4.00(1H, d, J=6 Hz), 4.4(1H, m).

EXAMPLE 2

Sodium 5,6-cis-3-(2-pyrimidinylthio)-6-(1-hydroxy-3-thiacyclopentyl-3,3-dioxido)-7-oxo-1-azabicyclo[3.2.0]hept-2-ene-2-caboxylate (a) Production of 4-nitrobenzyl 5,6-cis-3-(2-pyrimidinylthio)-6-(1-hydroxy-3-thiacyclopentyl-3,3-dioxido)-7-oxo-1-azabicyclo[3.2.0]hept-2-ene-2-carboxylate In a nitrogen atmosphere at 0° C., 0.014 ml of diisopropylethylamine is added to a solution of 4-nitrobenzyl 5,6-cis-6-(1-hydroxy-3-thiacyclopentyl-3,3-dioxido)-1-azabicyclo[3.2.0]heptane-3,7-dione-2-carboxylate, prepared from 100 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]-azetidin-2-one (obtained in Reference Example 7) in accordance with the procedures of Reference Example 8 and Example 1(a), in 8 ml of dry acetonitrile, and then 0.017 ml of phenylphosphoryl chloride is added, followed by stirring for 90 minutes. To this mixture is added 20 mg of the lithium salt of 2-mercaptopyrimidine and the resulting mixture is stirred at 0° C. for 18 hours. The reaction mixture is diluted with ethyl acetate and poured into ice water. The organic layer is separated, washed with water and dried over $Na_2SO_4$ and the solvent is distilled off. The residue is then subjected to column chromatography (acetone-chloroform=1:1) using Florisil to give the title compound (5 mg) as an oil.

$IR\nu_{max}^{KBr}$ cm$^{-1}$: 3450, 1780, 1710.

$UV\lambda_{max}^{EtOH}$ nm: 262, 318.

NMR(90 MHz, $CDCl_3$)δ: 2.4(2H, m), 3.1~3.8(6H, m), 3.86(1H, d, J=6 Hz), 4.5(1H, m), 5.36(2H, ABq, J=25, 14 Hz), 7.09(1H, t, J=5 Hz), 7.61(2H, d, J=9 Hz), 8.21(2H, d, J=9 Hz), 8.56(2H, d, J=6 Hz).

(b) Production of sodium 5,6-cis-3-(2-pyrimidinylthio)-6-(1-hydroxy-3-thiacyclopentyl-3,3-dioxido)-7-oxo-1-azabicyclo[3.2.0]hept-2-ene-2-carboxylate Using 50 mg of the 4-nitrobenzyl ester obtained by the above procedure (a) and following the procedure of Example 1(c), the title compound (6 mg) is obtained as a light-yellow powder.

$IR\nu_{max}^{KBr}$ cm$^{-1}$: 3400, 1750.

$UV\lambda_{max}^{H2O}$ nm($E_{1\ cm}^{1\%}$): 290(106).

NMR(90 MHz, $D_2O$)δ: 2.5~2.8(2H, m), 3.1~4.0(6H, m), 4.26(1H, d, J=6 Hz), 4.5(1H, m), 7.56(1H, t, J=5 Hz), 8.89(2H, d, J=5 Hz).

EXAMPLE 3

5,6-cis-3-(2-Aminoethylthio)-6-(1-hydroxy-3-thiacyclopentyl-3,3-dioxido)-7-oxo-1-azabicyclo[3.2.0]-hept-2-ene-2-carboxylic acid (a) Production of 4-nitrobenzyl 5,6-cis-3-[2-(4-nitrobenzyloxycarbonyl)aminoethylthio]-6-(1-hydroxy-3-thiacyclopentyl-3,3-dioxido)-7-oxo-1-azabicyclo[3.2.0]hept-2-ene-2-carboxylate Using 183 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 and following the procedure of Example 2(a), the title compound (87 mg) is obtained as an oil.

$IR\nu_{max}^{Neat}$ cm$^{-1}$: 3400, 1770, 1710.

$UV\lambda_{max}^{EtOH}$ nm: 268, 318.

NMR(90 MHz, (acetone-$d_6$)δ: 1.95(2H, m), 2.5~3.1(10H, m), 3.59(1H, d, J=6 Hz), 3.9(1H, m), 4.73(2H, s), 4.87(2H, ABq, J=29, 14 Hz), 6.8(1H, bs) 7.12(2H, d, J=9 Hz), 7.59(2H, d, J=9 Hz), 7.71(4H, d, J=9 Hz).

(b) Production of 5,6-cis-3-(2-aminoethylthio)-6-(1-hydroxy-3-thiacyclopentyl-3,3-dioxido)-7-oxo-1-azabicyclo[3.2.0]hept-2-ene-2-carboxylic acid Using 87 mg of the 4-nitrobenzyl ester obtained by the above procedure (a) and following the procedure of Example 1(c), the title compound (18 mg) is obtained as a colorless powder.

$IR\nu_{max}^{KBr}$ cm$^{-1}$: 3400, 1755.

$UV\lambda_{max}^{H2O}$ nm($E_{1\ cm}^{1\%}$): 295(109).

NMR(90 MHz, $D_2O$)δ: 2.6(2H, m), 3.0~4.0(10H, m), 4.15(1H, d, J=6 Hz), 4.5(1H, m).

EXAMPLE 4

5,6-cis-3-(2-Formimidoylaminoethylthio)-6-(1-hydroxy-3-thiacyclopentyl-3,3-dioxido)-7-oxo-1-azabicyclo[3.2.0]hept-2-ene-2-carboxylic acid A solution of 18 mg of 5,6-cis-3-(2-aminoethylthio)-6-(1-hydroxy-3-thiacyclopentyl-3,3-dioxido)-7-oxo-1-azabicyclo[3.2.0]hept-2-ene-2-carboxylic acid as obtained in Example 3 in 3.5 ml of phosphate buffer (pH 7.0) is adjusted to pH 8.5 by addition of 1N aqueous sodium hydroxide with ice-cooling. To this solution is added 63 mg of benzyl formimidate hydrochloride little by little over a period of 10 minutes while maintaining the pH at 8.5 with 1N aqueous sodium hydroxide. After stirring for 5 minutes, the reaction mixture is adjusted to pH 7.0 with 1N hydrochloric acid and washed with ethyl acetate. The aqueous layer is concentrated and the concentrate is subjected to column chromatography using Diaion HP-20. The 3% acetone eluate fractions are combined and lyophilized to give the title compound (12 mg) as a colorless powder $IR\nu_{max}^{KBr}$ cm$^{-1}$: 3400, 1750, 1720, 1300, 1120.

$UV\lambda_{max}^{H2O}$ nm($E_{1\ cm}^{1\%}$): 2.98(110).

NMR(90 MHz, D$_2$O)δ: 2.6(2H, m), 3.0~4.0(10H, m), 4.13(1H, d, J=6 Hz), 4.5(1H, m), 7.95(1H, s).

EXAMPLE 5

Sodium 5,6-cis-3-(2-acetamidoethylthio)-6-(1-hydroxy-4-thiacyclohexyl-4,4-dioxido)-7-oxo-1-azabicyclo[3.2.0]-hept-2-ene-2-carboxylate (a) Production of 4-nitrobenzyl 5,6-cis-3-(2-acetamidoethylthio)-6-(1-hydroxy-4-thiacyclohexyl-4,4-dioxido)-7-oxo-1-azabicyclo[3.2.0]hept-2-ene-2-carboxylate Using 67 mg of 3,4-cis-4-[3-diazo-3-(4-nitrobenzyloxycarbonyl)-2-oxopropyl]-3-[1-(2-methoxyethoxymethoxy)-4-thiacyclohexyl-4,4-dioxido]azetidin-2-one as obtained in Reference Example 15 and following the procedure of Example 2(a), the title compound (18 mg) is obtained as a frothy substance.

IR$\nu_{max}^{KBr}$ cm$^{-1}$: 3400, 1770, 1690, 1650, 1350, 1140.
UV$\lambda_{max}^{EtOH}$ nm: 268, 319.
NMR(90 MHz, acetone-d$_6$)δ: 1.90(3H, s), 2.1~3.7(14H, m), 3.84(1H, d, J=6 Hz), 4.4(1H, m), 5.40(2H, ABq, J=24, 14 Hz), 7.4(1H, m), 7.78(2H, d, J=9 Hz), 8.23(2H, d, J9 Hz).

(b) Production of sodium 5,6-cis-3-(2-acetamidoethylthio)-6-(1-hydroxy-4-thiacyclohexyl-4,4-dioxido)-7-oxo-1-azabicyclo[3.2.0]hept-2-ene-2-carboxylate Using 40 mg of the 4-nitrobenzyl ester obtained by the above procedure (a) and following the procedure of Example 1(c), the title compound (12 mg) is obtained as a colorless powder.

IR$\nu_{max}^{KBr}$ cm$^{-1}$: 3400, 1750, 1640.
UV$\lambda_{max}^{H2O}$ nm(E$_{1\ cm}^{1\%}$): 300(166).
NMR(90 MHz, D$_2$O)δ: 2.13(3H, s), 2.2~3.9(14H, m) 3.97(1H, d, J=6 Hz), 4.4(1H, m).

EXAMPLE 6

Sodium 5,6-trans-3-(2-acetamidoethylthio)-6-(1-hydroxy-2-methylsulfonylethyl)-7-oxo-1-azabicyclo[3.2.0]hept-2-ene-2-carboxylate (isomer A)

(a) Production of 4-nitrobenzyl 5,6-trans-3-(2-acetamidoethylthio)-6-(1-hydroxy-2-methylsulfonylethyl)-7-oxo-1-azabicyclo[3.2.0]hept-2-ene-2-carboxylate Using 121 mg of 3,4-trans-4-[3-diazo-3-(4-nitrobenzyloxycarbonyl)-2-oxopropyl]-3-[1-(2-methoxyethoxymethoxy)-2-methylsulfonylethyl]azetidin-2-one (isomer A) as obtained in Reference Example 21 and following the procedure of Example 2(a), 41 mg of the title compound is obtained as a white frothy substance.

IR$\nu_{max}^{KBr}$ cm$^{-1}$: 3440, 1790, 1700, 1640, 1340, 1130.
UV$\lambda_{max}^{EtOH}$ nm: 269, 321.

(b) Production of sodium 5,6-trans-3-(2-acetamidoethylthio)-6-(1-hydroxy-2-methylsulfonylethyl)-7-oxo-1-azabicyclo[3.2.0]hept-2-ene-2-carboxylate (isomer A)

Using 52 mg of the 4-nitrobenzyl ester obtained by the above procedure (a) and following the procedure of Example 1(c), the title compound (16 mg) is obtained as a light-yellow powder.

IR$\nu_{max}^{KBr}$ cm$^{-1}$: 3400, 1760, 1630.
UV$\lambda_{max}^{H2O}$ nm(E$_{1\ cm}^{1\%}$): 300(112).
NMR(90 MHz, D$_2$O)δ: 2.13(3H, s), 3.31(2H, s), 2.9~4.0(9H, m), 4.35(1H, m), 4.70(1H, m).

EXAMPLE 7

Sodium 5,6-trans-3-(2-acetamidoethylthio)-6-(1-hydroxy-2-methylsulfonylethyl)-7-oxo-1-azabicyclo[3.2.0]hept-2-ene-2-carboxylate (mixture of isomers A and B)

(a) Production of 4-nitrobenzyl 5,6-trans-3-(2-acetamidoethylthio)-6-(1-hydroxy-2-methylsulfonylethyl)-7-oxo-1-azabicyclo[3.2.0]hept-2-ene-2-carboxylate Using 116 mg of 3,4-trans-4-[3-diazo-3-(4-nitrobenzyloxycarbonyl)-2-oxopropyl]-3-[1-(2-methoxyethoxymethoxy)-2-methylsulfonylethyl]azetidin-2-one (mixture of isomers A and B) as obtained in Reference Example 26 and following the procedure of Example 2(a), 28 mg of the title compound is obtained as a white frothy substance.

IR$\nu_{max}^{KBr}$ cm$^{-1}$: 3430, 1770, 1700, 1640, 1340, 1110.
UV$\lambda_{max}^{EtOH}$ nm: 268, 321.

(b) Production of sodium 5,6-trans-3-(2-acetamidoethylthio)-6-(1-hydroxy-2-methylsulfonylethyl)-7-oxo-1-azabicyclo[3.2.0]hept-2-ene-2-carboxylate (mixture of isomers A and B)

Using 44 mg of the 4-nitrobenzyl ester obtained by the above procedure (a) and following the procedure of Example 1(c), the title compound (15 mg) is obtained as a light-yellow powder.

IR$\nu_{max}^{KBr}$ cm$^{-1}$: 3400, 1755, 1630.
UV$\lambda_{max}^{H2O}$ nm(E$_{1\ cm}^{1\%}$): 300(147).
NMR(90 MHz, D$_2$O)δ: 2.10(3H, s), 3.31(2H, s), 2.9~4.0(9H, m), 4.35(1H, m), 4.70(1H, m).

EXAMPLE 8

5,6-cis-3-(2-Piperazinoethylthio)-6-(1-hydroxy-3-thiacyclopentyl-3,3-dioxido)-7-oxo-1-azabicyclo[3.2.0]-hept-2-ene-2-carboxylic acid (a) Production of 4-nitrobenzyl 5,6-cis-3-[2-[4-(4-nitrobenzyloxycarbonyl)piperazino]ethylthio]-6-(1-hydroxy-3-thiacyclopentyl-3,3-dioxido)-7-oxo-1-azabicyclo[3.2.0]hept-2-ene-2-carboxylate Using 150 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 and following the procedure of Example 2(a), the title compound (55 mg) is obtained as an oil.

IR$\nu_{max}^{Neat}$ cm$^{-1}$: 3350, 1770, 1710.
UV$\lambda_{max}^{EtOH}$ nm: 268, 320.
NMR(90 MHz, acetone-d$_6$)δ: 2.3~4.0(20H, m), 4.07(1H, d, J=6 Hz), 4.4(1H, m), 5.23(2H, s), 5.38(2H, ABq, J=24, 15 Hz), 7.63(2H, d, J=9 Hz), 7.74(2H, d, J=9 Hz), 8.21(2H, d, J=9 Hz).

(b) Production of 5,6-cis-3-(2-piperazinoethylthio)-6-(1-hydroxy-3-thiacyclopentyl-3,3-dioxido)-7-oxo-1-azabicyclo[3.2.0]hept-2-ene-2-carboxylic acid Using 55 mg of the 4-nitrobenzyl ester obtained by the above procedure (a) and following the procedure of Example 1(c), the title compound (8.6 mg) is obtained as a light-yellow powder.

IR$\nu_{max}^{KBr}$ cm$^{-1}$: 3440, 1755.
UV$\lambda_{max}^{H2O}$ nm(E$_{1\ cm}^{1\%}$): 299(110).

NMR(90 MHz, D$_2$O)δ: 2.5~4.0(20H, m), 4.15(1H, d, J=6 Hz), 4.5(1H, m).

EXAMPLE 9

Sodium 5,6-cis-3-(2-hydroxyethylthio)-6-(1-hydroxy-3-thiacyclopentyl-3,3-dioxido)-7-oxo-1-azabicyclo[3.2.0]-hept-2-ene-2-carboxylate (a) Production of 4-nitrobenzyl 5,6-cis-3-(2-hydroxyethylthio)-6-(1-hydroxy-3-thiacyclopentyl-3,3-dioxido)-7-oxo-1-azabicyclo[3.2.0]hept-2-ene-2-carboxylate Using 150 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 and following the procedure of Example 2(a), the title compound (34 mg) is obtained as a frothy substance.

IR$\nu_{max}^{KBr}$ cm$^{-1}$: 3450, 1755.
UV$\lambda_{max}^{EtOH}$ nm: 267, 320.
NMR(90 MHz, acetone-d$_6$)δ: 2.5(2H, m), 2.8~3.9(8H, m), 3.73(2H, t, J=6 Hz), 4.07(1H, d, J=6 Hz), 4.4(1H, m), 5.38(2H, ABq, J=23, 12 Hz), 7.78(2H, d, J=9 Hz), 8.21(2H, d, J=9 Hz).

(b) Production of sodium 5,6-cis-3-(2-hydroxyethylthio)-6-(1-hydroxy-3-thiacyclopentyl-3,3-dioxido)-7-oxo-1-azabicyclo[3.2.0]hept-2-ene-2-carboxylate Using 51 mg of the 4-nitrobenzyl ester obtained by the above procedure (a) and following the procedure of Example 1(c), the title compound (20 mg) is obtained as a light-yellow powder.

IR$\nu_{max}^{KBr}$ cm$^{-1}$: 8420, 1755.
UV$\lambda_{max}^{H2O}$ nm(E$_{1\ cm}$1%): 300(91).
NMR(90 MHz, D$_2$O)δ: 2.65(2H, m), 2.9~4.0(6H, m), 3.17(2H, t, J=6 Hz), 3.91(2H, t, J=6 Hz), 4.16(1H, d, J=6 Hz), 4.5(1H, m).

EXAMPLE 10

Sodium 5,6-cis-3-ethylthio-6-(1-hydroxy-3-thiacyclopentyl-3,3-dioxido)-7-oxo-1-azabicyclo[3.2.0]hept-2-ene-2-carboxylate (a) Production of 4-nitrobenzyl 5,6-cis-3-ethylthio-6-(1-hydroxy-3-thiacyclopentyl-3,3-dioxido)-7-oxo-1-azabicyclo[3.2.0]hept-2-ene-2-carboxylate Using 86 mg of 3,4-cis-4-[3-diazo-3-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 and following the procedure of Example 2(a), the title compound (8 mg) is obtained as an oil.

IR$\nu_{max}^{Neat}$ cm$^{-1}$: 1760.
UV$\lambda_{max}^{EtOH}$ nm: 267, 321.
NMR(90 MHz, acetone-d$_6$)δ: 1.26(3H, t, J=7 Hz), 2.56(2H, q, J=7 Hz), 2.6(2H, m), 2.9~3.4(6H, m), 4.07(1H, d, J=6 Hz), 4.45(1H, m), 5.38(2H, ABq, J=22, 14 Hz), 7.78(2H, d, J=9 Hz), 8.23(2H, d, J=9 Hz).

(b) Production of sodium 5,6-cis-3-ethylthio-6-(1-hydroxy-3-thiacyclopentyl-3,3-dioxido)-7-oxo-1-azabicyclo[3.2.0]hept-2-ene-2-carboxylate Using 40 mg of the 4-nitrobenzyl ester obtained by the above procedure (a) and following the procedure of Example 1 (c), the title compound (4 mg) is obtained as a light-yellow powder.

IR$\nu_{max}^{KBr}$ cm$^{-1}$: 3440, 1750.
UV$\lambda_{max}^{H2O}$ nm (E$_{1\ cm}$1%): 302 (104).
NMR(90 MHz, D$_2$O)δ: 1.40(3H, t, J=7 Hz), 2.6(2H, m), 3.00(2H, q, J=7 Hz), 3.2~4.0(6H, m), 4.12(1H, d, J=6 Hz), 4.4(1H, m).

EXAMPLE 11

Sodium 5,6-trans-3-(2-acetamidoethylthio)-6-(1-hydroxy-2-methylsulfonylethyl)-7-oxo-1-azabicyclo[3.2.0]hept-2-ene-2-carboxylate (Isomer B)

(a) Production of 4-nitrobenzyl 5,6-trans-3-(2-acetamidoethylthio)-6-(1-hydroxy-2-methylsulfonylethyl)-7-oxo-1-azabicyclo[3.2.0]hept-2-ene-2-carboxylate Using 103 mg of 3,4-trans-4-[3-diazo-3-(4-nitrobenzyloxycarbonyl)-2-oxopropyl]-3-[1-(2-methoxyethoxymethoxy)-2-methylsulfonylethyl]azetidin-2-one (isomer B) as obtained in Reference Example 33 and following the procedure of Example 2 (a), the title compound (32 mg) is obtained as a white frothy substance.

IR$\nu_{max}^{KBr}$ cm$^{-1}$: 3400, 1770, 1700, 1640, 1350, 1120.
UV$\lambda_{max}^{EtOH}$ nm: 268, 321.

(b) Production of sodium 5,6-trans-3-(2-acetamidoethylthio)-6-(1-hydroxy-2-methylsulfonylethyl)-7-oxo-1-azabicyclo[3.2.0]hept-2-ene-2-carboxylate (isomer B)

Using 52 mg of the 4-nitrobenzyl ester obtained by the above procedure (a) and following the procedure of Example 1 (c), the title compound (14 mg) is obtained as a light-yellow powder.

IR$\nu_{max}^{KBr}$ cm$^{-1}$: 3400, 1755, 1630.
UV$\lambda_{max}^{H2O}$ nm (E$_{1\ cm}$1%): 300(155).
NMR(90 MHz, D$_2$O)δ: 2.15(3H, s), 3.33(3H, s), 2.9~4.0(9H, m), 4.4(1H, m), 4.8(1H, m).

EXAMPLE 12

Sodium 5,6-cis-3-(2-acetamidoethylthio)-6-(1-hydroxy-2-methylsulfonylethyl)-7-oxo-1-azabicyclo[3.2.0]hept-2-ene-2-carboxylate (a) Production of 4-nitrobenzyl 5,6-cis-3-(2-acetamidoethylthio)-6-(1-hydroxy-2-methylsulfonylethyl)-7-oxo-1-azabicyclo[3.2.0]hept-2-ene-2-carboxylate Using 80 mg of 3,4-cis-4-[3-diazo-3-(4-nitrobenzyloxycarbonyl-2-oxopropyl]-3-[1-(2-methoxyethoxymethoxy)-2-methylsulfonylethyl]azetidin-2-one as obtained in Reference Example 40 and following the procedure of Example 2 (a), the title compound (25 mg) is obtained as a powder.

IR$\nu_{max}^{KBr}$ cm$^{-1}$: 3400, 1765, 1695, 1640, 1340, 1130.
UV$\lambda_{max}^{EtOH}$ nm: 267, 320.

(b) Production of sodium 5,6-cis-3-(2-acetamidoethylthio)-6-(1-hydroxy-2-methylsulfonylethyl)-7-oxo-1-azabicyclo[3.2.0]hept-2-ene-2-carboxylate Using 56 mg of the 4-nitrobenzyl ester obtained by the above procedure (a) and following the procedure of Example 1 (c), the title compound (16 mg) is obtained as a white frothy substance.

IR$\nu_{max}^{KBr}$ cm$^{-1}$: 3400, 1760, 1640.
UV$\lambda_{max}^{H2O}$ nm (E$_{1\,cm}$1%): 299(169).
NMR(90 MHz, D$_2$O)δ: 2.15(3H, s), 3.31(3H, s), 3.0~4.1(9H, m), 4.45(1H, m), 4.8(1H, m).

EXAMPLE 13

Sodium 5,6-cis-3-[(E)-2-acetamidovinylthio]-6-(1-hydroxy-3-thiacyclopentyl-3,3-dioxido)-7-oxo-1-azabicyclo[3.2.0]-hept-2-ene-2-carboxylate (a) Production of 4-nitrobenzyl 5,6-cis-3[(E)-2-acetamidovinylthio]-6-(1-hydroxy-3-thiacyclopentyl-3,3-dioxido)-7-oxo-1-azabicyclo[3.2.0-]hept-2-ene-carboxylate Using 123 mg of 3,4-cis-4-[3-diazo-3-(4-nitrobenzyloxycarbonyl)-2-oxopropyl]-3-[1-(2-methoxyethoxymethoxy)-3-thiacyclopentyl-3,3-dioxido]azetidin-2-one as obtained in Reference Example 7 and following the procedure of Example 2 (a), the title compound (45 mg) is obtained as a frothy substance.

IR$\nu_{max}^{KBr}$ cm$^{-1}$: 1765, 1690, 1620.
UV$\lambda_{max}^{MeOH}$ nm: 230, 265, 326.
NMR(90 MHz, CD$_3$COCD$_3$)δ: 1.97(3H, s), 2.45(2H, m), 2.7~3.9(6H, m), 4.06(1H, d, J=6 Hz), 4.4 (1H, m), 5.38(2H, ABq, J=22, 14 Hz), 5.97(1H, d, J=14 Hz), 7.17(1H, dd, J=14, 13 Hz), 7.73(2H, d, J=9 Hz), 8.21(2H, d, J=9 Hz), 9.76(1H, d, J=13 Hz).

(b) Production of sodium 5,6-cis-3-[(E)-2-acetamidovinylthio]-6-(1-hydroxy-3-thiacyclopentyl-3,3-dioxido)-7-oxo-1-azabicyclo[3.2.0-]hept-2-ene-2-carboxylate Using 61 mg of the 4-nitrobenzyl ester obtained by the above procedure (a) and following the procedure of Example 1 (c), the title compound (19 mg) is obtained as a colorless powder.

IR$\nu_{max}^{KBr}$ cm$^{-1}$: 1755, 1670, 1620.
UV$\lambda_{max}^{H2O}$ nm (E$_{1\,cm}$1%): 229(312), 306(312).
NMR(90 MHz, D$_2$O)δ: 2.20(3H, s), 2.65(2H, m), 3.0~4.0(6H, m), 4.12(1H, d, J=6 Hz), 4.50(1H, m) 6.15(1H, d, J=13 Hz), 7.28(1H, d, J=13 Hz).

EXAMPLE 14

Sodium 5,6-cis-3-[(Z)-2-acetamidovinylthio]-6-(1-hydroxy-3-thiacyclopentyl-3,3-dioxido)-7-oxo-1-azabicyclo[3.2.0]-hept-2-ene-2-carboxylate (a) Production of 4-nitrobenzyl 5,6-cis-3-[(Z)-2-acetamidovinylthio]-6-(1-hydroxy-3-thiacyclopentyl-3,3-dioxido)-7-oxo-1-azabicyclo[3.2.0-]hept-2-ene-2-carboxylate Using 90 mg of 3,4-cis-4-[3-diazo-3-(4-nitrobenzyloxycarbonyl)-2-oxopropyl]-3-[1-(2-methoxyethoxymethyl)-3-thiacyclopentyl-3,3-dioxido]azetidin-2-one as obtained in Reference Example 7 and following the procedure of Example 2 (a), the title compound (27 mg) is obtained as a frothy substance.

IR$\nu_{max}^{KBr}$ cm$^{-1}$: 1775, 1700, 1630.
UV$\lambda_{max}^{MeOH}$ nm: 237, 263, 326.
NMR(90 MHz, acetone-d$_6$)δ: 2.06(3H, s), 2.45(2H, m), 2.8–3.9(6H, m), 4.08(1H, d, J=6 Hz), 4.40(1H, m), 5.42(2H, ABq, J=24, 14 Hz), 5.46(1H, d, J=8 Hz), 7.28(1H, dd, J=8, 12 Hz), 7.78(2H, d, J=9 Hz), 8.23(2H, d, J=9 Hz), 9.10(1H, m).

(b) Production of sodium 5,6-cis-3-[(Z)-2-acetamidovinylthio]-6-(1-hydroxy-3-thiacyclopentyl-3,3-dioxido)-7-oxo-1-azabicyclo[3.2.0-]hept-2-ene-2-carboxylate Using 59 mg of the 4-nitrobenzyl ester obtained by the above procedure (a) and following the procedure of Example 1 (c), the title compound (19 mg) is obtained as acolourless powder.

IR$\nu_{max}^{KBr}$ cm$^{-1}$: 1760, 1680, 1630.
UV$\lambda_{max}^{H2O}$ (E$_{1\,cm}$1%): 233(291), 305(274).
NMR(90 MHz, D$_2$O)δ: 226(3H, s), 2.65(2H, m), 3.0–4.0(6H, m), 4.13(1H, d, J=6 Hz), 4.50(1H, m), 5.86(1H, d, J=8 Hz), 7.30(1H, d, J=8 Hz).

Example 15-21

(a) The following compounds are obtained according to the same manner as Example 1(b).

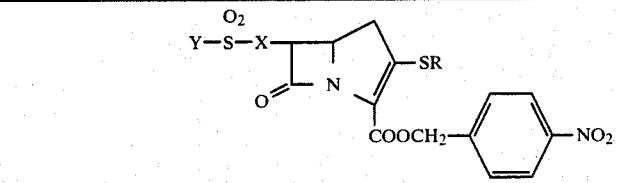

| Ex. No. | Y—SO$_2$—X— | R | (90MHz, CDCl$_3$) δ: |
|---|---|---|---|
| 15(a) | 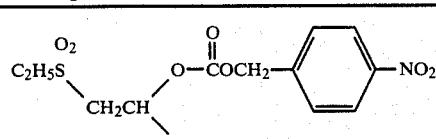 | —CH$_2$CH$_2$NHCOCH$_3$ | 1.30(3H,t,J=7.5Hz), 2.0(3H s), 3.08(2H,q,J=7.5Hz), 2.8–3.7(6H,m,3.68(2H,d,J=6Hz) 4.1–4.6(2H,m), 5.36(2H,s) 5.38(2H,ABq,J=14,23HZ) 5.8(1H,m), 7.35(1H,bs), 7.66(2H,d,J=9Hz), 7.74(2H,d, J=9Hz), 8.18(2H,d,J=9Hz), 8.21(2H,d,J=9Hz) |
| 16(a) | 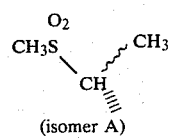<br>(isomer A) | —CH$_2$CH$_2$NHCOCH$_3$ | 1.58(3H,d,J=6Hz) 1.93(3H,s) 2.90(3H,s) 2.9–3.6(8H,m), 4.35(1H,m) 5.33(2H,ABq,J=24,13Hz) 6.10(1H,m), 7.60(2H,d,J= 9Hz), 8.20(2H,d,J=9Hz) |

-continued

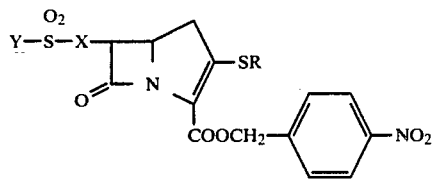

| Ex. No. | Y—SO₂—X— | R | (90MHz, CDCl₃) δ: |
|---|---|---|---|
| 17(a) | O₂<br>CH₃S\_CH(CH₃)⫻<br>(isomer B) | —CH₂CH₂NHCOCH₃ | 1.53(3H,d,J=6Hz),<br>1.93(3H,s), 2.97(3H,s)<br>2.8–4.0(8H,m)<br>4.40(1H,m), 5.35(2H,<br>ABq,J=24,13Hz)<br>6.17(1H,m),<br>7.60(2H,d,J=9Hz)<br>8.20(2H,d,J=9Hz) |

(b) The following compounds are obtained according to the same manner as Example 2(a)

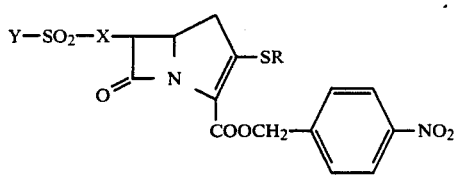

| Ex. No. | Y—SO₂—X— | R | UV or NMR spectrum |
|---|---|---|---|
| 18(a) | O₂<br>S (tetrahydrothiophene)<br>—OH | pyrrolidine-N—COOCH₂—C₆H₄—NO₂ | NMR(90MHz,acetone-d₆)δ:<br>2.3–2.6(2H,m), 3.0–4.0(13H,<br>m), 4.10(1H,d,J=6Hz),<br>4.4(1H,m), 5.23(2H,s),<br>5.38(2H,ABq,J=14,25Hz),<br>7.61(2H,d,J=9Hz), 7.76(2H,d,<br>J=9Hz), 8.21(4H,d,J=9Hz) |
| 19(a) | O₂<br>CH₃S—C(OH)—CH₃S<br>O₂ | —CH₂CH₂NHCOCH₃ | UV λ$_{max}^{MeOH}$ nm: 264, 310 |
| 20(a) | Ph—SO₂—CH₂CH(OH)— | —CH₂CH₂NHCOCH₃ | NMR(90MHz, CDCl₃)δ:<br>2.10(3H,s), 2.7–3.7(8H,m),<br>3.79(1H,dd,J=6,10Hz),<br>4.1–5.0(2H,m), 5.34(2H,ABq,<br>J=13,24Hz), 7.5–8.1(7H,m)<br>8.21(2H,d,J=9Hz) |
| 21(a) | Ph—SO₂—CH₂CH(OH)— | —CH₂CH₂NH—COOCH₂—C₆H₄—NO₂ | NMR(90MHz, acetone-d₆)δ:<br>2.9–4.0(9H,m), 4.1–4.8(2H,m),<br>5.21(2H,s), 5.33(2H,ABq,<br>J=15,27Hz), 6.7(1H,bs),<br>7.4–8.1(9H,m), 8.17(4H,d,<br>J=9Hz) |

(c) The following compounds are obtained according to the same manner as any of Examples 1–14,

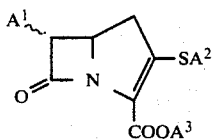

| Ex. No. | A¹ | A² | A³ | (A) (B) (C) | IR $\nu_{max}^{KBr}$ cm$^{-1}$, (C)NMR(90MHz,D$_2$O)δ UV $\lambda_{max}^{H2O}$ nm(E$_{1cm}^{1\%}$) |
|---|---|---|---|---|---|
| 15(b) | 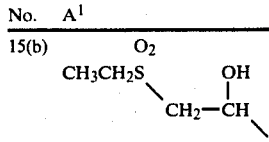 | —CH$_2$CH$_2$NHCOCH$_3$ | Na | (A) (B) (C) | 1750<br>299(153)<br>1.50(3H,t,J=7.5Hz),<br>2.16(3H,s), 3.46(2H,q,<br>J=7.5Hz), 3.69(2H,d,<br>J=6Hz), 3.0–3.8(6H,m)<br>4.03(1H,dd,J=10,5Hz)<br>4.3–4.8(2H,m) |
| 16(b) | 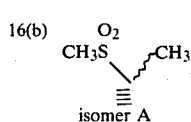 isomer A | —CH$_2$CH$_2$NHCOCH$_3$ | Na | (A) (B) (C) | 1755, 1650<br>300(176)<br>1.53(3H,d,J=6Hz), 2.00<br>(3H,s), 2.8–4.0(8H,m),<br>3.10(3H,s), 4.3(1H,m) |
| 17(b) | 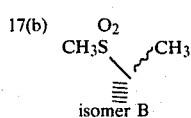 isomer B | —CH$_2$CH$_2$NHCOCH$_3$ | Na | (A) (B) (C) | 1750, 1650<br>300<br>1.53(3H,d,J=6Hz), 2.00<br>(3H,s), 2.8–4.0(8H,m),<br>3.17(3H,s), 4.4(1H,m) |
| 18(b) | 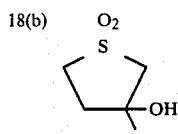 | 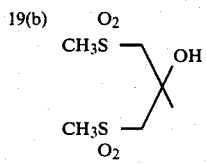 | H | (A) (B) (C) | 3440, 1760<br>297(157)<br>1.9–2.6(2H,m), 2.6(2H,m),<br>3.2–4.2(11H,m), 4.15(1H,d,<br>J=6Hz), 4.5(1H,m) |
| 19(b) | CH$_3$S—<br>CH$_3$S—<br>O$_2$<br>—OH | —CH$_2$CH$_2$NHCOCH$_3$ | Na | (B) (C) | 299<br>2.20(3H,s), 3.40(3H,s),<br>3.45(3H,s), 4.40(1H,d,<br>J=6Hz), 2.80–4.90(1H,m) |
| 20(b) | 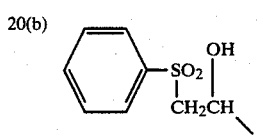 | —CH$_2$CH$_2$NHCOCH$_3$ | Na | (A) (B) (C) | 3400, 1750, 1630<br>216(262), 299(140)<br>2.13(3H,s), 3.0–4.0<br>(9H,m), 4.1–4.8(2H,m),<br>7.7–8.2(5H,m) |
| 21(b) | 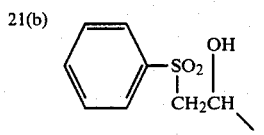 | —CH$_2$CH$_2$NH$_2$ | H | (A) (B) (C) | 3400, 1755<br>296<br>3.0–4.1(9H,m), 4.2–4.9<br>(2H,m), 7.6–8.2(5H,m) |

EXAMPLE 22

Sodium 5,6-cis-3-(2-acetamidoethylthio)-6-(1-hydroxy-3-thiacyclopentyl-3,3-dioxido)-7-oxo-1-azabicyclo[3.2.0]-hept-2-ene-2-carboxylate (250 mg) is placed in a sterile vial (capacity 17 ml) and the vial is stoppered sealedly. For use, the sterile vial is unstoppered and 1 ml of pyrogen-free distilled water is added thereto, whereby an injectable solution is prepared.

Example 23

5,6-cis-3-(2-Formimidoylaminoethylthio)-6-(1-hydroxy-3-thiacyclopentyl-3,3-dioxido)-7-oxo-1-azabicyclo[3.2.0]-hept-2-ene-2-carboxylic acid (250 mg) is placed in a sterile vial (capacity 12 ml) and the vial is stoppered sealedly. For use, the sterile vial is unstoppered and 1 ml of pyrogen-free distilled water is added thereto, whereby an injectable solution is prepared.

Test Example 1

Several examples of the compound (I) as obtained in Examples were tested for MIC (mcg/ml) by the following method.

(a) Test method

The MIC of each test compound was determined by the agar dilution method. Thus, 1.0 ml of each aqueous serial dilution of the test compound was poured into a petri dish and then 0.9 ml of Trypticase soy agar was poured into the dish followed by intimate mixing. The mixed agar plate was smeared with the suspension of a test organism (about $10^8$ CFU/ml). The lowest concentration of the test compound at which the growth of the test organism was found to have been completely inhibited after 18 hours of incubation at 37° C. was recorded as the MIC (minimal inhibitory concentration).

(b) Test organisms
(1) *Staphylococcus aureus* FDA 209P
(2) *Escherichia coli* 0-111
(3) *Citrobacter freundii* IFO 12681
(4) *Klebsiella pneumoniae* DT (c) Results The MIC (minimal inhibitory concentration) values for the test compounds are shown in Table 1.

TABLE 1

| Test organism | MIC values (mcg/ml) Test compound (Example No.) | | | | | |
|---|---|---|---|---|---|---|
| | 1 (c) | 2 (b) | 12 (b) | 13 (b) | 15 (b) | 20 (b) |
| (1) | 3.13 | 0.78 | 1.56 | 1.56 | 6.25 | 1.59 |
| (2) | 0.39 | 3.13 | 0.39 | 0.39 | 0.2 | 0.39 |
| (3) | 3.13 | 6.25 | 3.13 | 1.56 | 3.13 | 1.56 |
| (4) | 3.13 | 6.25 | 1.56 | 0.78 | 3.13 | 3.13 |

Test Example 2

Several examples of the objective compound (I) as obtained in Examples were tested for stability against a mouse Kidney homogenate by the following method.

(a) Test method

A kidney homogenate was prepared by grinding down 50 g of the mouse kidney in 200 ml of cooled 0.05M phosphate buffer (pH 6.9) and stored at −20° C. A 200 μl portion of this mouse kidney homogenate and 200 μl of an aqueous solution of the test compound (1 mg/ml) were intimately mixed and kept at 30° C. At 10-minute intervals, a 25 μl portion of the mixture was taken and added to 25 μl of ice bath-cooled methanol to thereby terminate the reaction between renal enzymes and the test compound. The amount of the remaining test compound was determined by measuring the inhibitory action against β-lactamase produced by *Proteus vulgaris* GN4413 or *Enterobacter cloacae* TN1282 by the method described in Journal of Antibiotics, 34, 212–217 (1981).

(b) Results

The half life period of each compound tested is shown in Table 2.

TABLE 2

| Test compound (Example No.) | 1 (c) | 2 (b) | 12 (b) | 13 (b) | 15 (b) | 20 (b) |
|---|---|---|---|---|---|---|
| Half life (minutes) ($T_{\frac{1}{2}}$) | >120 | >120 | >120 | >120 | >120 | >120 |

Test Example 3

Determination of the inhibitor concentration required to inhibit the enzyme activity by 50%.

The β-lactamase produced by *Enterobacter cloacae* TN 1282 is used as a typical example of cephalosporinase, and that produced by *Staphylococcus aureus* 1840 as typical example of penicillinase. The β-lactamase is incubated in 0.05M phosphate buffer (pH 7) with an appropriate dilution of compound (I) preparation at 30° C. for 10 minutes. Cephalothin (When the β-lactamase produced by *Enterobacter cloacae* TN 1282 is used) or ampicillin (When the β-lactamase produced by *Staphylococcus aureus* 1840 is used) is then added in an amount sufficient to produce a final concentration of 0.1 mM, and the enzymatic reaction is allowed to proceed for 10 minutes. The enzyme activity is determined by the microiodometric method [Journal of general Microbiology, vol. 33, page 121 (1963)]. Hereinafter, the inhibitor concentration required to inhibit the enzyme activity by 50% is expressed as $I_{50}$. The $I_{50}$ values for the β-lactamase produced by *Enterobacter cloacae*, and the β-lactamase produced by *Staphylococcus aureus* are shown in Table 3.

TABLE 3

| β-lactamase producing microorganism | Tested compound (Example No.) | | | | | | |
|---|---|---|---|---|---|---|---|
| | 1 (c) | 2 (b) | 12 (b) | 13 (b) | 15 (b) | 18 (b) | 20 (b) |
| *Enterobacter cloacae* TN 1282 | 0.19 | 0.0095 | 0.025 | 0.040 | 0.065 | 0.035 | 0.039 |
| *Staphylococcus aureus* 1840 | 0.14 | 0.14 | 0.21 | 0.022 | 0.019 | 0.24 | 1.9 |

We claim:
1. The compounds:
   (a) 5,6-cis-3-(2-pyrimidinylthio)-6-(1-hydroxy-3-thiacyclopentyl-3,3dioxido)-7-oxo-1-(azabicyclo-[3.2.0]-hept-2-ene-2-carboxylic acid,
   (b) 5,6-cis-3-(2-aminoethylthio)-6-(1-hydroxy-3-thiacyclopentyl-3,3-dioxido)-7-oxo-1-azabicyclo-[3.2.0]-hept-2-ene-2-carboxylic acid,
   (c) 5,6-cis-3-(2-piperazinoethylthio)-6-(1-hydroxy-3-thiacyclopentyl-3,3-dioxido)-7-oxo-1-azabicyclo-[3.2.0]hept-2-ene-2-carboxylic acid,
   (d) 5,6-cis-3-[(E)-2-acetamidovinylthio]-6-(1-hydroxy-3-thiacyclopentyl-3,3-dioxido)-7-oxo-1-azabicyclo-[3.2.0]hept-2-ene-2-carboxylic acid,
   (e) 5,6-cis-3-[(Z)-2-acetamidovinylthio]-6-(1-hydroxy-3-thiacyclopentyl-3,3-dioxido)-7-oxo-1-azabicyclo[3.2.0]hept-2-ene-2-carboxylic acid,
   (f) 5,6-cis-3-(3-pyrrolidinylthio)-6-(1-hydroxy-3-thiacyclopentyl-3,3-dioxido)-7-oxo-1-azabicyclo-[3.2.0]hept-2-ene-2-carboxylic acid, and
   pharmaceutically acceptable salts thereof.

2. The compound as claimed in claim 1, the compound being 5,6-cis-3-(2-pyrimidinylthio)-6-(1-hydroxy-3-thiacyclopentyl-3,3-dioxido)-7-oxo-1-azabicyclo[3.2.0]hept-2-ene-2-carboxylic acid and pharmaceutically acceptable salts thereof.

3. The compound as claimed in claim 1, the compound being 5,6-cis-3-(2-aminoethylthio)-6-(1-hydroxy-3-thiacyclopentyl-3,3-dioxido)-7-oxo-1-azabicyclo-[3.2.0]hept-2-ene-2-carboxylic acid and pharmaceutically acceptable salts thereof.

4. The compound as claimed in claim 1, the compound being 5,6-cis-3-(2-piperazinoethylthio)-6-(1-hydroxy-3-thiacyclopentyl-3,3-dioxido)-7-oxo-1-azabicyclo-[3.2.0]hept-2-ene-2-carboxylic acid and pharmaceutically acceptable salts thereof.

5. The compound as claimed in claim 1, the compound being 5,6-cis-3-[(E)-2-acetamidovinylthio]-6-(1-hydroxy-3-thiacyclopentyl-3,3-dioxido)-7-oxo-1-azabicyclo-[3.2.0]hept-2-ene-2-carboxylic acid and pharmaceutically acceptable salts thereof.

6. The compound as claimed in claim 1, the compound being 5,6-cis-3-[(Z)-2-acetamidovinylthio]-6-(1-hydroxy-3-thiacyclopentyl-3,3-dioxido)-7-oxo-1- azabicyclo-[3.2.0]hept-2-ene-2-carboxylic acid and pharmaceutically acceptable salts thereof.

7. The compound as claimed in claim 1, the compound being 5,6-cis-3-(3-pyrrolidinylthio)-6-(1-hydroxy-3-thiacyclopentyl-3,3-dioxido)-7-oxo-1-zazbicyclo-[3.2.0]hept-2-ene-2-carboxylic acid and pharmaceutically accepable salts thereof.

8. An antibacterial composition which comprises an antibacterially effective amount of a compound as defined in claim 1, and a pharmaceutically acceptable excipient.

* * * * *